United States Patent
Lin et al.

(10) Patent No.: US 12,054,543 B2
(45) Date of Patent: Aug. 6, 2024

(54) CLDN 18.2-SPECIFIC MONOCLONAL ANTIBODIES AND METHODS OF USE THEREOF

(71) Applicant: ACCURUS BIOSCIENCES, INC., Richmond, CA (US)

(72) Inventors: Haishan Lin, Richmond, CA (US); Richard Zhang, Richmond, CA (US)

(73) Assignee: ACCURUS BIOSCIENCES, INC., Richmond, CA (US)

( * ) Notice: Subject to any disclaimer, the term of this patent is extended or adjusted under 35 U.S.C. 154(b) by 773 days.

(21) Appl. No.: 17/262,351

(22) PCT Filed: Jul. 24, 2019

(86) PCT No.: PCT/US2019/043316
§ 371 (c)(1),
(2) Date: Jan. 22, 2021

(87) PCT Pub. No.: WO2020/023679
PCT Pub. Date: Jan. 30, 2020

(65) Prior Publication Data
US 2021/0214433 A1 Jul. 15, 2021

Related U.S. Application Data

(60) Provisional application No. 62/703,036, filed on Jul. 25, 2018.

(51) Int. Cl.
*C07K 16/28* (2006.01)
*A61K 47/68* (2017.01)
*C07K 14/705* (2006.01)
*C07K 14/725* (2006.01)
*G01N 33/68* (2006.01)

(52) U.S. Cl.
CPC .......... *C07K 16/28* (2013.01); *A61K 47/6849* (2017.08); *C07K 14/7051* (2013.01); *C07K 14/70517* (2013.01); *C07K 14/70578* (2013.01); *G01N 33/6854* (2013.01); *C07K 2317/24* (2013.01); *C07K 2317/31* (2013.01); *C07K 2317/33* (2013.01); *C07K 2317/565* (2013.01); *C07K 2317/77* (2013.01); *C07K 2317/92* (2013.01); *C07K 2319/02* (2013.01); *C07K 2319/03* (2013.01); *C07K 2319/30* (2013.01); *C07K 2319/33* (2013.01)

(58) Field of Classification Search
CPC ................ C07K 16/28; C07K 14/7051; C07K 14/70517; C07K 14/70578; C07K 2317/24; C07K 2317/31; C07K 2317/33; C07K 2317/565; C07K 2317/77; C07K 2317/92; C07K 2319/02; C07K 2319/03; C07K 2319/30; C07K 2319/33; A61K 47/6849; G01N 33/6854
See application file for complete search history.

(56) References Cited

U.S. PATENT DOCUMENTS

| | | |
|---|---|---|
| 2010/0061988 A1 | 3/2010 | Hansen |
| 2013/0324432 A1 | 12/2013 | Shaw et al. |
| 2014/0127223 A1 | 5/2014 | Yamazaki et al. |
| 2018/0282389 A1 | 10/2018 | Sahin et al. |

FOREIGN PATENT DOCUMENTS

| | | | |
|---|---|---|---|
| CA | 3030257 A1 * | 1/2018 | ........... A61K 31/282 |
| CN | 107960056 A | 4/2018 | |
| WO | WO-2016/077720 A1 | 5/2016 | |

OTHER PUBLICATIONS

Extended European Search Report on European Patent Application No. 19842207.3 dated Aug. 11, 2022 (16 pages).
Partial Supplementary European Search Report on European Application No. 19842207.3 dated May 9, 2022 (21 pages).
Sahin et al., "Claudin-18 Splice Variant 2 is a Pan-Cancer Target Suitable for Therapeutic Antibody Development", Clinical Cancer Research, Dec. 1, 2008, vol. 14, No. 23, pp. 7624-7634.
Singh et al., "Anti-Claudin 18.2 Antibody as New Targeted Therapy for Advanced Gastric Cancer", Journal of Hematology & Oncology, May 2017, vol. 10, pp. 1-5.
International Search Report & Written Opinion for International Patent Application No. PCT/US2019/043316 dated Jan. 7, 2020 (12 pages).

* cited by examiner

*Primary Examiner* — Nelson B Moseley, II
*Assistant Examiner* — Alyssa Rae Stonebraker
(74) *Attorney, Agent, or Firm* — Foley & Lardner LLP

(57) ABSTRACT

Provided herein are novel anti-CLDN 18.2 antibodies and chimeric antigen receptors (CAR), cells or compositions comprising the same, vector or plasmid encoding anti-CLDN 18.2 CAR, anti-CLDN 18.2 antibody-drug conjugates (ADCs), bispecific antibodies containing anti-CLDN 18.2 antibodies, and methods for producing the same, or using the same for detecting or treating ovarian cancer or prostate cancer. Also provided herein are anti-CLDN 18.2 antibodies, compositions comprising the same, nucleic acid sequence encoding the same, and a kit for detecting CLDN 18.2.

14 Claims, 14 Drawing Sheets
Specification includes a Sequence Listing.

Anti-CLDN18.2 antibody, cT155S2

Cell surface (0 h at 37C)   Internalization (3 h at 37C)

Anti-CLDN18.2 antibody, cT158S2

Cell surface (0 h at 37C)　　　　Internalization (3 h at 37C)

Anti-CLDN18.2 antibody, cT224S8

Cell surface (0 h at 37C)  Internalization (3 h at 37C)

Anti-CLDN18.2 antibody, cT192S2

Cell surface (0 h at 37C)　　　　Internalization (3 h at 37C)

Anti-CLDN18.2 antibody, cT252S4

Cell surface (0 h at 37C)  Internalization (3 h at 37C)

Binding of humanized Anti-CLDN18.2 antibodies to CHO/CLDN18.2 Cells

SEQUENCE LISTING

```
<160> NUMBER OF SEQ ID NOS: 107

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Asn Leu Leu Asn Ser Ser Asn Gln Lys Asn Tyr
1               5                   10

<210> SEQ ID NO 2
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 2

Phe Ala Ser
1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln His Tyr Ser Thr Pro Leu Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser Ser Tyr Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Ser Gly Gly Gly Ser Thr
1               5

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Asn Ile Tyr Asp Gly Tyr Pro Tyr Tyr Phe Asp Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Ser Val Asp Asn Tyr Gly Phe Ser Phe
1               5                   10
```

```
<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser
1

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Ser Asn Gln Gly Pro Leu Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Thr Phe Ser Asp Tyr Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Ser Asp Gly Gly Gly Asp Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Arg His Arg Gly Ser Leu Asp Tyr
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Gln Ser Leu Val His Ser Asn Gly Asn Thr Tyr
1               5                   10

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Val Ser
1

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Gln Asn Thr His Val Pro Arg Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Phe Asn Ile Lys Asp Tyr Phe
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Asp Pro Glu Asn Gly Asp Thr
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Val Leu Gly Tyr Gly Asn Tyr Gly His Phe Tyr Tyr Ala Met Asp
1               5                   10                  15

Tyr
```

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Glu Ser Val Asp Asn Tyr Gly Phe Ser Phe
1               5                   10

<210> SEQ ID NO 20
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Arg Ala Ser
1

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Gln Gln Ser Asn Lys Val Pro Leu Thr
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Gly Phe Thr Phe Ser Asp Tyr Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Ile Ser Asn Gly Gly Gly Ser Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

```
Ala Arg His Arg Gly Ser Leu Asp Phe
1               5

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Asn Leu Leu Asn Ser Gly Asn Gln Lys Asn Tyr
1               5                   10

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Ala Ser
1

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Asn Asp Tyr Ile Tyr Pro Leu Pro
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Ser Phe Thr Gly Tyr Asn
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Asn Pro Tyr Asn Gly Gly Thr
1               5

<210> SEQ ID NO 30
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 30

Ala Arg Met Gly Leu Gly Asn Ala Met Asp Tyr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Ser Val Asp Asn Tyr Gly Phe Ser Phe
1               5                   10

<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ala Ser
1

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Ser Asn Gln Gly Pro Leu Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Phe Ser Leu Thr Ser Tyr Gly
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Trp Ser Asp Gly Arg Thr
1               5
```

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Arg His Gly Arg Tyr Asp Pro Tyr Ala Met Asp Tyr
1               5                   10

<210> SEQ ID NO 37
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gaagtgaagc tggtggagtc tgggggaggc ttagtgaagc tggagggtc cctgaaactc      60 tcctgtgcag cctctggatt cactttcagt agctatgcca tgtcttgggt tcgccagact     120
ccagagaaga ggctggagtg ggtcgcatcc attagtggtg gtgtagcac ctactatcca      180 gacagtgtga aggccgatt caccatctcc agagataatg ccaggaacat cctgtacctg      240
caaatgagct atctgaggtc tgaggacacg gccgtgtatt actgtgcaag aggagggaat    300
atctatgatg gttacccgta ctactttgac tactggggcc aaggcaccac tctcacagtc   360
tcctca                                                                366

<210> SEQ ID NO 38
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Gly Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Tyr Leu Arg Ser Glu Asp Thr Ala Val Tyr Tyr Cys Ala
                85                  90                  95

Arg Gly Gly Asn Ile Tyr Asp Gly Tyr Pro Tyr Tyr Phe Asp Tyr Trp
            100                 105                 110

Gly Gln Gly Thr Thr Leu Thr Val Ser Ser
        115                 120

<210> SEQ ID NO 39
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39

```
gacattgtga tgacccagtc tccatcctcc ctggctatgt cagtaggaca gaaggtcact      60
atgagctgca agtccagtca gaaccttta aatagtagca atcaaaagaa ctatttggcc     120
tggtaccagc agaaaccagg acagtctcct aaacttctgg tatactttgc atccactagg    180
gaatctgggg tccctgatcg cttcacaggc agtggatctg ggacagattt cactcttacc    240
atcagcagtg tgcaggctga agacctggca gtttattact gtcagcaaca ttatagcact    300
ccgctcacgt tcggtgctgg gaccaagctg gagctgaaa                           339
```

<210> SEQ ID NO 40
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

```
Asp Ile Val Met Thr Gln Ser Pro Ser Ser Leu Ala Met Ser Val Gly
1               5                   10                  15
Gln Lys Val Thr Met Ser Cys Lys Ser Ser Gln Asn Leu Leu Asn Ser
            20                  25                  30
Ser Asn Gln Lys Asn Tyr Leu Ala Trp Tyr Gln Gln Lys Pro Gly Gln
        35                  40                  45
Ser Pro Lys Leu Leu Val Tyr Phe Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Gln
                85                  90                  95
His Tyr Ser Thr Pro Leu Thr Phe Gly Ala Gly Thr Lys Leu Glu Leu
            100                 105                 110
Lys
```

<210> SEQ ID NO 41
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41

```
gaagtgaagc tggtggagtc tgggggaggc ttagtgcagc ctggagggtc cctgaaactc      60
tcctgtgcaa cctctggatt cactttcagt gactattaca tgttttggat tcgccagact    120
ccagagaaga ggctggagtg ggtcgcctcc attagtgatg gtggtggtga cacctattat    180
ccagacactg taaagggccg attcaccatc tccagagaca tgccaagaa caccctgtac    240
ctgcaaatga gccgtctgaa gtctgaggac acagccatgt attactgtgc aagacatagg    300
ggctctcttg actactgggg ccaaggcacc actctcacag tctcctca                 348
```

<210> SEQ ID NO 42
<211> LENGTH: 116
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 42

```
Glu Val Lys Leu Val Glu Ser Gly Gly Gly Leu Val Gln Pro Gly Gly
1               5                   10                  15
Ser Leu Lys Leu Ser Cys Ala Thr Ser Gly Phe Thr Phe Ser Asp Tyr
            20                  25                  30
Tyr Met Phe Trp Ile Arg Gln Thr Pro Glu Lys Arg Leu Glu Trp Val
        35                  40                  45
Ala Ser Ile Ser Asp Gly Gly Asp Thr Tyr Tyr Pro Asp Thr Val
    50                  55                  60
Lys Gly Arg Phe Thr Ile Ser Arg Asp Asn Ala Lys Asn Thr Leu Tyr
65                  70                  75                  80
Leu Gln Met Ser Arg Leu Lys Ser Glu Asp Thr Ala Met Tyr Tyr Cys
                85                  90                  95
Ala Arg His Arg Gly Ser Leu Asp Tyr Trp Gly Gln Gly Thr Thr Leu
            100                 105                 110
Thr Val Ser Ser
        115
```

<210> SEQ ID NO 43
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
gacattgtgc tgacccaatc tccagcttct ttggctgtgt ctctagggca gagggccacc    60
atctcctgca gagccagcga gagtgtggat aactatggct tagttttct gcactggtac    120
cagcagaaac caggacagcc acccaaactc ctcatctatc gtgcatccaa cctagcatct    180
gggatccctg ccaggttcag tggcagtggg tctaggacag acttcaccct caccattaat    240
cctgtggaga ctgatgatgt tgcaacctat tactgtcagc aaagtaatca gggtccactc    300
acgttcggtg ctgggaccaa gctggagctg aaa                                333
```

<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Asp Asn Tyr
            20                  25                  30
Gly Phe Ser Phe Leu His Trp Tyr Gln Gln Lys Pro Gly Gln Pro Pro
        35                  40                  45
Lys Leu Leu Ile Tyr Arg Ala Ser Asn Leu Ala Ser Gly Ile Pro Ala
    50                  55                  60
Arg Phe Ser Gly Ser Gly Ser Arg Thr Asp Phe Thr Leu Thr Ile Asn
65                  70                  75                  80
```

Pro Val Glu Thr Asp Asp Val Ala Thr Tyr Tyr Cys Gln Gln Ser Asn
                85                  90                  95

Gln Gly Pro Leu Thr Phe Gly Ala Gly Thr Lys Leu Glu Leu Lys
            100                 105                 110

<210> SEQ ID NO 45
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
gaggttcagc tgcagcagtc tgggacagag cttgtgaggt caggggcctc agtcaagttg    60
tcctgcacaa cttctggctt caacattaaa gactactttt tacactgggt gaagcagagg   120
cctgaacagg gcctggagtg gattggatgg attgatcctg agaatggtga tactaaatat   180
gccccgaagt tccaggacaa ggtcaccatg actgtgaca catcctccaa cacagcctgc   240
ctgcacctca gcagcctgac atctgatgac actgccgtct attactgtaa tgtactaggc   300
tacggtaatt acggacattt ttactatgct atggactact ggggtcaagg aacctcagtc   360
accgtctcct ct                                                       372

<210> SEQ ID NO 46
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Gln Gln Ser Gly Thr Glu Leu Val Arg Ser Gly Ala
1               5                   10                  15

Ser Val Lys Leu Ser Cys Thr Thr Ser Gly Phe Asn Ile Lys Asp Tyr
            20                  25                  30

Phe Leu His Trp Val Lys Gln Arg Pro Glu Gln Gly Leu Glu Trp Ile
        35                  40                  45

Gly Trp Ile Asp Pro Glu Asn Gly Asp Thr Lys Tyr Ala Pro Lys Phe
    50                  55                  60

Gln Asp Lys Val Thr Met Thr Val Asp Thr Ser Ser Asn Thr Ala Cys
65                  70                  75                  80

Leu His Leu Ser Ser Leu Thr Ser Asp Asp Thr Ala Val Tyr Tyr Cys
                85                  90                  95

Asn Val Leu Gly Tyr Gly Asn Tyr Gly His Phe Tyr Tyr Ala Met Asp
            100                 105                 110

Tyr Trp Gly Gln Gly Thr Ser Val Thr Val Ser Ser
        115                 120

<210> SEQ ID NO 47
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gatgttgtga tgacccaaac tccactctcc ctgcctgtca gtcttggaga tcaggcctcc    60

```
atctcttgca gatctagtca gagccttgta cacagtaatg aaacaccta tttacattgg    120 tacctgcaga agccaggcca gtctccaaag ctcctgatct acaaagtttc caaccgattt    180
tctggggtcc cagacaggtt cagtggcagt gaatcaggga cagatttcac actcaagatc    240
agcagagtgg aggctgagga tctgggaatt tatttctgct ctcaaaatac acatgttcct    300
cggacgttcg gtggaggcac caagctggaa atcaga                             336
```

```
<210> SEQ ID NO 48
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48
```

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Glu Ser Gly Thr Asp Phe Thr Leu Lys Ile
65                  70                  75                  80

Ser Arg Val Glu Ala Glu Asp Leu Gly Ile Tyr Phe Cys Ser Gln Asn
                85                  90                  95

Thr His Val Pro Arg Thr Phe Gly Gly Gly Thr Lys Leu Glu Ile Arg
            100                 105                 110

```
<210> SEQ ID NO 49
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gaagtgaagc tggtggagtc tgggggaggc ttagtgcagc ctggagggtc cctgaaactc    60
tcctgtgcaa cctctggatt cactttcagt gactattaca tgtattgggt tcgccagact    120
ccagagaaga ggctggagtg ggtcgcatac attagtaatg gtggtggttc cacctattat    180
ccagacactg tgaagggccg attcaccatc tccagagaca tgccaagaa caccctgtac    240 ctgcaaatga gccgtctgaa gtctgaggac acagccatgt attactgtgc aagacatagg    300
ggctctcttg acttctgggg ccaaggcacc actctcacag tctcctca               348
```

```
<210> SEQ ID NO 50
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50
```

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Ser Thr Tyr Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Ser Arg Leu Lys Ser Glu Asp Thr Ala Met Tyr Tyr Cys
                85                  90                  95

Ala Arg His Arg Gly Ser Leu Asp Phe Trp Gly Gln Gly Thr Thr Leu
            100                 105                 110

Thr Val Ser Ser
        115

<210> SEQ ID NO 51
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gacatagtgc tgacacagtc tcctgcttcc ttagctgtat ctctggggca gagggccacc     60
atctcctgca gagccagcga aagtgttgat aattatggct ttagtttat gcactggtac    120 cagcagaaac aggacagcc acccaaactc ctcatctatc gtgcatccaa cctagaatct    180
gggatccctg ccaggttcag tgcagttgg tctaggacag acttcaccct caccattaat    240
cctgtggaga ctgatgatgt tgcaacctat tactgtcagc aaagtaataa ggttccgctc    300
acgttcggtg ctgggaccaa gctggagctg aaa                               333

<210> SEQ ID NO 52
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Val Asp Asn Tyr
            20                  25                  30

Gly Phe Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
 50                  55                  60

Arg Phe Ser Gly Ser Trp Ser Arg Thr Asp Phe Thr Leu Thr Ile Asn
 65                  70                  75                  80

Pro Val Glu Thr Asp Asp Val Ala Thr Tyr Tyr Cys Gln Gln Ser Asn
                85                  90                  95

Lys Val Pro Leu Thr Phe Gly Ala Gly Thr Lys Leu Glu Leu Lys
            100                 105                 110

<210> SEQ ID NO 53

```
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gaggtccagc tgcaacagtc tggacctgag ctggtgaagc ctggagcttc aatgaagata      60
tcctgcaagg cttctggtta ctcattcact ggctacaaca tgaactgggt gaagcagacc     120
catggaaaga accttgagtg gattggactt attaatcctt acaatggtgg tactaggtac     180
aaccagaagt tcaagggcaa ggccacatta actgtagaca gtcatccag cacagcctac      240 atggagctcc tcagtctgac atctgaggac tctgcagtct atttctgtgc aaggatggga     300
cttggaaatg ctatggacta ctggggtcaa ggaacctcag tcaccgtctc ctca           354

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Asn Met Asn Trp Val Lys Gln Thr His Gly Lys Asn Leu Glu Trp Ile
        35                  40                  45

Gly Leu Ile Asn Pro Tyr Asn Gly Gly Thr Arg Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Phe Cys
                85                  90                  95

Ala Arg Met Gly Leu Gly Asn Ala Met Asp Tyr Trp Gly Gln Gly Thr
            100                 105                 110

Ser Val Thr Val Ser Ser
        115

<210> SEQ ID NO 55
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gacattgtga tgacacagtc tccatcctcc ctgactgtga cagcaggaga gaaggtcact      60
atgagctgca gtccagtca gaatctgtta acagtggaa atcaaaagaa ctacttgacc      120
tggtaccagc agaaaccagg gcagcctcct aaactgttga tctactgggc atccactatg     180
gaatctgggg tccctgatcg cttcacaggc agtggatctg gaacagattt cactctcacc     240
atcagcagtg tgcaggctga agacctggca gtttattact gtcagaatga ttatatttat     300
ccgctcccgt tcggtgctgg gaccaagctg gagctgaaa                            339
```

<210> SEQ ID NO 56
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Val Met Thr Gln Ser Pro Ser Ser Leu Thr Val Thr Ala Gly
1               5                   10                  15

Glu Lys Val Thr Met Ser Cys Lys Ser Ser Gln Asn Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Met Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ile Tyr Pro Leu Pro Phe Gly Ala Gly Thr Lys Leu Glu Leu
            100                 105                 110

Lys

<210> SEQ ID NO 57
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggtgcagc tgaaggagtc aggacctggc ctggtggcgc cctcacagag cctgtccatc        60
acatgcacca tctcagggtt ctcattaacc agctatggta tacactgggt tcgccagcct       120
ccaggaaagg gtctggagtg gctggtagtg atatggagtg atggaagaac aacctataat       180
tcagctctca aatccagact gagcatcagc aaggacaact ccaagagcca gttttctta        240 aaaatgaaca gtctccaaac tgatgacaca gccatgtact actgtgccag acatggtaga       300
tacgacccct atgctatgga ctactggggt caaggaacct cagtcaccgt ctcctca         357

<210> SEQ ID NO 58
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Ser Tyr
            20                  25                  30

Gly Ile His Trp Val Arg Gln Pro Pro Gly Lys Gly Leu Glu Trp Leu
        35                  40                  45

Val Val Ile Trp Ser Asp Gly Arg Thr Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Thr Ala Met Tyr Tyr Cys Ala
            85                  90                  95

Arg His Gly Arg Tyr Asp Pro Tyr Ala Met Asp Tyr Trp Gly Gln Gly
            100                 105                 110

Thr Ser Val Thr Val Ser Ser
        115

<210> SEQ ID NO 59
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gacattgtgc tgacccaatc tccagcttct ttggctgtgt ctctagggca gagggccacc      60
atctcctgca gagccagcga gagtgtggat aactatggct tagttttct gcactggtac     120 cagcagaaac aggacagcc acccaaactc ctcatctatc gtgcatccaa cctagcatct     180
gggatccctg ccaggttcag tggcagtggg tctaggacag acttcaccct caccattaat     240
cctgtggaga ctgatgatgt tgcaacctat tactgtcagc aaagtaatca gggtccactc     300
acgttcggtg ctgggaccaa gctggagctg aaa                                  333

<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Phe Ser Phe Leu His Trp Tyr Gln Gln Lys Pro Gly Gln Pro Pro
        35                  40                  45

Lys Leu Leu Ile Tyr Arg Ala Ser Asn Leu Ala Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
            85                  90                  95

Gln Gly Pro Leu Thr Phe Gly Ala Gly Thr Lys Leu Glu Leu Lys
            100                 105                 110

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Asn Met Asn Trp Val Lys Gln Thr His Gly Lys Asn Leu Glu Trp Ile
        35                  40                  45

Gly Leu Ile Asn Pro Tyr Asn Gly Gly Thr Arg Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Phe Cys
                85                  90                  95

Ala Arg Met Gly Leu Gly Asn Ala Met Asp Tyr Trp Gly Gln Gly Thr
            100                 105                 110

Ser Val Thr Val Ser Ser
            115

<210> SEQ ID NO 62
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
            20                  25                  30

Asn Met Asn Trp Val Arg Gln Met Pro Gly Lys Gly Leu Glu Trp Met
        35                  40                  45

Gly Leu Ile Asn Pro Tyr Asn Gly Gly Thr Arg Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Met Gly Leu Gly Asn Ala Met Asp Tyr Trp Gly Gln Gly Thr
            100                 105                 110

Thr Val Thr Val Ser Ser
            115

<210> SEQ ID NO 63
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
            20                  25                  30

Asn Met Asn Trp Val Arg Gln Met Pro Gly Lys Asn Leu Glu Trp Ile
        35                  40                  45

Gly Leu Ile Asn Pro Tyr Asn Gly Gly Thr Arg Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Met Gly Leu Gly Asn Ala Met Asp Tyr Trp Gly Gln Gly Thr
            100                 105                 110

Thr Val Thr Val Ser Ser
        115

<210> SEQ ID NO 64
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
                20                  25                  30

Asn Met Asn Trp Val Arg Gln Met Pro Gly Lys Asn Leu Glu Trp Ile
            35                  40                  45

Gly Leu Ile Asn Pro Tyr Asn Gly Gly Thr Arg Tyr Asn Gln Lys Phe
    50                  55                  60

Lys Gly Lys Ala Thr Leu Ser Val Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Met Gly Leu Gly Asn Ala Met Asp Tyr Trp Gly Gln Gly Thr
            100                 105                 110

Thr Val Thr Val Ser Ser
        115

<210> SEQ ID NO 65
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Val Met Thr Gln Ser Pro Ser Ser Leu Thr Val Thr Ala Gly
1               5                   10                  15

Glu Lys Val Thr Met Ser Cys Lys Ser Ser Gln Asn Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Met Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

```
Asp Tyr Ile Tyr Pro Leu Pro Phe Gly Ala Gly Thr Lys Leu Glu Leu
            100                 105                 110

Lys

<210> SEQ ID NO 66
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Met Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ile Tyr Pro Leu Pro Phe Gly Gln Gly Thr Lys Leu Glu Ile
            100                 105                 110

Lys

<210> SEQ ID NO 67
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Leu Leu Gln Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ile Tyr Pro Leu Pro Phe Gly Gln Gly Thr Lys Leu Glu Ile
            100                 105                 110

Lys

<210> SEQ ID NO 68
<211> LENGTH: 354
<212> TYPE: DNA
<213> ORGANISM: Artificial Sequence
<220> FEATURE:
```

<223> OTHER INFORMATION: Description of Artificial Sequence: Synthetic
     polynucleotide

<400> SEQUENCE: 68

```
gaggtccagc tgcaacagtc tggacctgag ctggtgaagc ctggagcttc aatgaagata      60
tcctgcaagg cttctggtta ctcattcact ggctacaaca tgaactgggt gaagcagacc     120
catggaaaga accttgagtg gattggactt attaatcctt acaatggtgg tactaggtac     180
aaccagaagt tcaagggcaa ggccacatta actgtagaca agtcatccag cacagcctac     240
atggagctcc tcagtctgac atctgaggac tctgcagtct atttctgtgc aaggatggga     300
cttggaaatg ctatggacta ctggggtcaa ggaacctcag tcaccgtctc ctca           354
```

<210> SEQ ID NO 69
<211> LENGTH: 354
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 69

```
gaagtccagc tcgtgcagtc tggtgcggag gtcaaaaaac ccggcgagtc tctcaaaatt      60
agttgcaaag gctccggtta ttcattcacg ggttacaata tgaactgggt tcgacaaatg     120
ccgggtaagg gacttgaatg gatgggattg atcaacccct ataacggagg taccagatac     180
aaccaaaaat ttaagggcca ggtgactatt agtgcagata aagtatctc caccgcttac      240
ctccaatggt ctagtttgaa ggcgtctgac actgctatgt acttttgcgc gagaatgggg     300
ttgggaaatg cgatggacta ctggggtcag ggcactacgg ttacggtctc ctct           354
```

<210> SEQ ID NO 70
<211> LENGTH: 354
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 70

```
gaggtacagc tcgtgcaatc tggggccgaa gtaaagaaac ctggagaaag tcttaaaata      60
agctgcaagg gcagtgggta tagcttcacg ggctacaata tgaactgggt tagacaaatg     120
ccaggtaaga acctcgaatg gataggattg atcaacccat acaatggtgg tacgcgctac     180
aaccagaaat tcaaaggtca ggttaccatc tctgcggata aaagcatctc aacggcgtat     240
cttcaatggt cctcactgaa agcatccgac acagcaatgt attttttgcgc tagaatggga    300
ttgggtaatg ccatggacta ctggggccaa ggcaccacgg ttacagtctc ttcc           354
```

<210> SEQ ID NO 71
<211> LENGTH: 354
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 71

```
gaagttcagc tggtgcaaag tggggctgag gtaaagaagc ctggcgagag cctcaagatt      60
tcttgcaagg gtagcggata cagttttacg ggatataaca tgaattgggt tcgccagatg     120
ccggggaaga accttgaatg gataggactg ataaaccct ataatggggg aacccgatat      180
```

```
aatcagaagt ttaagggaaa agcaactttg tcagttgaca agtctatcag cacggcctat    240
cttcagtggt ccagtctgaa agcaagcgac acggctatgt acttttgtgc acgcatgggg    300
cttggtaacg caatggacta ttggggacaa ggaactaccg tcactgtctc ttca          354
```

<210> SEQ ID NO 72
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
gacattgtga tgacacagtc tccatcctcc ctgactgtga cagcaggaga gaaggtcact    60
atgagctgca agtccagtca gaatctgtta aacagtggaa atcaaaagaa ctacttgacc    120
tggtaccagc agaaaccagg gcagcctcct aaactgttga tctactgggc atccactatg    180
gaatctgggg tccctgatcg cttcacaggc agtggatctg gaacagattt cactctcacc    240
atcagcagtg tgcaggctga agacctggca gtttattact gtcagaatga ttatatttat    300
ccgctcccgt tcggtgctgg gaccaagctg gagctgaaa                          339
```

<210> SEQ ID NO 73
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
gacatcgtga tgacccagtc cccggacagt ctggcagtca gtcttgggga aagagctacc    60
ataaactgca atccagcca aaaccttctt aatagcggca accaaaagaa ttacttgact     120
tggtatcagc aaaaaccggg tcagccgccc aaactcttga tatactgggc gtctacgatg    180
gaaagcggcg tccccgaccg cttcagcggg agtgggtcag ggactgattt cactttgaca    240
atcagttccc ttcaggcaga ggacgtagca gtctactact gtcagaatga ttatatatat    300
cctcttccgt tcggccaggg gacgaagttg gagatcaaa                          339
```

<210> SEQ ID NO 74
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
gacatcgtga tgactcaaag tcctgactcc cttgctgttt cacttggcga aagggccact    60
atcaactgta agagttctca gaatctcttg caatcaggaa accagaagaa ttacttgacc    120
tggtatcaac agaagcctgg acaaccacct aagctcttga tttactgggc tagtacaagg    180
gagtccggcg tcccagacag attttccggt tctggatcag gcacggactt cactctgaca    240
atctctagtc ttcaagccga ggatgtggcc gtttattatt gccagaacga ttacatttac    300
cctttgccat ttggtcaagg tactaagttg gagataaaa                          339
```

<210> SEQ ID NO 75
<211> LENGTH: 48

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctcgagccca aatcttgtga caaaactcac acatgcccac cgtgcccg                   48

<210> SEQ ID NO 76
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76 tttttgggtgc tggtggtggt tggtggagtc ctggcttgct atagcttgct agtaacagtg    60
gcctttatta ttttctgggt g                                               81

<210> SEQ ID NO 77
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 78
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 79
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
```

```
tacgacgccc ttcacatgca ggccctgccc cctcgctaa              339
```

\<210\> SEQ ID NO 80
\<211\> LENGTH: 51
\<212\> TYPE: PRT
\<213\> ORGANISM: Homo sapiens

\<400\> SEQUENCE: 80

```
Pro Ala Lys Pro Thr Thr Thr Pro Ala Pro Arg Pro Pro Thr Pro Ala
1               5                   10                  15

Pro Thr Ile Ala Ser Gln Pro Leu Ser Leu Arg Pro Glu Ala Cys Arg
            20                  25                  30

Pro Ala Ala Gly Gly Ala Val His Thr Arg Gly Leu Asp Phe Ala Cys
        35                  40                  45

Asp Ile Tyr
    50
```

\<210\> SEQ ID NO 81
\<211\> LENGTH: 49
\<212\> TYPE: PRT
\<213\> ORGANISM: Mus sp.

\<400\> SEQUENCE: 81

```
Lys Val Asn Ser Thr Thr Thr Lys Pro Val Leu Arg Thr Pro Ser Pro
1               5                   10                  15

Val His Pro Thr Gly Thr Ser Gln Pro Gln Arg Pro Glu Asp Cys Arg
            20                  25                  30

Pro Arg Gly Ser Val Lys Gly Thr Gly Leu Asp Phe Ala Cys Asp Ile
        35                  40                  45

Tyr
```

\<210\> SEQ ID NO 82
\<211\> LENGTH: 51
\<212\> TYPE: PRT
\<213\> ORGANISM: Felis catus

\<400\> SEQUENCE: 82

```
Pro Val Lys Pro Thr Thr Thr Pro Ala Pro Arg Pro Pro Thr Gln Ala
1               5                   10                  15

Pro Ile Thr Thr Ser Gln Arg Val Ser Leu Arg Pro Gly Thr Cys Gln
            20                  25                  30

Pro Ser Ala Gly Ser Thr Val Glu Ala Ser Gly Leu Asp Leu Ser Cys
        35                  40                  45

Asp Ile Tyr
    50
```

\<210\> SEQ ID NO 83
\<211\> LENGTH: 21
\<212\> TYPE: PRT
\<213\> ORGANISM: Homo sapiens

\<400\> SEQUENCE: 83

```
Ile Tyr Ile Trp Ala Pro Leu Ala Gly Thr Cys Gly Val Leu Leu Leu
1               5                   10                  15

Ser Leu Val Ile Thr
            20
```

\<210\> SEQ ID NO 84
\<211\> LENGTH: 21

```
<212> TYPE: PRT
<213> ORGANISM: Mus sp.

<400> SEQUENCE: 84

Ile Trp Ala Pro Leu Ala Gly Ile Cys Val Ala Leu Leu Ser Leu
1               5                   10                  15

Ile Ile Thr Leu Ile
            20

<210> SEQ ID NO 85
<211> LENGTH: 21
<212> TYPE: PRT
<213> ORGANISM: Rattus sp.

<400> SEQUENCE: 85

Ile Trp Ala Pro Leu Ala Gly Ile Cys Ala Val Leu Leu Ser Leu
1               5                   10                  15

Val Ile Thr Leu Ile
            20

<210> SEQ ID NO 86
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 87
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
            115                 120                 125
```

```
Asn Gly Thr Ile Ile His Val Lys Gly Lys His Leu Cys Pro Ser Pro
            130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
210                 215                 220

<210> SEQ ID NO 88
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
acaaaaaaga agtattcatc cagtgtgcac gaccctaacg gtgaatacat gttcatgaga    60
gcagtgaaca cagccaaaaa atccagactc acagatgtga cccta                  105

<210> SEQ ID NO 89
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
agggaccaga ggctgccccc cgatgcccac aagccccctg ggggaggcag tttccggacc    60
cccatccaag aggagcaggc cgacgcccac tccaccctgg ccaagatc               108

<210> SEQ ID NO 90
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
```

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Gly Gly Ser Gly Gly Gly Ser Gly Gly Gly Gly Ser
1               5                   10                  15

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Gly Gly Gly Ser
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Tyr Asn Met Asn
1               5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu Ile Asn Pro Tyr Asn Gly Gly Thr Arg Tyr Asn Gln Lys Phe Lys
1               5                   10                  15

Gly

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Arg Gly Gly Asn Ile Tyr Asp Gly Tyr Pro Tyr Tyr Phe Asp Tyr
1               5                   10                  15

<210> SEQ ID NO 96
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 96

Met Gly Leu Gly Asn Ala Met Asp Tyr
1               5

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Ser Ser Gln Asn Leu Leu Asn Ser Gly Asn Gln Lys Asn Tyr Leu
1               5                   10                  15

Thr

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Ala Ser Thr Met Glu Ser
1               5

<210> SEQ ID NO 99
<211> LENGTH: 384
<212> TYPE: PRT
<213> ORGANISM: Homo sapiens

<400> SEQUENCE: 99

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
            35                  40                  45

Gln Pro Gln Arg Thr Phe Pro Glu Ile Gln Arg Arg Asp Ser Tyr Tyr
        50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175
```

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
            195                 200                 205

Lys Val Pro Thr Gly Val Glu Glu Gly Leu Leu Glu Arg His Ser
            210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
            245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Glu Ala
            275                 280                 285

Ala Ser Trp Leu Leu Cys Glu Val Ser Gly Phe Ser Pro Pro Asn Ile
            290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
            325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
            370                 375                 380

<210> SEQ ID NO 100
<211> LENGTH: 330
<212> TYPE: PRT
<213> ORGANISM: Homo sapiens

<400> SEQUENCE: 100

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu

```
                   165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 101
<211> LENGTH: 326
<212> TYPE: PRT
<213> ORGANISM: Homo sapiens

<400> SEQUENCE: 101

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
        100                 105                 110

Pro Val Ala Gly Pro Ser Val Phe Leu Phe Pro Pro Lys Pro Lys Asp
    115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
    195                 200                 205
```

```
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 102
<211> LENGTH: 377
<212> TYPE: PRT
<213> ORGANISM: Homo sapiens

<400> SEQUENCE: 102

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255
```

```
Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 103
<211> LENGTH: 452
<212> TYPE: PRT
<213> ORGANISM: Homo sapiens

<400> SEQUENCE: 103

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
```

```
            245                 250                 255
Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
            275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
            435                 440                 445

Gly Thr Cys Tyr
450

<210> SEQ ID NO 104
<211> LENGTH: 327
<212> TYPE: PRT
<213> ORGANISM: Homo sapiens

<400> SEQUENCE: 104

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 105
<211> LENGTH: 353
<212> TYPE: PRT
<213> ORGANISM: Homo sapiens

<400> SEQUENCE: 105

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205
```

```
Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225             230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
                260                 265                 270

Arg Glu Lys Tyr Leu Thr Trp Ala Ser Arg Gln Glu Pro Ser Gln Gly
            275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr

<210> SEQ ID NO 106
<211> LENGTH: 340
<212> TYPE: PRT
<213> ORGANISM: Homo sapiens

<400> SEQUENCE: 106

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
                20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Pro Asp Gly
65              70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
                100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
                180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
    210                 215                 220
```

```
Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
                260                 265                 270

Ser Gln Gly Thr Thr Thr Phe Ala Val Thr Ser Ile Leu Arg Val Ala
                275                 280                 285

Ala Glu Asp Trp Lys Lys Gly Asp Thr Phe Ser Cys Met Val Gly His
        290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
                340

<210> SEQ ID NO 107
<211> LENGTH: 106
<212> TYPE: PRT
<213> ORGANISM: Homo sapiens

<400> SEQUENCE: 107

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105
```

CLDN 18.2-SPECIFIC MONOCLONAL ANTIBODIES AND METHODS OF USE THEREOF

CROSS-REFERENCE TO RELATED APPLICATION

This application claims is a national stage entry under U.S.C. § 371 of International Application No. PCT/US2019/043316, filed Jul. 24, 2019, which in turn priority under 35 U.S.C. § 119(e) of U.S. provisional application Ser. No. 62/703,036, filed Jul. 25, 2018, the content of each of which is hereby incorporated by reference into the present disclosure.

SEQUENCE LISTING

The instant application contains a Sequence Listing which has been submitted electronically in ASCII format and is hereby incorporated by reference in its entirety. Said ASCII copy, created on Jan. 13, 2021, is named 119163-0123_SL.txt and is 78,641 bytes in size.

TECHNICAL FIELD

This disclosure relates to novel CLDN 18.2 antibodies and chimeric antigen receptors (CAR) derived therefrom, cells or compositions comprising the same, and methods for using the same for therapy including the treatment of solid tumors.

BACKGROUND

Isoform 2 of claudin-18 (CLDN 18.2), a tight junction molecule, is known to be a selective lineage marker. It has been observed to be expressed in a significant proportion of primary gastric cancers and metastases. Extopic activation has also been seen in pancreatic, esophageal, ovarian, and lung tumors. While it has a highly restricted expression in normal tissues, CLDN 18.2 is ectopically activated in a diversity of cancers. See Sahin et al., Claudin-18 splice variant 2 is a pan-cancer target suitable for therapeutic antibody development, *Clin. Cancer Res.* 2008; 14(23): 7624-34. Accordingly, antibodies against this isoform are useful in the treatment of treatment of gastrointestinal (GI) tumors, such as gastric, pancreatic, esophageal, ovarian, and lung tumors (e.g., IMAB362 (claudiximab, developed by Ganymed Pharmaceuticals AG)).

SUMMARY OF THE DISCLOSURE

This disclosure provides a novel antibody to CLDN 18.2 and compositions and methods of use thereof. More specifically, this disclosure provides a new anti-CLDN 18.2 antibodies for the treatment of tumors expressing CLDN 18.2, such as for example, GI tumors that include, but are not limited to, gastric, pancreatic, esophageal, biliary tract, colorectal, colon, rectal, ovarian, and lung carcinomas. The target, CLDN 18.2, is highly expressed on the majority of these tumors but has restricted off-target positivity and therefore a desirable safety profile. Thus, in one aspect, the compositions are particularly useful in the treatment of tumors or cancerous cell that express or overexpress CLDN 18.2.

In one aspect, the present disclosure provides isolated antibodies, the antibodies comprising a heavy chain (HC) immunoglobulin variable domain sequence and a light chain (LC) immunoglobulin variable domain sequence, wherein the antibodies bind to an epitope of CLDN 18.2. In one aspect, the antibodies bind to an epitope of CLDN 18.2, but not CLDN 18.1. In one aspect, the antibody is a humanized antibody comprising one or more, two or more, three or more, four or more, five or more, six or more, seven or more or all eight of the CDRs identified in Table 3, with the antibodies disclosed in Table 4. In another aspect, the antibodies bind with high specificity, that is they bind to CLDN 18.2 with an affinity of more than 80%, or alternatively more than 85%, or alternatively more than 90%, or alternatively more than 95%, binding for CLDN 18.2-expressing cells versus less than 20%, or alternatively less than 15%, or alternatively less than 10%, or alternatively less than 5% binding to CLDN 18.1. Examples of such are shown in FIGS. 1a, 1b and 9. There, the antibodies are more specific for the CLDN 18.2 expressing tumor cells and would have lower toxicity since they do not bind to the CLDN 18.1-expressing normal cells.

In some embodiments, the antibody is a bispecific antibody has a binding specificity to a second target protein. The second target protein, in some embodiments, is selected from the group consisting of IL-1, CD3, CD16, CD19, CD28, CD47, CD64, PD-1, PD-L1, CTLA-4, LAG-3, CD28, CD122, 4-1BB, TIM3, OX-40, OX40L, CD40, CD40L, LIGHT, ICOS, ICOSL, GITR, GITRL, TIGIT, CD27, VISTA, B7H3, B7H4, HEVM, BTLA and KIR. In some embodiments, the antibody is comprised in an antibody drug conjugates (ADC) formed between the antibody and another agent, such as toxin or drug. In some embodiments, the antibodies may be conjugated to therapeutic agents, prodrugs, peptides, proteins, enzymes, viruses, lipids, biological response modifiers, pharmaceutical agents, and/or polyethylene glycol (PEG).

In a further aspect, this disclosure provides isolated anti-CLDN 18.2 antibodies or fragments thereof as disclosed herein and a detectable or purification label, alone or in combination with an CLDN 18.2 antigen or fragment (e.g., VH1, VH2, VH3, VL1, VL2, VL3, heavy and light chain CDR1, CDR2, CDR3) thereof, that in one aspect are bound to each other to form a antigen/antibody complex. Further provided herein is an ex vivo cell comprising this antigen/antibody complex.

Aspects of the disclosure relate to a chimeric antigen receptor (CAR) comprising: (a) an antigen binding domain of a CLDN 18.2 antibody (e.g., VH1, VH2, VH3, VL1, VL2, VL3, heavy and light chain CDR1, CDR2, CDR3); (b) a hinge domain; (c) a transmembrane domain; and (d) an intracellular domain. Further aspects of the disclosure relate to a chimeric antigen receptor (CAR) comprising: (a) an antigen binding domain of a CLDN 18.2 antibody (e.g., VH1, VH2, VH3, VL1, VL2, VL3, heavy and light chain CDR 1, CDR2, CDR3); (b) a hinge domain; (c) a CD28 transmembrane domain; (d) one or more costimulatory regions selected from a CD28 costimulatory signaling region, a 4-1BB costimulatory signaling region, an ICOS costimulatory signaling region, and an OX40 costimulatory region; and (e) a CD3 zeta signaling domain and alternatives thereof.

In a further aspect, the present disclosure provides a chimeric antigen receptor (CAR) comprising: (a) an antigen binding domain of an anti-CLDN 18.2 antibody (e.g., VH1, VH2, VH3, VL1, VL2, VL3, heavy and light chain CDR1, CDR2, CDR3), (b) a CD8α hinge domain; (c) a CD8α transmembrane domain; (d) a CD28 and/or a 4-1BB costimulatory signaling region; and (e) a CD3 zeta signaling domain and alternatives thereof.

In another aspect, the present disclosure provides an isolated nucleic acid sequence encoding the anti-CLDN 18.2 antibody, chimeric antibody, humanized antibody, bispecific antibody, or the anti-CLDN 18.2 CAR.

In another aspect, the present disclosure provides a vector comprising the isolated nucleic acid sequence encoding the anti-CLDN 18.2 antibody, chimeric antibody, bispecific antibody, humanized antibody, or the anti-CLDN 18.2 CAR.

In another aspect, the present disclosure provides a vector comprising the isolated nucleic acid sequence encoding the anti-CLDN 18.2 antibody, chimeric antibody, bispecific antibody, humanized antibody, or the anti-CLDN 18.2 CAR.

In another aspect, the present disclosure provides a composition comprising a carrier and one or more of: the anti-CLDN 18.2 antibody; and/or the bispecific antibody; and/or the chimeric antibody; and/or the humanized antibody; and/or the anti-CLDN 18.2 CAR; and/or the isolated nucleic acid encoding the anti-CLDN 18.2 antibody bispecific antibody, chimeric antibody, humanized antibody, or the anti-CLDN 18.2 CAR; and/or the vector comprising the isolated nucleic acid sequence encoding the anti-CLDN 18.2 antibody, bispecific antibody, chimeric antibody, humanized antibody, or the anti-CLDN 18.2 CAR; and/or an isolated cell comprising the anti-CLDN 18.2 CAR.

In one aspect, the disclosure provides a composition comprising, or alternatively consisting essentially of, or yet further consisting of a carrier and one or more of: an antibody or fragment (e.g., VH1, VH2, VH3, VL1, VL2, VL3, heavy and light chain CDR 1, CDR2, CDR3) thereof, a nucleic acid encoding the antibody or fragment (e.g., VH1, VH2, VH3, VL1, VL2, VL3, heavy and light chain CDR1, CDR2, CDR3) thereof, a vector comprising the nucleic acid encoding the antibody or fragment (e.g., VH1, VH2, VH3, VL1, VL2, VL3, heavy and light chain CDR1, CDR2, CDR3) thereof, an isolated cell comprising an anti-CLDN 18.2 CAR and/or a polynucleotide encoding the antibody or fragment (e.g., VH1, VH2, VH3, VL1, VL2, VL3, heavy and light chain CDR1, CDR2, CDR3) thereof; and/or the isolated nucleic acid encoding the CAR; and/or the vector comprising the nucleic acid encoding the CAR; and/or the isolated cell expressing an anti-CLDN 18.2 CAR; and/or the anti-CLDN 18.2 antibody; and/or bispecific antibody; and/or humanized antibody.

Compositions are also provided. In one embodiment, the composition comprises an antibody or fragment (e.g., VH1, VH2, VH3, VL1, VL2, VL3, heavy and light chain CDR 1, CDR2, CDR3) thereof, a fusion protein, or a CAR and/or car expressing-cell of the present disclosure and a pharmaceutically acceptable carrier. Also provided is an isolated cell comprising one or more polynucleotide encoding the antibody or fragment (e.g., VH1, VH2, VH3, VL1, VL2, VL3, heavy and light chain CDR1, CDR2, CDR3) thereof or the fusion protein or bispecific antibody of the present disclosure.

The present disclosure further provides a method of treating tumor or growth expressing CLDN 18.2 antigen, such as for example cancer in a patient in need thereof, comprising administering to the patient a antibody or fragment (e.g., VH1, VH2, VH3, VL1, VL2, VL3, heavy and light chain CDR1, CDR2, CDR3) thereof, a fusion protein, or a CAR and/or car expressing-cell of the present disclosure. Non-limiting examples of cancers include GI cancers, bladder cancer, liver cancer, colon cancer, rectal cancer, colorectal cancer, endometrial cancer, biliary cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer.

DETAILED DESCRIPTION

Figure 1A:
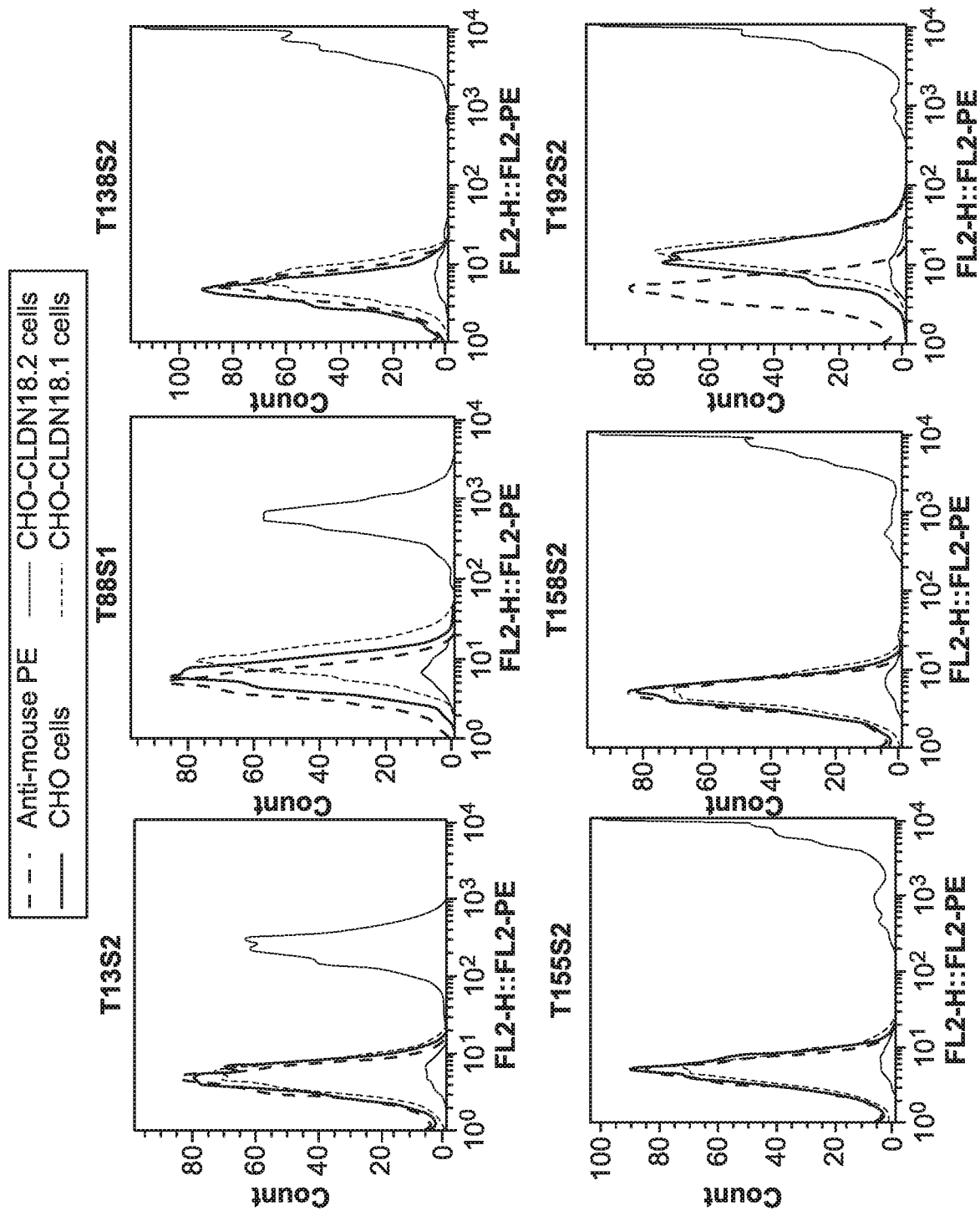
FIG. 1A-1B show the binding specificity of anti-CLDN 18.2 hybridoma antibodies. CHO stable cell lines expressing either human CLDN 18.1 or human CLDN 18.2 were used in the FACS analysis. All anti-CLDN 18.2 hybridoma antibodies were used at 10 µg/ml.

It is to be understood that the present disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims.

Unless defined otherwise, all technical and scientific terms used herein have the same meanings as commonly understood by one of ordinary skill in the art to which this technology belongs. Although any methods and materials similar or equivalent to those described herein can be used in the practice or testing of the present technology, the preferred methods, devices and materials are now described. All technical and patent publications cited herein are incorporated herein by reference in their entirety. Nothing herein is to be construed as an admission that the present technology is not entitled to antedate such disclosure by virtue of prior invention.

The practice of the present technology will employ, unless otherwise indicated, conventional techniques of tissue culture, immunology, molecular biology, microbiology, cell biology, and recombinant DNA, which are within the skill of the art. See, e.g., Green and Sambrook eds. (2012) Molecular Cloning: A Laboratory Manual, 4$^{th}$ edition; the series Ausubel et al. eds. (2015) Current Protocols in Molecular Biology; the series Methods in Enzymology (Academic Press, Inc., N.Y.); MacPherson et al. (2015) PCR 1: A Practical Approach (IRL Press at Oxford University Press);

MacPherson et al. (1995) PCR 2: A Practical Approach; McPherson et al. (2006) PCR: The Basics (Garland Science); Harlow and Lane eds. (1999) Antibodies, A Laboratory Manual; Greenfield ed. (2014) Antibodies, A Laboratory Manual; Freshney (2010) Culture of Animal Cells: A Manual of Basic Technique, 6$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Herdewijn ed. (2005) Oligonucleotide Synthesis: Methods and Applications; Hames and Higgins eds. (1984) Transcription and Translation; Buzdin and Lukyanov ed. (2007) Nucleic Acids Hybridization: Modern Applications; Immobilized Cells and Enzymes (IRL Press (1986)); Grandi ed. (2007) *In Vitro Transcription and Translation Protocols*, 2$^{nd}$ edition; Guisan ed. (2006) Immobilization of Enzymes and Cells; Perbal (1988) A Practical Guide to Molecular Cloning, 2$^{nd}$ edition; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Lundblad and Macdonald eds. (2010) Handbook of Biochemistry and Molecular Biology, 4$^{th}$ edition; and Herzenberg et al. eds (1996) Weir's Handbook of Experimental Immunology, 5$^{th}$ edition; and the more recent editions each thereof available at the time of filing.

All numerical designations, fus e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about." It also is to be understood, although not always explicitly stated, that the reagents described herein are merely exemplary and that equivalents of such are known in the art.

It is to be inferred without explicit recitation and unless otherwise intended, that when the present technology relates to a polypeptide, protein, polynucleotide or antibody, an equivalent or a biologically equivalent of such is intended within the scope of the present technology.

Definitions

As used in the specification and claims, the singular form "a", "an", and "the" include plural references unless the context clearly dictates otherwise. For example, the term "a cell" includes a plurality of cells, including mixtures thereof.

As used herein, the term "animal" refers to living multicellular vertebrate organisms, a category that includes, for example, mammals and birds. The term "mammal" includes both human and non-human mammals.

The terms "subject," "host," "individual," and "patient" are as used interchangeably herein to refer to human and veterinary subjects, for example, humans, animals, non-human primates, dogs, cats, sheep, mice, horses, and cows. In some embodiments, the subject is a human.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins.

Unless specifically noted otherwise, the term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3$ M$^{-1}$ greater, at least $10^4$ M$^{-1}$ greater or at least $10^5$ M$^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Owen et al., *Kuby Immunology*, 7$^{th}$ Ed., W. H. Freeman & Co., 2013; Murphy, *Janeway's Immunobiology*, 8$^{th}$ Ed., Garland Science, 2014; Male et al., *Immunology* (Roitt), 8$^{th}$ Ed., Saunders, 2012; Parham, *The Immune System*, 4$^{th}$ Ed., Garland Science, 2014.

In terms of antibody structure, an immunoglobulin has heavy (H) chains and light (L) chains interconnected by disulfide bonds. There are two types of light chain, lambda (k) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopts a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds CLDN 18.2 will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

As used herein, the term "antigen binding domain" refers to any protein or polypeptide domain that can specifically bind to an antigen target.

As used herein, the term "autologous," in reference to cells refers to cells that are isolated and infused back into the same subject (recipient or host). "Allogeneic" refers to non-autologous cells.

As used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes, such as T cells, by the presence of a B-cell receptor on the cell surface. B cells may either be isolated or obtained from a commercially available source. Non-limiting examples of commercially available B cell lines include lines AHH-1 (ATCC® CRL-8146™), BC-1 (ATCC® CRL-2230™), BC-2 (ATCC® CRL-2231™), BC-3 (ATCC® CRL-2277™) CA46 (ATCC® CRL-1648™), DG-75[DG-75] (ATCC® CRL-2625™), DS-1 (ATCC® CRL-11102™), EB-3[EB3] (ATCC® CCL-85™), Z-138 (ATCC #CRL-3001), DB (ATCC CRL-2289), Toledo (ATCC CRL-2631), Pfiffer (ATCC CRL-2632), SR (ATCC CRL-2262), JM-1 (ATCC CRL-10421), NFS-5 C-1 (ATCC CRL-1693); NFS-70 C10 (ATCC CRL-1694), NFS-25 C-3 (ATCC CRL-1695), AND SUP-B15 (ATCC CRL-1929). Further examples include but are not limited to cell lines derived from anaplastic and large cell lymphomas, e.g., DEL, DL-40, FE-PD, JB6, Karpas 299, Ki-JK, Mac-2A Ply1, SR-786, SU-DHL-1, -2, -4, -5, -6, -7, -8, -9, -10, and -16, DOHH-2, NU-DHL-1, U-937, Granda 519, USC-DHL-1, RL; Hodgkin's lymphomas, e.g., DEV, HD-70, HDLM-2, HD-MyZ, HKB-1, KM-H2, L428, L540, L1236, SBH-1, SUP-HD1, SU/RH-HD-1. Non-limiting exemplary sources for such commercially available cell lines include the American Type Culture Collection, or ATCC, (atcc.org/) and the German Collection of Microorganisms and Cell Cultures (dsmz.de/).

As used herein, a "cancer" is a disease state characterized by the presence in a subject of cells demonstrating abnormal uncontrolled replication and in some aspects, the term may be used interchangeably with the term "tumor." The term "cancer or tumor antigen" refers to an antigen known to be associated and expressed on the surface with a cancer cell or tumor cell or tissue, and the term "cancer or tumor targeting antibody" refers to an antibody that targets such an antigen.

The term "chimeric antigen receptor" (CAR), as used herein, refers to a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" or "intracellular signaling domain" means any oligopeptide or polypeptide known to function as a domain that transmits a signal to cause activation or inhibition of a biological process in a cell. In certain embodiments, the intracellular domain may comprise, alternatively consist essentially of, or yet further comprise one or more costimulatory signaling domains in addition to the primary signaling domain. The "transmembrane domain" means any oligopeptide or polypeptide known to span the cell membrane and that can function to link the extracellular and signaling domains. A chimeric antigen receptor may optionally comprise a "hinge domain" which serves as a linker between the extracellular and transmembrane domains. Non limiting examples of polynucleotides encoding such domains are provided herein, e.g.:

Hinge domain: IgG1 heavy chain hinge sequence:

(SEQ ID NO: 75)
CTCGAGCCCAAATCTTGTGACAAAACTCACACATGCCCACCGTGCCCG

Transmembrane domain: CD28 transmembrane region:

(SEQ ID NO: 76)
TTTTGGGTGCTGGTGGTGGTTGGTGGAGTCCTGGCTTGCTATAGCTTG

CTAGTAACAGTGGCCTTTATTATTTTCTGGGTG

Intracellular domain: 4-1BB co-stimulatory signaling region:

(SEQ ID NO: 77)
AAACGGGGCAGAAAGAAACTCCTGTATATATTCAAACAACCATTTATG

AGACCAGTACAAACTACTCAAGAGGAAGATGGCTGTAGCTGCCGATTT

CCAGAAGAAGAAGAAGGAGGATGTGAACTG

Intracellular domain: CD28 co-stimulatory signaling region:

(SEQ ID NO: 78)
AGGAGTAAGAGGAGCAGGCTCCTGCACAGTGACTACATGAACATGACT

CCCCGCCGCCCCGGGCCCACCCGCAAGCATTACCAGCCCTATGCCCCA

CCACGCGACTTCGCAGCCTATCGCTCC

Intracellular domain: CD3 zeta signaling region:

(SEQ ID NO: 79)
AGAGTGAAGTTCAGCAGGAGCGCAGACGCCCCCGCGTACCAGCAGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAA, or equivalents of each thereof.

Further embodiments of each exemplary domain component include other proteins that have analogous biological function that share at least 70%, or alternatively at least 80% amino acid sequence identity, preferably 90% sequence identity, more preferably at least 95% sequence identity with the proteins encoded by the above disclosed nucleic acid sequences. Further, non limiting examples of such domains are provided herein.

As used herein, the term "CD8α hinge domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD8α hinge domain sequence as shown herein. The example sequences of CD8α hinge domain for human, mouse, and other species are provided in Pinto, R. D. et al. (2006) Vet. Immunol. Immunopathol. 110:169-177. The sequences associated with the CD8α hinge domain are provided in Pinto, R. D. et al. (2006) Vet. Immunol. Immunopathol. 110:169-177.

Non-limiting examples of such include:
Human CD8 alpha hinge domain:

(SEQ ID NO: 80)
PAKPTTTPAPRPPTPAPTIASQPLSLRPEACRPAAGGAVHTRGLDFACDIY

Mouse CD8 alpha hinge domain:

(SEQ ID NO: 81)
KVNSTTTKPVLRTPSPVHPTGTSQPQRPEDCRPRGSVKGTGLDFACDIY

Cat CD8 alpha hinge domain:

(SEQ ID NO: 82)
PVKPTTTPAPRPPTQAPITTSQRVSLRPGTCQPSAGSTVEASGLDLSCDIY, and equivalents of each thereof.

As used herein, the term "CD8α transmembrane domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD8α transmembrane domain sequence as shown herein. The fragment sequences associated with the amino acid positions 183 to 203 of the human T-cell surface glycoprotein CD8 alpha chain (GenBank Accession No: NP_001759.3), or the amino acid positions 197 to 217 of the mouse T-cell surface glycoprotein CD8 alpha chain (GenBank Accession No: NP_001074579.1), and the amino acid positions 190 to 210 of the rat T-cell surface glycoprotein CD8 alpha chain (GenBank Accession No: NP_113726.1) provide additional example sequences of the CD8α transmembrane domain. The sequences associated with each of the listed accession numbers are provided as follows:

Human CD8 alpha transmembrane domain: IYIWAPLAGTCGVLLLSLVIT (SEQ ID NO: 83)
Mouse CD8 alpha transmembrane domain: IWAPLAGICVALLLSLIITLI (SEQ ID NO: 84)
Rat CD8 alpha transmembrane domain: IWAPLAGICAVLLLSLVITLI (SEQ ID NO: 85), and equivalents of each thereof.

As used herein, the term "CD28 transmembrane domain" refers to a specific protein fragment associated with this name and any other molecules that have analogous biological function that share at least 70%, or alternatively at least 80% amino acid sequence identity, at least 90% sequence identity, or alternatively at least 95% sequence identity with the CD28 transmembrane domain sequence as shown herein. The fragment sequences associated with the GenBank Accession Nos: XM_006712862.2 and XM_009444056.1 provide additional, non-limiting, example sequences of the CD28 transmembrane domain. The sequences associated with each of the listed accession numbers are provided herein.

As used herein, the term "4-1BB costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the 4-1BB costimulatory signaling region sequence as shown herein. Non-limiting example sequences of the 4-1BB costimulatory signaling region are provided in U.S. Publication 20130266551A1 (filed as U.S. application Ser. No. 13/826,258), such as the exemplary sequence provided below:

4-1BB costimulatory signaling region:
KRGRKKLLY-
IFKQPFMRPVQTTQEEDGCSCRFPEEEEGGCEL
(SEQ ID NO: 86), and an equivalent thereof.

As used herein, the term "CD28 costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the CD28 costimulatory signaling region sequence shown herein. The example sequences CD28 costimulatory signaling domain are provided in U.S. Pat. No. 5,686,281; Geiger, T. L. et al., Blood 98: 2364-2371 (2001); Hombach, A. et al., J Immunol 167: 6123-6131 (2001); Maher, J. et al. Nat Biotechnol 20: 70-75 (2002); Haynes, N. M. et al., J Immunol 169: 5780-5786 (2002); Haynes, N. M. et al., Blood 100: 3155-3163 (2002). Non-limiting examples include residues 114-220 of the below CD28 Sequence: MLRLLLALNL FPSIQVTGNK ILVKQSPMLV AYDNAVNLSC KYSYNLFSRE FRASLHKGLDSAVEVCVVYG NYSQQLQVYS KTGFNCDGKL GNESVTFYLQ NLYVNQTDIY FCKIEVMYPPPYLDNEKSNG TIIHVKGKHL CPSPLFPGPS KPFWVLVVVG GVLACYSLLVTVAFIIFWVR SKRSRLLHSD YMNMTPRRPG PTRKHYQPYA PPRDFAAYRS (SEQ ID NO: 87), and equivalents thereof.

As used herein, the term "ICOS costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the ICOS costimulatory signaling region sequence as shown herein. Non-limiting example sequences of the ICOS costimulatory signaling region are provided in U.S. Publication 2015/0017141A1 the exemplary polynucleotide encoding this sequence provided below.

ICOS costimulatory signaling region encoded by polynucleotide: ACAAAAAGA AGTATTCATC CAGTGTGCAC GACCCTAACG GTGAATACAT GTTCATGAGA GCAGTGAACA CAGCCAAAAA ATCCAGACTC ACAGATGTGA CCCTA (SEQ ID NO: 88), and equivalents thereof.

As used herein, the term "OX40 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the OX40 costimulatory signaling region sequence as shown herein. Non-limiting example sequences of the OX40 costimulatory signaling region are disclosed in U.S. Publication 2012/20148552A1, and include an exemplary sequence encoding such is provided below.

OX40 costimulatory signaling region encoded by polynucleotide: AGGGGACCAG AGGCTGCCCC CCGATGCCCA CAAGCCCCCT GGGGGAGGCA GTTTCCGGAC CCCCATCCAA GAGGAGCAGG CCGACGCCCA CTCCACCCTG GCCAAGATC (SEQ ID NO: 89), and equivalents thereof.

As used herein, the term "CD28 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the CD28 costimulatory signaling region sequence shown herein. The example sequences CD28 costimulatory signaling domain are provided in U.S. Pat. No. 5,686,281; Geiger, T. L. et al. (2001) Blood 98: 2364-2371; Hombach, A. et al. (2001) J Immunol 167: 6123-6131; Maher, J. et al. (2002) Nat Biotechnol 20: 70-75; Haynes, N. M. et al. (2002) J Immunol 169: 5780-5786 (2002); Haynes, N. M. et al. (2002) Blood 100: 3155-3163. Non-limiting examples include residues 114-220 of the below and the sequence encoded: CD28 Sequence: MLRLL-LALNL FPSIQVTGNK ILVKQSPMLV AYDNAVNLSC KYSYNLFSRE FRASLHKGLDSAVEVCVVYG NYSQQLQVYS KTGFNCDGKL GNESVTFYLQ NLY-VNQTDIY FCKIEVMYPPPYLDNEKSNG TIIHVKGKHL CPSPLFPGPS KPFWVLVVVG GVLA-CYSLLVTVAFIIFWVR SKRSRLLHSD YMNMTPRRPG PTRKHYQPYA PPRDFAAYRS (SEQ ID NO: 87), and equivalents thereof.

As used herein, the term "CD3 zeta signaling domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD3 zeta signaling domain sequence as shown herein. Non-limiting example sequences of the CD3 zeta signaling domain are provided in U.S. application Ser. No. 13/826, 258, e.g.: RVKFSRSADAPAYQQGQNQLYNELNLGR-REEYDVLDKRRGRDPEMGGKPRR KNPQEGLY-NELQKDKMAEAYSEIGMKGERRRGKGHDGLYQ-GLSTATKDTYD ALHMQALPPR (SEQ ID NO: 90), and equivalents thereof.

A "composition" typically intends a combination of the active agent, e.g., compound or composition, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. For example, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions disclosed herein. Aspects defined by each of these transition terms are within the scope of the present disclosure.

The term "consensus sequence" as used herein refers to an amino acid or nucleic acid sequence that is determined by aligning a series of multiple sequences and that defines an idealized sequence that represents the predominant choice of amino acid or base at each corresponding position of the multiple sequences. Depending on the sequences of the series of multiple sequences, the consensus sequence for the series can differ from each of the sequences by zero, one, a few, or more substitutions. Also, depending on the sequences of the series of multiple sequences, more than one consensus sequence may be determined for the series. The generation of consensus sequences has been subjected to intensive mathematical analysis. Various software programs can be used to determine a consensus sequence.

As used herein, the term "CRISPR" refers to a technique of sequence specific genetic manipulation relying on the clustered regularly interspaced short palindromic repeats pathway. CRISPR can be used to perform gene editing and/or gene regulation, as well as to simply target proteins to a specific genomic location. Gene editing refers to a type of genetic engineering in which the nucleotide sequence of a target polynucleotide is changed through introduction of deletions, insertions, or base substitutions to the polynucleotide sequence. In some aspects, CRISPR-mediated gene editing utilizes the pathways of nonhomologous end-joining (NHEJ) or homologous recombination to perform the edits. Gene regulation refers to increasing or decreasing the production of specific gene products such as protein or RNA.

The term "gRNA" or "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-

7, Mohr, S. et al. (2016) FEBS Journal 283: 3232-38, and Graham, D., et al. Genome Biol. 2015; 16: 260. gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In some aspects, a gRNA is synthetic (Kelley, M. et al. (2016) J of Biotechnology 233 (2016) 74-83). As used herein, a biological equivalent of a gRNA includes but is not limited to polynucleotides or targeting molecules that can guide a Cas9 or equivalent thereof to a specific nucleotide sequence such as a specific region of a cell's genome.

"Cytoreductive therapy," as used herein, includes but is not limited to chemotherapy, cryotherapy, and radiation therapy. Agents that act to reduce cellular proliferation are known in the art and widely used. Chemotherapy drugs that kill cancer cells only when they are dividing are termed cell-cycle specific. These drugs include agents that act in S-phase, including topoisomerase inhibitors and anti-metabolites.

Topoisomerase inhibitors are drugs that interfere with the action of topoisomerase enzymes (topoisomerase I and II). During the process of chemo treatments, topoisomerase enzymes control the manipulation of the structure of DNA necessary for replication, and are thus cell cycle specific. Examples of topoisomerase I inhibitors include the camptothecan analogs listed above, irinotecan and topotecan. Examples of topoisomerase II inhibitors include amsacrine, etoposide, etoposide phosphate, and teniposide.

Antimetabolites are usually analogs of normal metabolic substrates, often interfering with processes involved in chromosomal replication. They attack cells at very specific phases in the cycle. Antimetabolites include folic acid antagonists, e.g., methotrexate; pyrimidine antagonist, e.g., 5-fluorouracil, floxuridine, cytarabine, capecitabine, and gemcitabine; purine antagonist, e.g., 6-mercaptopurine and 6-thioguanine; adenosine deaminase inhibitor, e.g., cladribine, fludarabine, nelarabine and pentostatin; and the like.

Plant alkaloids are derived from certain types of plants. The *vinca* alkaloids are made from the periwinkle plant (Catharanthus *rosea*). The taxanes are made from the bark of the Pacific Yew tree (*taxus*). The *vinca* alkaloids and taxanes are also known as antimicrotubule agents. The podophyllotoxins are derived from the May apple plant. Camptothecan analogs are derived from the Asian "Happy Tree" (*Camptotheca acuminata*). Podophyllotoxins and camptothecan analogs are also classified as topoisomerase inhibitors. The plant alkaloids are generally cell-cycle specific.

Examples of these agents include *vinca* alkaloids, e.g., vincristine, vinblastine and vinorelbine; taxanes, e.g., paclitaxel and docetaxel; podophyllotoxins, e.g., etoposide and teniposide; and camptothecan analogs, e.g., irinotecan and topotecan.

Cryotherapy includes, but is not limited to, therapies involving decreasing the temperature, for example, hypothermic therapy.

Radiation therapy includes, but is not limited to, exposure to radiation, e.g., ionizing radiation, UV radiation, as known in the art. Exemplary dosages include, but are not limited to, a dose of ionizing radiation at a range from at least about 2 Gy to not more than about 10 Gy and/or a dose of ultraviolet radiation at a range from at least about 5 J/m$^2$ to not more than about 50 J/m$^2$, usually about 10 J/m$^2$.

As used herein, the term "detectable marker" refers to at least one marker capable of directly or indirectly, producing a detectable signal. A non-exhaustive list of this marker includes enzymes which produce a detectable signal, for example by colorimetry, fluorescence, luminescence, such as horseradish peroxidase, alkaline phosphatase, [3-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as $^{32}$P, 35 S or $^{125}$I.

An "effective amount" or "efficacious amount" refers to the amount of an agent, or combined amounts of two or more agents, that, when administered for the treatment of a mammal or other subject, is sufficient to effect such treatment for the disease. The "effective amount" will vary depending on the agent(s), the disease and its severity and the age, weight, etc., of the subject to be treated.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof.

The antisense strand is the complement of such a nucleic acid, and the encoding sequence can be deduced therefrom.

As used herein, the term "enhancer", as used herein, denotes sequence elements that augment, improve or ameliorate transcription of a nucleic acid sequence irrespective of its location and orientation in relation to the nucleic acid sequence to be expressed.

An enhancer may enhance transcription from a single promoter or simultaneously from more than one promoter. As long as this functionality of improving transcription is retained or substantially retained (e.g., at least 70%, at least 80%, at least 90% or at least 95% of wild-type activity, that is, activity of a full-length sequence), any truncated, mutated or otherwise modified variants of a wild-type enhancer sequence are also within the above definition.

In one aspect, the term "equivalent" or "biological equivalent" of an antibody means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at cancer.gov, last visited on May 1, 2008. Typically, a patient is given a subsequent chemotherapy regimen because the patient did not show a positive clinical or sub-clinical response to the first line therapy or the first line therapy has stopped.

As used herein, "homology" or "identical", percent "identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein).

Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. The terms "homology" or "identical", percent "identity" or "similarity" also refer to, or can be applied to, the complement of a test sequence. The terms also include sequences that have deletions and/or additions, as well as those that have substitutions. As described herein, the preferred algorithms can account for gaps and the like. Preferably, identity exists over a region that is at least about 25 amino acids or nucleotides in length, or more preferably over a region that is at least 50-100 amino acids or nucleotides in length. An "unrelated" or "non-homologous" sequence shares less than 40% identity, or alternatively less than 25% identity, with one of the sequences disclosed herein.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15

M NaCl and 15 mM citrate buffer. It is understood that equivalents of SSC using other buffer systems can be employed.

The term "isolated" as used herein refers to molecules or biologicals or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

As used herein, the term "isolated cell" generally refers to a cell that is substantially separated from other cells of a tissue.

"Immune cells" includes, e.g., white blood cells (leukocytes) which are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic cells).

As used herein the term "linker sequence" relates to any amino acid sequence comprising from 1 to 10, or alternatively, 8 amino acids, or alternatively 6 amino acids, or alternatively 5 amino acids that may be repeated from 1 to 10, or alternatively to about 8, or alternatively to about 6, or alternatively about 5, or 4 or alternatively 3, or alternatively 2 times. For example, the linker may comprise up to 15 amino acid residues consisting of a pentapeptide repeated three times. In one aspect, the linker sequence is a (Glycine4Serine)3 (SEQ ID NO: 91) flexible polypeptide linker comprising three copies of gly-gly-gly-gly-ser (SEQ ID NO: 92).

A "normal cell corresponding to the tumor tissue type" refers to a normal cell from a same tissue type as the tumor tissue. A non-limiting example is a normal lung cell from a patient having lung tumor, or a normal colon cell from a patient having colon tumor.

As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface. T-cells may either be isolated or obtained from a commercially available source. "T cell" includes all types of immune cells expressing CD3 including T-helper cells (CD4+ cells), cytotoxic T-cells (CD8+cells), natural killer T-cells, T-regulatory cells (Treg) and gamma-delta T cells. A "cytotoxic cell" includes CD8+T cells, natural-killer (NK) cells, and neutrophils, which cells are capable of mediating cytotoxicity responses. Non-limiting examples of commercially available T-cell lines include lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™), TALL-104 cytotoxic human T cell line (ATCC #CRL-11386). Further examples include but are not limited to mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Be13, CCRF-CEM, CML-T1, DND-41, DU.528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4;11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL-8294), HuT102 (ATCC TIB-162). Null leukemia cell lines, including but not limited to REH, NALL-1, KM-3, L92-221, are a another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (atcc.org/) and the German Collection of Microorganisms and Cell Cultures (dsmz.de/).

As used herein, the term "NK cell," also known as natural killer cell, refers to a type of lymphocyte that originates in the bone marrow and play a critical role in the innate immune system. NK cells provide rapid immune responses against viral-infected cells, tumor cells or other stressed cell, even in the absence of antibodies and major histocompatibility complex on the cell surfaces. NK cells may either be isolated or obtained from a commercially available source. Non-limiting examples of commercial NK cell lines include lines NK-92 (ATCC® CRL-2407™), NK-92MI (ATCC® CRL-2408™). Further examples include but are not limited to NK lines HANK1, KHYG-1, NKL, NK-YS, NOI-90, and YT. Non-limiting exemplary sources for such commercially available cell lines include the American Type Culture Collection, or ATCC, (atcc.org/) and the German Collection of Microorganisms and Cell Cultures (dsmz.de/).

As used herein in reference to a regulatory polynucleotide, the term "operatively linked" refers to an association between the regulatory polynucleotide and the polynucleotide sequence to which it is linked such that, when a specific protein binds to the regulatory polynucleotide, the linked polynucleotide is transcribed.

As used herein, the term "overexpress" with respect to a cell, a tissue, or an organ expresses a protein to an amount that is greater than the amount that is produced in a control cell, a control issue, or an organ. A protein that is overexpressed may be endogenous to the host cell or exogenous to the host cell.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any aspect of this technology that is a polynucleotide encompasses both the double-stranded form and each of two complementary single-stranded forms known or predicted to make up the double-stranded form.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As used herein, the term "purification marker" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, the term "specific binding" means the contact between an antibody and an antigen with a binding affinity of at least $10^{-6}$ M. In certain aspects, antibodies bind with affinities of at least about $10^{-7}$ M, and preferably $10^{-8}$ M, $10^{-9}$ M, $10^{-10}$ M, $10^{-11}$ M, or $10^{-12}$ M.

As used herein, the term "fusion protein" or "fusion polypeptide" intends any drug (small molecule, polypeptide or protein) fused or joined to an antibody or fragment thereof as disclosed herein. Non-limiting examples of such includes, for example, bispecific and antibody-drug conjugates A "solid tumor" is an abnormal mass of tissue that usually does not contain cysts or liquid areas. Solid tumors can be benign or malignant, metastatic or non-metastatic. Different types of solid tumors are named for the type of cells that form them. Examples of solid tumors include sarcomas, carcinomas, and lymphomas.

As used herein, the term "suicide gene" is a gene capable of inducing cell apoptosis; non-limiting examples include HSV-TK (Herpes simplex virus thymidine kinase), cytosine deaminase, nitroreductase, carboxylesterase, cytochrome P450 or PNP (Purine nucleoside phosphorylase), truncated EGFR, or inducible caspase ("iCasp").

Suicide genes may function along a variety of pathways, and, in some cases, may be inducible by an inducing agent such as a small molecule. For example, the iCasp suicide gene comprises portion of a caspase protein operatively linked to a protein optimized to bind to an inducing agent; introduction of the inducing agent into a cell comprising the suicide gene results in the activation of caspase and the subsequent apoptosis of said cell.

The term "transduce" or "transduction" as it is applied to the production of chimeric antigen receptor cells refers to the process whereby a foreign nucleotide sequence is introduced into a cell. In some embodiments, this transduction is done via a vector.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. Treatments containing the disclosed compositions and methods can be first line, second line, third line, fourth line, fifth line therapy and are intended to be used as a sole therapy or in combination with other appropriate therapies. In one aspect, the term "treatment" excludes prevention.

As used herein, the term "vector" refers to a nucleic acid construct deigned for transfer between different hosts, including but not limited to a plasmid, a virus, a cosmid, a phage, a BAC, a YAC, etc. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector.

As used herein the term "CLDN 18.2" refers to isoform 2 of claudin-18. See Sahin U, Koslowski M, Dhaene K, Usener D, Brandenburg G, Seitz G, Huber C, Tureci O. Claudin-18 splice variant 2 is a pan-cancer target suitable for therapeutic antibody development, *Clin. Cancer Res.* 2008; 14(23):7624-34. Non-limiting exemplary sequences of claudin 18 or the underlying gene may be found under Gene Cards ID: GC03P137998, HGNC: 2039, Entrez Gene: 51208, Ensembl: ENSG00000066405, OMIM: 609210, and UniProtKB: P56856, which are incorporated by reference herein.

The sequences associated with each of the above listed GenBank Accession Nos. and references are herein incorporated by reference.

Modes for Carrying Out the Disclosure

This disclosure provides a novel antibody to CLDN 18.2 and compositions and methods of use thereof. More specifically, this disclosure provides new anti-CLDN 18.2 antibodies for the treatment of tumors expressing CLDN 18.2, such as for example, GI tumors that include, but are not limited to, gastric, pancreatic, esophageal, biliary tract, colorectal, ovarian, and lung carcinomas. The target, CLDN 18.2, is highly expressed on the majority of these tumors but has restricted off-target positivity and therefore a desirable safety profile. Thus, in one aspect, the compositions are particularly useful in the treatment of tumors or cancerous cell that express or overexpress CLDN 18.2.

Figure 1B:
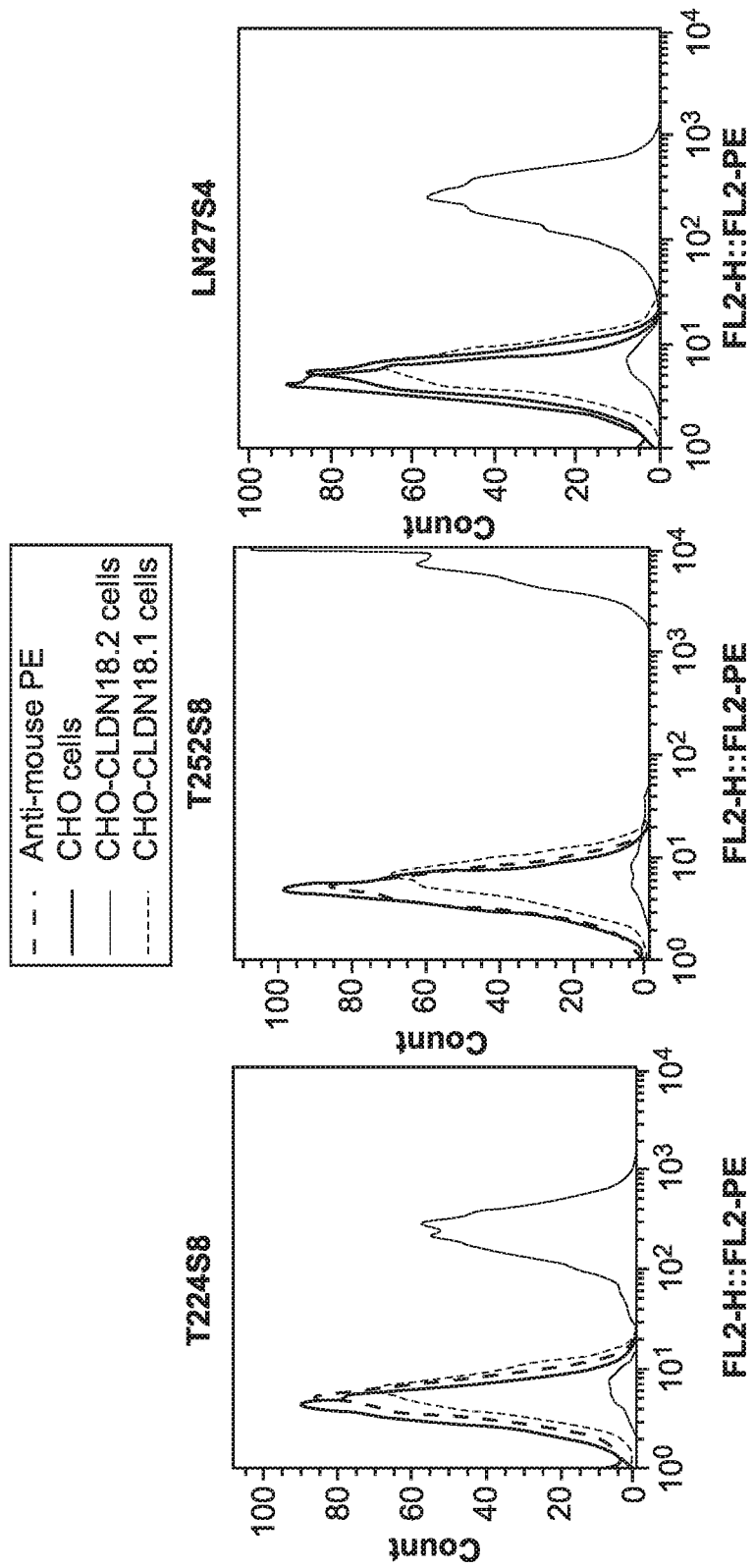
Figure 9:
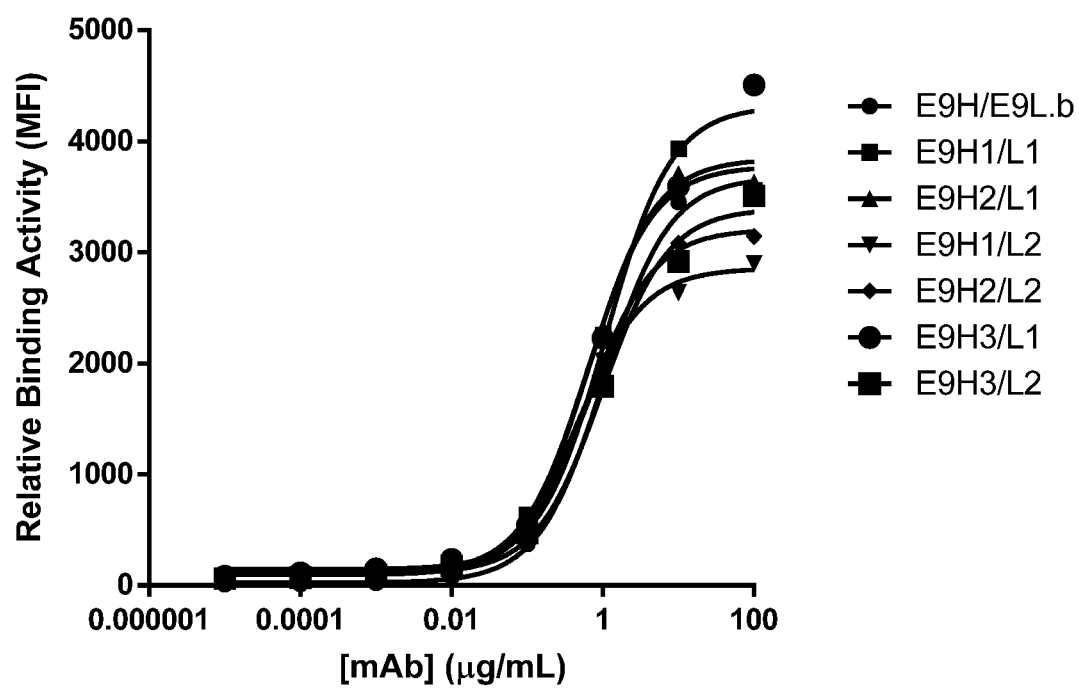
FIG. 9 shows humanized anti-CLDN 18.2 antibodies, HuT252S4, bind to cell surface human CLDN 18.2 on CHO cells stably expressing CLDN 18.2 at similar or higher affinity as the chimeric T252S4 antibody.

In one aspect, the present disclosure provides isolated antibodies, the antibodies comprising a heavy chain (HC) immunoglobulin variable domain sequence and a light chain (LC) immunoglobulin variable domain sequence, wherein the antibodies bind to an epitope of CLDN 18.2. In one aspect, the antibodies bind to an epitope of CLDN 18.2, but not CLDN 18.1. In one aspect, the antibody is a humanized antibody comprising one or more, two or more, three or more, four or more, five or more, six or more, seven or more or all eight of the CDRs identified in Table 3. In another aspect, the antibodies bind with high specificity, that is they bind to CLDN 18.2 with an affinity of more than 80%, or alternatively more than 85%, or alternatively more than 90%, or alternatively more than 95%, binding for CLDN 18.2-expressing cells versus less than 20%, or alternatively less than 15%, or alternatively less than 10%, or alternatively less than 5% binding to CLDN 18.1. Example of such are shown in FIGS. 1*a*, 1*b* and 9. There, the antibodies are more specific for the CLDN 18.2 expressing tumor cells and would have lower toxicity since they do not bind to the CLDN 18.1-expressing normal cells.

In some embodiments, the antibody is a bispecific antibody has a binding specificity to a second target protein. The second target protein, in some embodiments, is selected from the group consisting of IL-1, CD3, CD16, CD19, CD28, CD47, CD64, PD-1, PD-L1, CTLA-4, LAG-3, CD28, CD122, 4-1BB, TIM3, OX-40, OX40L, CD40, CD40L, LIGHT, ICOS, ICOSL, GITR, GITRL, TIGIT, CD27, VISTA, B7H3, B7H4, HEVM, BTLA and KIR. In some embodiments, the antibody is comprised in an antibody drug conjugates (ADC) formed between the antibody and another agent, such as toxin or drug. In some embodiments, the antibodies may be conjugated to therapeutic agents, prodrugs, peptides, proteins, enzymes, viruses, lipids, biological response modifiers, pharmaceutical agents, and/or polyethylene glycol (PEG).

In a further aspect, this disclosure provides isolated anti-CLDN 18.2 antibodies or fragments thereof as disclosed herein and a detectable or purification label, alone or in combination with an CLDN 18.2 antigen or fragment (e.g., VH1, VH2, VH3, VL1, VL2, VL3, heavy and light chain CDR1, CDR2, heavy and light chain heavy and light chain CDR1, CDR2, CDR3) thereof, that in one aspect are bound to each other to form an antigen/antibody complex. Further provided herein is an ex vivo cell comprising this antigen/antibody complex.

Aspects of the disclosure relate to a chimeric antigen receptor (CAR) comprising: (a) an antigen binding domain of a CLDN 18.2 antibody (e.g., VH1, VH2, VH3, VL1, VL2, VL3, heavy and light chain CDR1, CDR2, CDR3); (b) a hinge domain; (c) a transmembrane domain; and (d) an intracellular domain. Further aspects of the disclosure relate to a chimeric antigen receptor (CAR) comprising: (a) an antigen binding domain of a CLDN 18.2 antibody (e.g., VH1, VH2, VH3, VL1, VL2, VL3, heavy and light chain CDR 1, CDR2, CDR3); (b) a hinge domain; (c) a CD28 transmembrane domain; (d) one or more costimulatory regions selected from a CD28 costimulatory signaling region, a 4-1BB costimulatory signaling region, an ICOS costimulatory signaling region, and an OX40 costimulatory region; and (e) a CD3 zeta signaling domain and alternatives thereof.

In a further aspect, the present disclosure provides a chimeric antigen receptor (CAR) comprising: (a) an antigen binding domain of an anti-CLDN 18.2 antibody (e.g., VH1, VH2, VH3, VL1, VL2, VL3, heavy and light chain CDR1, CDR2, CDR3), (b) a CD8α hinge domain; (c) a CD8α transmembrane domain; (d) a CD28 and/or a 4-1BB costimulatory signaling region; and (e) a CD3 zeta signaling domain and alternatives thereof.

In another aspect, the present disclosure provides an isolated nucleic acid sequence encoding the anti-CLDN 18.2 antibody, humanized antibody, bispecific antibody, or the anti-CLDN 18.2 CAR.

In another aspect, the present disclosure provides a vector comprising the isolated nucleic acid sequence encoding the anti-CLDN 18.2 antibody, bispecific antibody, humanized antibody, or the anti-CLDN 18.2 CAR.

In another aspect, the present disclosure provides a vector comprising the isolated nucleic acid sequence encoding the anti-CLDN 18.2 antibody, bispecific antibody, humanized antibody, or the anti-CLDN 18.2 CAR, operatively linked to sequences that direct and optionally enhance the expression of the nucleic acid sequence. These sequences include promoters and enhancer sequences.

In another aspect, the present disclosure provides a composition comprising a carrier and one or more of: the anti-CLDN 18.2 antibody; and/or the chimeric antibody; and/or the bispecific antibody; and/or the humanized antibody; and/or the anti-CLDN 18.2 CAR; and/or the isolated nucleic acid encoding the anti-CLDN 18.2 antibody bispecific antibody, and/or the chimeric antibody; and/or the anti-CLDN 18.2 humanized antibody, or the anti-CLDN 18.2 CAR; and/or the vector comprising the isolated nucleic acid sequence encoding the anti-CLDN 18.2 antibody, bispecific antibody, and/or the chimeric antibody; and/or the humanized antibody, or the anti-CLDN 18.2 CAR; and/or an isolated cell comprising the anti-CLDN 18.2 CAR.

In one aspect, the disclosure provides a composition comprising, or alternatively consisting essentially of, or yet further consisting of a carrier and one or more of: an antibody or fragment (e.g., VH1, VH2, VH3, VL1, VL2, VL3, heavy and light chain CDR 1, CDR2, CDR3) thereof, a nucleic acid encoding the antibody or fragment (e.g., VH1, VH2, VH3, VL1, VL2, VL3, heavy and light chain CDR1, CDR2, CDR3) thereof, a vector comprising the nucleic acid encoding the antibody or fragment (e.g., VH1, VH2, VH3, VL1, VL2, VL3, heavy and light chain CDR1, CDR2, CDR3) thereof, an isolated cell comprising an anti-CLDN 18.2 CAR and/or a polynucleotide encoding the antibody or fragment (e.g., VH1, VH2, VH3, VL1, VL2, VL3, heavy and light chain CDR1, CDR2, CDR3) thereof; and/or the isolated nucleic acid encoding the CAR; and/or the vector comprising the nucleic acid encoding the CAR; and/or the isolated cell expressing an anti-CLDN 18.2 CAR; and/or the anti-CLDN 18.2 antibody; and/or the chimeric antibody; and/or bispecific antibody; and/or the humanized antibody.

Compositions are also provided. In one embodiment, the composition comprises an antibody or fragment (e.g., VH1, VH2, VH3, VL1, VL2, VL3, heavy and light chain CDR 1, CDR2, CDR3) thereof, a fusion protein, or a CAR and/or car expressing-cell of the present disclosure and a pharmaceutically acceptable carrier. Also provided is an isolated cell comprising one or more polynucleotide encoding the antibody or fragment (e.g., VH1, VH2, VH3, VL1, VL2, VL3, heavy and light chain CDR1, CDR2, CDR3) thereof or the fusion protein or bispecific antibody of the present disclosure.

The present disclosure further provides a method of treating tumor or growth expressing CLDN 18.2 antigen, such as for example cancer or fibrosis in a patient in need thereof, comprising administering to the patient a antibody or fragment (e.g., VH1, VH2, VH3, VL1, VL2, VL3, heavy and light chain CDR1, CDR2, CDR3) thereof, a fusion protein, or a CAR and/or car expressing-cell of the present disclosure. Non-limiting examples of cancers include GI cancers, bladder cancer, liver cancer, colon cancer, rectal cancer, endometrial cancer, biliary cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer. The methods can be combined with diagnostic methods to identify patients or subjects that are more likely to respond to the treatment.

Antibodies and Uses Thereof

I. Compositions

The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of CDR1, CDR2 and CDR3 of the heavy and light chains. Thus once a set of CDR sequences (i.e. the sequence of CDR1, CDR2 and CDR3 for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

In one embodiment, the disclosure provides an isolated antibody comprising a heavy chain (HC) immunoglobulin variable domain sequence and a light chain (LC) immunoglobulin variable domain sequence, wherein the antibody binds to an epitope CLDN 18.2.

In one aspect, the HC of the antibody comprises or alternatively consists essentially of, or yet further consists of one or more of a CDR1 comprising the amino acid sequence selected from (i) GFTFSSYA (SEQ ID NO: 4), (ii) GFTFSDYY (SEQ ID NO: 10), (iii) GFNIKDYF (SEQ ID NO: 16), (iv) GFTFSDYY (SEQ ID NO: 10), (v) GYSFTGYN (SEQ ID NO: 28), (vi) GFSLTSYG (SEQ ID NO: 34), (vii) GYNMN (SEQ ID NO: 93) or an equivalent of each thereof, and/or a CDR2 comprising the amino acid sequence selected from (i) ISGGGST (SEQ ID NO: 5), (ii) ISDGGGDT (SEQ ID NO: 11), (iii) IDPENGDT (SEQ ID NO: 17), (iv) ISNGGGST (SEQ ID NO: 23), (v) INPYNGGT (SEQ ID NO: 29), (vi) IWSDGRT (SEQ ID NO: 35), (vii) LINPYNGGTRYNQKFKG (SEQ ID NO: 94), or an equivalent of each thereof, and/or a CDR3 comprising the amino acid sequence selected from (i) ARGGNIYDGYPYYFDY (SEQ ID NO: 95), (ii) GGNIYDGYPYYFDY (SEQ ID NO: 6), (iii) ARHRGSLDY (SEQ ID NO: 12), (iv) NVLGYGNYGHFYYAMDY (SEQ ID NO: 18), (v) ARHRGSLDF (SEQ ID NO: 24), (vi) ARMGLGNAMDY (SEQ ID NO: 30), (vii) ARHGRYDPYAMDY (SEQ ID NO: 36), (viii) MGLGNAMDY (SEQ ID NO: 96), or an equivalent of each thereof, and/or the LC comprises the antibody of comprises or alternatively consists essentially of, or yet further consists of a CDR1 comprising the amino acid sequence selected from (i) QNLLNSSNQKNY (SEQ ID NO: 1), (ii) ESVDNYGFSF (SEQ ID NO: 7), (iii) QSLVHSNGNTY (SEQ ID NO: 13), (iv) QNLLNSGNQKNY (SEQ ID NO: 25), (v) KSSQNLLNSGNQKNYLT (SEQ ID NO: 97), or an equivalent of each thereof, and/or a CDR2 comprising the amino acid sequence selected from (i) FAS (SEQ ID NO: 2), (ii) RAS (SEQ ID NO: 8), (iii) KVS (SEQ ID NO: 14), (iv) WAS (SEQ ID NO: 26), (v) WASTMES (SEQ ID NO: 98), or an equivalent of each thereof, and/or a CDR3 comprising the amino acid sequence selected from (i) QQHYSTPLT (SEQ ID NO: 3), (ii) QQSNQGPLT (SEQ ID NO: 9), (iii) SQNTHVPRT (SEQ ID NO: 15), (iv) QQSNKVPLT (SEQ ID NO: 21), (v) QNDYIYPLP (SEQ ID NO: 27), or an equivalent of each thereof.

In one aspect, the HC of the antibody comprises or alternatively consists essentially of, or yet further consists of one or more of a CDR1 comprising the amino acid sequence of GFTFSSYA (SEQ ID NO: 4) or an equivalent thereof, and/or a CDR2 comprising the amino acid sequence of ISGGGST (SEQ ID NO: 5) or an equivalent thereof, and/or a CDR3 comprising the amino acid sequence of GGNIYDGYPYYFDY (SEQ ID NO: 6) or an equivalent thereof, and/or the LC comprises the antibody of comprises or alternatively consists essentially of, or yet further consists of a CDR1 comprising the amino acid sequence of QNLLNSSNQKNY (SEQ ID NO: 1) or an equivalent thereof, and/or a CDR2 comprising the amino acid sequence of FAS (SEQ ID NO: 2) or an equivalent thereof, and/or a CDR3 comprising the amino acid sequence of QQHYSTPLT (SEQ ID NO: 3) or an equivalent thereof.

In one aspect, the HC of the antibody comprises or alternatively consists essentially of, or yet further consists of one or more of a CDR1 comprising the amino acid sequence of GFTFSDYY (SEQ ID NO: 10) or an equivalent thereof, and/or a CDR2 comprising the amino acid sequence of ISDGGGDT (SEQ ID NO: 11) or an equivalent thereof, and/or a CDR3 comprising the amino acid sequence of ARHRGSLDY (SEQ ID NO: 12) or an equivalent thereof, and/or the LC comprises the antibody of comprises or alternatively consists essentially of, or yet further consists of a CDR1 comprising the amino acid sequence of ESVDNYGFSF (SEQ ID NO: 7) or an equivalent thereof, and/or a CDR2 comprising the amino acid sequence of RAS (SEQ ID NO: 8) or an equivalent thereof, and/or a CDR3 comprising the amino acid sequence of QQSNQGPLT (SEQ ID NO: 9) or an equivalent thereof.

In one aspect, the HC of the antibody comprises or alternatively consists essentially of, or yet further consists of one or more of a CDR1 comprising the amino acid sequence of GFNIKDYF (SEQ ID NO: 16) or an equivalent thereof, and/or a CDR2 comprising the amino acid sequence of IDPENGDT (SEQ ID NO: 17) or an equivalent thereof, and/or a CDR3 comprising the amino acid sequence of NVLGYGNYGHFYYAMDY (SEQ ID NO: 18) or an equivalent thereof, and/or the LC comprises the antibody of comprises or alternatively consists essentially of, or yet further consists of a CDR1 comprising the amino acid sequence of QSLVHSNGNTY (SEQ ID NO: 13) or an equivalent thereof, and/or a CDR2 comprising the amino acid sequence of KVS (SEQ ID NO: 14) or an equivalent thereof, and/or a CDR3 comprising the amino acid sequence of SQNTHVPRT (SEQ ID NO: 15) or an equivalent thereof.

In one aspect, the HC of the antibody comprises or alternatively consists essentially of, or yet further consists of one or more of a CDR1 comprising the amino acid sequence of GFTFSDYY (SEQ ID NO: 10) or an equivalent thereof, and/or a CDR2 comprising the amino acid sequence of ISNGGGST (SEQ ID NO: 23) or an equivalent thereof, and/or a CDR3 comprising the amino acid sequence of ARHRGSLDF (SEQ ID NO: 24) or an equivalent thereof, and/or the LC comprises the antibody of comprises or alternatively consists essentially of, or yet further consists of a CDR1 comprising the amino acid sequence of ESVDNYGFSF (SEQ ID NO: 7) or an equivalent thereof, and/or a CDR2 comprising the amino acid sequence of RAS (SEQ ID NO: 8) or an equivalent thereof, and/or a CDR3 comprising the amino acid sequence of QQSNKVPLT (SEQ ID NO: 21) or an equivalent thereof.

In one aspect, the HC of the antibody comprises or alternatively consists essentially of, or yet further consists of one or more of a CDR1 comprising the amino acid sequence of GYSFTGYN (SEQ ID NO: 28) or an equivalent thereof, and/or a CDR2 comprising the amino acid sequence of INPYNGGT (SEQ ID NO: 29) or an equivalent thereof, and/or a CDR3 comprising the amino acid sequence of ARMGLGNAMDY (SEQ ID NO: 30) or an equivalent thereof, and/or the LC comprises the antibody of comprises or alternatively consists essentially of, or yet further consists of a CDR1 comprising the amino acid sequence of QNLLNSGNQKNY (SEQ ID NO: 25) or an equivalent thereof, and/or a CDR2 comprising the amino acid sequence of WAS (SEQ ID NO: 26) or an equivalent thereof, and/or a CDR3 comprising the amino acid sequence of QNDYIYPLP (SEQ ID NO: 27) or an equivalent thereof.

In one aspect, the HC of the antibody comprises or alternatively consists essentially of, or yet further consists of one or more of a CDR1 comprising the amino acid sequence of GFSLTSYG (SEQ ID NO: 34) or an equivalent thereof, and/or a CDR2 comprising the amino acid sequence of IWSDGRT (SEQ ID NO: 35) or an equivalent thereof, and/or a CDR3 comprising the amino acid sequence of ARHGRYDPYAMDY (SEQ ID NO: 36) or an equivalent thereof, and/or the LC comprises the antibody of comprises or alternatively consists essentially of, or yet further consists of a CDR1 comprising the amino acid sequence of ESVDNYGFSF (SEQ ID NO: 7) or an equivalent thereof, and/or a CDR2 comprising the amino acid sequence of RAS (SEQ ID NO: 8) or an equivalent thereof, and/or a CDR3 comprising the amino acid sequence of QQSNQGPLT (SEQ ID NO: 9) or an equivalent thereof.

In one aspect, the HC of the antibody comprises or alternatively consists essentially of, or yet further consists of one or more of a CDR1 comprising the amino acid sequence of KSSQNLLNSGNQKNYLT (SEQ ID NO: 97) or an equivalent thereof, and/or a CDR2 comprising the amino acid sequence of WASTMES (SEQ ID NO: 98) or an equivalent thereof, and/or a CDR3 comprising the amino acid sequence of QNDYIYPLP (SEQ ID NO: 27) or an equivalent thereof, and/or the LC comprises the antibody of comprises or alternatively consists essentially of, or yet further consists of a CDR1 comprising the amino acid sequence of GYNMN (SEQ ID NO: 93) or an equivalent thereof, and/or a CDR2 comprising the amino acid sequence of LINPYNGGTRYNQKFKG (SEQ ID NO: 94) or an equivalent thereof, and/or a CDR3 comprising the amino acid sequence of MGLGNAMDY (SEQ ID NO: 96) or an equivalent thereof.

In one aspect, the heavy chain variable region comprises, or alternatively consists essentially of, or yet further consists of a heavy chain amino acid sequence of the anti-CLDN 18.2 antibody disclosed herein, and the light chain variable region comprises, or alternatively consists essentially of, or yet further consists of the light chain amino acid sequence from anti-CLDN 18.2 antibody disclosed herein, or equivalents thereof, as follows (CDRs are underlined):

Anti-CLDN 18.2 Heavy Chain Amino Acid Sequence (T155S2): EVKLVESGGGLVKPGGSLKLS-CAASGFTFSSYAMSWVRQTPEKRLEWVASISGGGS TYYPDSVKGRFTISRDNARNILYLQMSYLRSED-TAVYYCARGGNIYDGYPYYFDY WGQGTTLTVSS (SEQ ID NO: 38), or an equivalent thereof.

Anti-CLDN 18.2 Light Chain Amino Acid Sequence (T155S2): DIVMTQSPSSLAMSVGQKVTMSCK- SSQNLLNSSNQKNYLAWYQQKPGQSPKLLVY FAS-TRESGVPDRFTGSGSGTDFTLTISSVQAEDLAVYY-COOHYSTPLTFGAGTKLEL K (SEQ ID NO: 40), or an equivalent thereof.

Anti-CLDN 18.2 Heavy Chain Amino Acid Sequence (T158S2): EVKLVESGGGLVQPGGSLKLS-CATSGFTFSDYYMFWIRQTPEKRLEWVASISDGGG DTYYPDTVKGRFTISRDNAKNTLYLQMSRLKSED-TAMYYCARHRGSLDYWGQGT TLTVSS (SEQ ID NO: 42), or an equivalent thereof.

Anti-CLDN 18.2 Light Chain Amino Acid Sequence (T158S2): DIVLTQSPASLAVSLGQRATISCRAS-ESVDNYGFSFLHWYQQKPGQPPKLLIYRASN LASGI-PARFSGSGSRTDFTLTINPVETDDVATYYCOOSNOG-PLTFGAGTKLELK (SEQ ID NO: 44), or an equivalent thereof.

Anti-CLDN 18.2 Heavy Chain Amino Acid Sequence (T224S8): EVQLQQSGTELVRS-GASVKLSCTTSGFNIKDYFLHWVKQRPEQ-GLEWIGWIDPENG DTKYAPKFQDKVTMTVDTSSN-TACLHLSSLTSDDTAVYYCNVLGYGNYGHFYYA MDYWGQGTSVTVSS (SEQ ID NO: 46), or an equivalent thereof.

Anti-CLDN 18.2 Light Chain Amino Acid Sequence (T224S8): DVVMTQTPLSLPVSLGDQASIS-CRSSQSLVHSNGNTYLHWYLQKPGQSPKLLIYKV SNRFSGVPDRFSGSESGTDFTLKISRVEAE-DLGIYFCSQNTHVPRTFGGGTKLEIR (SEQ ID NO: 48), or an equivalent thereof.

Anti-CLDN 18.2 Heavy Chain Amino Acid Sequence (T192S2): EVKLVESGGGLVQPGGSLKLS-CATSGFTFSDYYMYWVRQTPEKRLEWVAYISNGG GSTYYPDTVKGRFTISRDNAKNTLYLQMSRLKSED-TAMYYCARHRGSLDFWGQGT TLTVSS (SEQ ID NO: 50), or an equivalent thereof.

Anti-CLDN 18.2 Light Chain Amino Acid Sequence (T192S2): DIVLTQSPASLAVSLGQRATISCRAS-ESVDNYGFSFMHWYQQKPGQPPKLLIYRASN LES-GIPARFSGSWSRTDFTLTINPVETDD-VATYYCQQSNKVPLTFGAGTKLELK (SEQ ID NO: 52), or an equivalent thereof.

Anti-CLDN 18.2 Heavy Chain Amino Acid Sequence (T252S4): EVQLQQSGPELVKPGASMKISCK-ASGYSFTGYNMNWVKQTHGKNLEWIGLINPYN GGTRYNQKFKGKATLTVDKSSSTAYMELLSLTSED-SAVYFCARMGLGNAMDYWG QGTSVTVSS (SEQ ID NO: 54), or an equivalent thereof.

Anti-CLDN 18.2 Light Chain Amino Acid Sequence (T252S4): DIVMTQSPSSLTVTAGEKVTMSCK-SSQNLLNSGNQKNYLTWYQQKPGQPPKLLIY WASTMESGVPDRFTGSGSGTDFTLTISSVQAED-LAVYYCQNDYIYPLPFGAGTKLE LK (SEQ ID NO: 56), or an equivalent thereof.

Anti-CLDN 18.2 Heavy Chain Amino Acid Sequence (T88S1): QVQLKESGPGLVAPSQSLSITCTISGFSLTSY-GIHWVRQPPGKGLEWLVVIWSDGRT TYNSALKSRL-SISKDNSKSQVFLKMNSLQTDDTAMYYCAR-HGRYDPYAMDYWGQ GTSVTVSS (SEQ ID NO: 58), or an equivalent thereof.

Anti-CLDN 18.2 Light Chain Amino Acid Sequence (T88S1): DIVLTQSPASLAVSLGQRATISCRAS-ESVDNYGFSFLHWYQQKPGQPPKLLIYRASN LASGI-PARFSGSGSRTDFTLTINPVETDDVATYYCQQSNQG-PLTFGAGTKLELK (SEQ ID NO: 44), or an equivalent thereof.

Anti-CLDN 18.2 Heavy Chain Amino Acid Sequence (Chimeric T252S4): EVQLQQSGPELVKPGASMKISCK-ASGYSFTGYNMNWVKQTHGKNLEWIGLINPYN GGTRYNQKFKGKATLTVDKSSSTAYMELLSLTSED-SAVYFCARMGLGNAMDYWG QGTSVTVSS (SEQ ID NO: 54), or an equivalent thereof.

Anti-CLDN 18.2 Light Chain Amino Acid Sequence (Chimeric T252S4): DIVMTQSPSSLTVTAGEKVTMSCKSSQNLLNSGNQK-NYLTWYQQKPGQPPKLLIY WASTMESGVPDRFTGSGSGTDFTLTISSVQAED-LAVYYCQNDYIYPLPFGAGTKLE LK (SEQ ID NO: 56), or an equivalent thereof.

Anti-CLDN 18.2 Heavy Chain Amino Acid Sequence (HuVH1 T252S4): EVQLVQSGAEVKKPGESLKIS-CKGSGYSFTGYNMNWVRQMPGKGLEWMGLINPY NGGTRYNQKFKGQVTISADKSISTAYLQWSSLKASD-TAMYFCARMGLGNAMDYW GQGTTVTVSS (SEQ ID NO: 62), or an equivalent thereof.

Anti-CLDN 18.2 Heavy Chain Amino Acid Sequence (HuVH2 T252S4): EVQLVQSGAEVKKPGESLKIS-CKGSGYSFTGYNMNWVRQMIPGKNLEWIGLINPYN GGTRYNQKFKGQVTISADKSISTAY-LQWSSLKASTAMYFCARMGLGNAMDYWG QGTTVTVSS (SEQ ID NO: 63), or an equivalent thereof.

Anti-CLDN 18.2 Heavy Chain Amino Acid Sequence (HuVH3 T252S4): EVQLVQSGAEVKKPGESLKIS-CKGSGYSFTGYNMNWVRQMPGKNLIEWIGLINPYN GGTRYNQKFKGKAITLSVKSISTAYLQWSSLKASD-TAMYFCARMGLGNAMDYW GQGTTVTVSS (SEQ ID NO: 64), or an equivalent thereof.

Anti-CLDN 18.2 Light Chain Amino Acid Sequence (HuVL1 T252S4): DIVMTQSPDSLAVSLGERATINCK-SSQNLLNSGNQKNYLTWYQQKPGQPPKLLIYW ASTMESGVPDRFSGSGSGTDFTLTISSLQAEDVA-VYYCQNDYIYPLPFGQGTKLEIK (SEQ ID NO: 66), or an equivalent thereof.

Anti-CLDN 18.2 Light Chain Amino Acid Sequence (HuVL2 T252S4): DIVMTQSPDSLAVSLGERATINCK-SSQNLLQSGNQKNYLTWYQQKPGQPPKLLIYW ASTRESGVPDRFSGSGSGTDFTLTISSLQAEDVA-VYYCQNDYIYPLPFGQGTKLEIK (SEQ ID NO: 67), or an equivalent thereof.

In one aspect, the heavy chain variable region comprises, or alternatively consists essentially of, or yet further consists of an heavy chain encoded by the nucleic acid sequence of the anti-CLDN 18.2 antibody disclosed herein, and the light chain variable region comprises, or alternatively consists essentially of, or yet further consists of the light chain chain encoded by the nucleic acid sequence from anti-CLDN 18.2 antibody disclosed herein, or equivalents thereof, as follows (CDRs are underlined):

Anti-CLDN 18.2 Heavy Chain Nucleic Acid Sequence (T155S2): GAAGTGAAGCTGGTGGAGTCTGGGG-AGGGCTTAGTGAAGCCTGGAGGGTCCCT GAAACTCTCCTGTGCAGCCTCTGGATT-CACTTTCAGTAGCTATGCCATGTCTTGG GTTCGCCAGACTCCAGAGAAGAGGCTG-GAGTGGGTCGCATCCATTAGTGGTGG TGGTAGCACCTACTATCCAGACAGTGTGAAGGGCC-GATTCACCATCTCCAGAGA TAATGCCAGGAA-CATCCTGTACCTGCAAATGAGCTATCTGAGGTCT-GAGGACAC GGCCGTGTATTACTGTGCAAGAGGAGGGAATATC-TATGATGGTTACCCGTACTA CTTTGAC-TACTGGGGCCAAGGCACCACTCT-CACAGTCTCCTCA (SEQ ID NO: 37), or an equivalent thereof.

Anti-CLDN 18.2 Light Chain Nucleic Acid Sequence (T155S2): GACATTGTGATGACCCAGTCTCCATCCTCCCTGGCTATGTCAGTAGGACAGAAG GTCACTATGAGCTGCAAGTCCAGTCAGAACCTTTTAAATAGTAGCAATCAAAAG AACTATTTGGCCTGGTACCAGCAGAAACCAGGACAGTCTCCTAAACTTCTGGTA TACTTTGCATCCACTAGGGAATCTGGGGTCCCTGATCGCTTCACAGGCAGTGGA TCTGGGACAGATTTCACTCTTACCATCAGCAGTGTGCAGGCTGAAGACCTGGCA GTTTATTACTGTCAGCAACATTATAGCACTCCGCTCACGTTCGGTGCTGGGACC AAGCTGGAGCTGAAA (SEQ ID NO: 39), or an equivalent thereof.

Anti-CLDN 18.2 Heavy Chain Nucleic Acid Sequence (T158S2): GAAGTGAAGCTGGTGGAGTCTGGGGGAGGCTTAGTGCAGCCTGGAGGGTCCCT GAAACTCTCCTGTGCAACCTCTGGATTCACTTTCAGTGACTATTACATGTTTTGG ATTCGCCAGACTCCAGAGAAGAGGCTGGAGTGGGTCGCCTCCATTAGTGATGGT GGTGGTGACACCTATTATCCAGACACTGTAAAGGGCCGATTCACCATCTCCAGA GACAATGCCAAGAACACCCTGTACCTGCAAATGAGCCGTCTGAAGTCTGAGGA CACAGCCATGTATTACTGTGCAAGACATAGGGGCTCTCTTGACTACTGGGGCCA AGGCACCACTCTCACAGTCTCCTCA (SEQ ID NO: 41), or an equivalent thereof.

Anti-CLDN 18.2 Light Chain Nucleic Acid Sequence (T158S2): GACATTGTGCTGACCCAATCTCCAGCTTCTTTGGCTGTGTCTCTAGGGCAGAGG GCCACCATCTCCTGCAGAGCCAGCGAGAGTGTGGATAACTATGGCTTTAGTTTT CTGCACTGGTACCAGCAGAAACCAGGACAGCCACCCAAACTCCTCATCTATCGT GCATCCAACCTAGCATCTGGGATCCCTGCCAGGTTCAGTGGCAGTGGGTCTAGG ACAGACTTCACCCTCACCATTAATCCTGTGGAGACTGATGATGTTGCAACCTAT TACTGTCAGCAAAGTAATCAGGGTCCACTCACGTTCGGTGCTGGGACCAAGCTG GAGCTGAAA (SEQ ID NO: 43), or an equivalent thereof.

Anti-CLDN 18.2 Heavy Chain Nucleic Acid Sequence (T224S8): GAGGTTCAGCTGCAGCAGTCTGGGACAGAGCTTGTGAGGTCAGGGGCCTCAGT CAAGTTGTCCTGCACAACTTCTGGCTTCAACATTAAAGACTACTTTTACACTGG GTGAAGCAGAGGCCTGAACAGGGCCTGGAGTGGATTGGATGGATTGATCCTGA GAATGGTGATACTAAATATGCCCCGAAGTTCCAGGACAAGGTCACCATGACTGT GGACACATCCTCCAACACAGCCTGCCTGCACCTCAGCAGCCTGACATCTGATGA CACTGCCGTCTATTACTGTAATGTACTAGGCTACGGTAATTACGGACATTTTTAC TATGCTATGGACTACTGGGGTCAAGGAACCTCAGTCACCGTCTCCTCT (SEQ ID NO: 45), or an equivalent thereof.

Anti-CLDN 18.2 Light Chain Nucleic Acid Sequence (T224S8): GATGTTGTGATGACCCAAACTCCACTCTCCCTGCCTGTCAGTCTTGGAGATCAG GCCTCCATCTCTTGCAGATCTAGTCAGAGCCTTGTACACAGTAATGGAAACACC TATTTACAT TGGTACCTGCAGAAGCCAGGCCAGTCTCCAAAGCTCCTGATCTAC AAAGTTTCCAACCGATTTTCTGGGGTCCCAGACAGGTTCAGTGGCAGTGAATCA GGGACAGATTTCACACTCAAGATCAGCAGAGTGGAGGCTGAGGATCTGGGAAT TTATTTCTGCTCTCAAAATACACATGTTCCTCGGACGTTCGGTGGAGGCACCAA GCTGGAAATCAGA (SEQ ID NO: 47), or an equivalent thereof.

Anti-CLDN 18.2 Heavy Chain Nucleic Acid Sequence (T192S2): GAAGTGAAGCTGGTGGAGTCTGGGGGAGGCTTAGTGCAGCCTGGAGGGTCCCT GAAACTCTCCTGTGCAACCTCTGGATTCACTTTCAGTGACTATTACATGTATTGG GTTCGCCAGACTCCAGAGAAGAGGCTGGAGTGGGTCGCATACATTAGTAATGG TGGTGGTTCCACCTATTATCCAGACACTGTGAAGGGCCGATTCACCATCTCCAG AGACAATGCCAAGAACACCCTGTACCTGCAAATGAGCCGTCTGAAGTCTGAGG ACACAGCCATGTATTACTGTGCAAGACATAGGGGCTCTCTTGACTTCTGGGGCC AAGGCACCACTCTCACAGTCTCCTCA (SEQ ID NO: 49), or an equivalent thereof.

Anti-CLDN 18.2 Light Chain Nucleic Acid Sequence (T192S2): GACATAGTGCTGACACAGTCTCCTGCTTCCTTAGCTGTATCTCTGGGGCAGAGG GCCACCATCTCCTGCAGAGCCAGCGAAAGTGTTGATAATTATGGCTTTAGTTTT ATGCACTGGTACCAGCAGAAACCAGGACAGCCACCCAAACTCCTCATCTATCGT GCATCCAACCTAGAATCTGGGATCCCTGCCAGGTTCAGTGGCAGTTGGTCTAGG ACAGACTTCACCCTCACCATTAATCCTGTGGAGACTGATGATGTTGCAACCTAT TACTGTCAGCAAAGTAATAAGGTTCCGCTCACGTTCGGTGCTGGGACCAAGCTG GAGCTGAAA (SEQ ID NO: 51), or an equivalent thereof.

Anti-CLDN 18.2 Heavy Chain Nucleic Acid Sequence (T252S4): GAGGTCCAGCTGCAACAGTCTGGACCTGAGCTGGTGAAGCCTGGAGCTTCAAT GAAGATATCCTGCAAGGCTTCTGGTTACTCATTCACTGGCTACAACATGAACTG GGTGAAGCAGACCCATGGAAAGAACCTTGAGTGGATTGGACTTATTAATCCTTA CAATGGTGGTACTAGGTACAACCAGAAGTTCAAGGGCAAGGCCACATTAACTG TAGACAAGTCATCCAGCACAGCCTACATGGAGCTCCTCAGTCTGACATCTGAGG ACTCTGCAGTCTATTTCTGTGCAAGGATGGGACTTGGAAATGCTATGGACTACT GGGGTCAAGGAACCTCAGTCACCGTCTCCTCA (SEQ ID NO: 53), or an equivalent thereof.

Anti-CLDN 18.2 Light Chain Nucleic Acid Sequence (T252S4): GACATTGTGATGACACAGTCTCCATCCTCCCTGACTGTGACAGCAGGAGAGAAG GTCACTATGAGCTGCAAGTCCAGTCAGAATCTGTTAAACAGTGGAAATCAAAA GAACTACTTGACCTGGTACCAGCAGAAACCAGGGCAGCCTCCTAAACTGTTGAT CTACTGGGCATCCACTATGGAATCTGGGGTCCCTGATCGCTTCACAGGCAGTGG ATCTGGAACAGATTTCACTCTCACCATCAGCAGTGTGCAGGCTGAAGACCTGGC AGTTTATTACTGTCAGAATGATTATATT-
TATCCGCTCCCGTTCGGTGCTGGGACC AAGCTG-
GAGCTGAAA (SEQ ID NO: 55), or an equivalent thereof.

Anti-CLDN 18.2 Heavy Chain Nucleic Acid Sequence
(T88S1): CAGGTGCAGCT-
GAAGGAGTCAGGACCTGGCCTGGTGGCGCCCT-
CACAGAGCCT GTCCATCACATGCAC-
CATCTCAGGGTTCTCATTAACCAGCTATGGTATAC-
ACTG GGTTCGCCAGCCTCCAGGAAAGGGTCTG-
GAGTGGCTGGTAGTGATATGGAGTG ATG-
GAAGAACAACCTATAATTCAGCTCTCAAATCCA-
GACTGAGCATCAGCAAG
GACAACTCCAAGAGCCAAGTTTTCTTAAAAAT-
GAACAGTCTCCAAACTGATGAC ACAGCCATGTAC-
TACTGTGCCAGACATGGTAGATACGACCCCTATGC-
TATGGAC
TACTGGGGTCAAGGAACCTCAGT-
CACCGTCTCCTCA (SEQ ID NO: 57), or an equivalent
thereof.

Anti-CLDN 18.2 Light Chain Nucleic Acid Sequence
(T88S1): GACATTGTGCTGACC-
CAATCTCCAGCTTCTTTGGCTGTGTCTCTAGGGCA-
GAGG GCCAC-
CATCTCCTGCAGAGCCAGCGAGAGTGTGGATAAC-
TATGGCTTTAGTTTT
CTGCACTGGTACCAGCAGAAACCAGGACAGC-
CACCCAAACTCCTCATCTATCGT GCATC-
CAACCTAGCATCTGG-
GATCCCTGCCAGGTTCAGTGGCAGTGGGTCTAGG
ACAGACTTCACCCTCACCATTAATCCTGTGGA-
GACTGATGATGTTGCAACCTAT
TACTGTCAGCAAAGTAATCAGGGTCCACT-
CACGTTCGGTGCTGGGACCAAGCTG GAGCTGAAA
(SEQ ID NO: 43), or an equivalent thereof.

Anti-CLDN 18.2 Chimeric Heavy Chain Nucleic Acid
Sequence (T252S4):

```
                                        (SEQ ID NO: 53)
GAGGTCCAGCTGCAACAGTCTGGACCTGAGCTGGTGAAGCCTGGAGCTTC

AATGAAGATATCCTGCAAGGCTTCTGGTTACTCATTCACTGGCTACAACA

TGAACTGGGTGAAGCAGACCCATGGAAAGAACCTTGAGTGGATTGGACTT

ATTAATCCTTACAATGGTGGTACTAGGTACAACCAGAAGTTCAAGGGCAA

GGCCACATTAACTGTAGACAAGTCATCCAGCACAGCCTACATGGAGCTCC

TCAGTCTGACATCTGAGGACTCTGCAGTCTATTTCTGTGCAAGGATGGGA

CTTGGAAATGCTATGGACTACTGGGGTCAAGGAACCTCAGTCACCGTCTC

CTCA
```

Anti-CLDN 18.2 Humanized Heavy Chain Nucleic Acid
Sequence 1 (Hu VH1 T252S4):

```
                                        (SEQ ID NO: 69)
GAAGTCCAGCTCGTGCAGTCTGGTGCGGAGGTCAAAAAACCCGGCGAGTC

TCTCAAAATTAGTTGCAAAGGCTCCGGTTATTCATTCACGGGTTACAATA

TGAACTGGGTTCGACAAATGCCGGGTAAGGGACTTGAATGGATGGGATTG

ATCAACCCCTATAACGGAGGTACCAGATACAACCAAAAATTTAAGGGCCA

GGTGACTATTAGTGCAGATAAAAGTATCTCCACCGCTTACCTCCAATGGT
```

CTAGTTTGAAGGCGTCTGACACTGCTATGTACTTTTGCGCGAGAATGGGG

TTGGGAAATGCGATGGACTACTGGGGTCAGGGCACTACGGTTACGGTCTC

CTCT

Anti-CLDN 18.2 Humanized Heavy Chain Nucleic Acid
Sequence 2 (Hu VH2 T252S4):

```
                                        (SEQ ID NO: 70)
GAGGTACAGCTCGTGCAATCTGGGGCCGAAGTAAAGAAACCTGGAGAAAG

TCTTAAAATAAGCTGCAAGGGCAGTGGGTATAGCTTCACGGGCTACAATA

TGAACTGGGTTAGACAAATGCCAGGTAAGAACCTCGAATGGATAGGATTG

ATCAACCCATACAATGGTGGTACGCGCTACAACCAGAAATTCAAAGGTCA

GGTTACCATCTCTGCGGATAAAAGCATCTCAACGGCGTATCTTCAATGGT

CCTCACTGAAAGCATCCGACACAGCAATGTATTTTTGCGCTAGAATGGGA

TTGGGTAATGCCATGGACTACTGGGGCCAAGGCACCACGGTTACAGTCTC

TTCC
```

Anti-CLDN 18.2 Humanized Heavy Chain Nucleic Acid
Sequence 3 (Hu VH3 T252S4):

```
                                        (SEQ ID NO: 71)
GAAGTTCAGCTGGTGCAAAGTGGGCTGAGGTAAAGAAGCCTGGCGAGAG

CCTCAAGATTTCTTGCAAGGGTAGCGGATACAGTTTTACGGGATATAACA

TGAATTGGGTTCGCCAGATGCCGGGGAAGAACCTTGAATGGATAGGACTG

ATAAACCCCTATAATGGGGAACCCGATATAATCAGAAGTTTAAGGGAAA

AGCAACTTTGTCAGTTGACAAGTCTATCAGCACGGCCTATCTTCAGTGGT

CCAGTCTGAAAGCAAGCGACACGGCTATGTACTTTTGTGCACGCATGGGG

CTTGGTAACGCAATGGACTATTGGGGACAAGGAACTACCGTCACTGTCTC

TTCA
```

Anti-CLDN 18.2 Chimeric Light Chain Nucleic Acid
Sequence 3 (Chimeric VL T252S4):

```
                                        (SEQ ID NO: 55)
GACATTGTGATGACACAGTCTCCATCCTCCCTGACTGTGACAGCAGGAGA

GAAGGTCACTATGAGCTGCAAGTCCAGTCAGAATCTGTTAAACAGTGGAA

ATCAAAAGAACTACTTGACCTGGTACCAGCAGAAACCAGGGCAGCCTCCT

AAACTGTTGATCTACTGGGCATCCACTATGGAATCTGGGGTCCCTGATCG

CTTCACAGGCAGTGGATCTGGAACAGATTTCACTCTCACCATCAGCAGTG

TGCAGGCTGAAGACCTGGCAGTTTATTACTGTCAGAATGATTATATTTAT

CCGCTCCCGTTCGGTGCTGGGACCAAGCTGGAGCTGAAA
```

Anti-CLDN 18.2 Humanized Light Chain Nucleic Acid
Sequence 1 (Hu VL1 T252S4):

```
                                        (SEQ ID NO: 73)
GACATCGTGATGACCCAGTCCCCGGACAGTCTGGCAGTCAGTCTTGGGGA

AAGAGCTACCATAAACTGCAAATCCAGCCAAAACCTTCTTAATAGCGGCA

ACCAAAAGAATTACTTGACTTGGTATCAGCAAAAACCGGGTCAGCCGCCC
```

-continued
AAACTCTTGATATACTGGGCGTCTACGATGGAAAGCGGCGTCCCCGACCG

CTTCAGCGGGAGTGGGTCAGGGACTGATTTCACTTTGACAATCAGTTCCC

TTCAGGCAGAGGACGTAGCAGTCTACTACTGTCAGAATGATTATATATAT

CCTCTTCCGTTCGGCCAGGGGACGAAGTTGGAGATCAAA

Anti-CLDN 18.2 Humanized Light Chain Nucleic Acid Sequence 3 (Hu VL2 T252S4):

(SEQ ID NO: 74)
GACATCGTGATGACTCAAAGTCCTGACTCCCTTGCTGTTTCACTTGGCGA

AAGGGCCACTATCAACTGTAAGAGTTCTCAGAATCTCTTGCAATCAGGAA

ACCAGAAGAATTACTTGACCTGGTATCAACAGAAGCCTGGACAACCACCT

AAGCTCTTGATTTACTGGGCTAGTACAAGGGAGTCCGGCGTCCCAGACAG

ATTTTCCGGTTCTGGATCAGGCACGGACTTCACTCTGACAATCTCTAGTC

TTCAAGCCGAGGATGTGGCCGTTTATTATTGCCAGAACGATTACATTTAC

CCTTTGCCATTTGGTCAAGGTACTAAGTTGGAGATAAAA

In one aspect, humanized antibodies having the above-identified VH and VL combinations also are provided in Table 4.

In one aspect, the disclosure provides an isolated anti-CLDN 18.2 antibody which is generated against a CLDN 18.2 fragment.

In another aspect of the present technology, the isolated antibody includes one or more of the following characteristics:
  (a) the light chain immunoglobulin variable domain sequence comprises one or more CDRs that are at least 85% identical to a CDR of a light chain variable domain of any of the disclosed light chain sequences;
  (b) the heavy chain immunoglobulin variable domain sequence comprises one or more CDRs that are at least 85% identical to a CDR of a heavy chain variable domain of any of the disclosed heavy chain sequences;
  (c) the light chain immunoglobulin variable domain sequence is at least 85% identical to a light chain variable domain of any of the disclosed light chain sequences;
  (d) the HC immunoglobulin variable domain sequence is at least 85% identical to a heavy chain variable domain of any of the disclosed light chain sequences; and
  (e) the antibody binds an epitope that overlaps with an epitope bound by any of the disclosed sequences.

In one aspect, the present disclosure provides an isolated antibody that is at least 85% identical to the anti-CLDN 18.2 antibody disclosed herein.

In some of the aspects of the antibodies provided herein, the antibody binds human CLDN 18.2 with a dissociation constant ($K_D$) of less than $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In some of the aspects of the antibodies provided herein, the antigen binding site specifically binds to human CLDN 18.2.

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In another embodiment, the antibody is a monoclonal antibody comprising an anti-CLDN 18.2 heavy chain variable region comprising, or alternatively consisting essentially of, or yet further consisting of a polypeptide selected disclosed herein or an equivalent of each thereof, and an anti-CLDN 18.2 light chain variable region comprising, or alternatively consisting essentially of, or yet further consisting of a polypeptide disclosed herein or an equivalent of each thereof.

In another aspect, the anti-CLDN 18.2 antibody is a chimeric antibody, human or a humanized antibody.

In some of the aspects of the antibodies provided herein, the antibody is a monoclonal antibody.

In some of the aspects of the antibodies provided herein, the antibody is a full-length antibody. In other aspect, antigen binding fragments of the antibodies are provided.

In some of the aspects of the antibodies provided herein, the antibody fragment is selected from the group consisting of Fab, F(ab)'2, Fab', scF$_v$, and F$_v$.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families:
  1) Amino acids with basic side chains: lysine, arginine, histidine;
  2) Amino acids with acidic side chains: aspartic acid, glutamic acid;
  3) Amino acids with uncharged polar side chains: asparagine, glutamine, serine, threonine, tyrosine;
  4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising such varied CDR sequences still bind CLDN 18.2 with similar specificity and sensitivity profiles as the disclosed antibodies. This may be tested by way of the binding assays.

The constant regions of antibodies may also be varied. For example, antibodies may be provided with Fc regions of any isotype: IgA (IgA1, IgA2), IgD, IgE, IgG (IgG1, IgG2, IgG3, IgG4) or IgM.

Human IgD constant region, Uniprot: P01880 APTKAP-DVFPIISGCRHPKDNSPVVLA-CLITGYHPTSVTVTWYMGTQSQPQRTFPEI QRRDSYYMTSSQLSTPLQQWRQGEYKCVVQH-TASKSKKEIFRWPESPKAQASSVP TAQPQAE-GSLAKATTAPATTRNTGRGGEEKKKEKEKE-EQEERETKTPECPSHTQPL GVYLLTPAVQDLWLRDKATFTCFVVGSDLKDAHL-TWEVAGKVPTGGVEEGLLER HSNGSQSQHSRLTL-PRSLWNAGTSVTCTLNHPSLPPQRLMAL-REPAAQAPVKLSLN LLASSDPPEAASWLLCEVSGFSPPNILL-MWLEDQREVNTSGFAPARPPPQPGSTTFW AWSVLRVPAPPSPQPATYTCVVSHEDSRTLLNAS-RSLEVSYVTDHGPMK (SEQ ID NO: 99), or an equivalent thereof.

Human IgG1 constant region, Uniprot: P01857 ASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSCDKTHTCPPCPA PELLGGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK (SEQ ID NO: 100), or an equivalent thereof.

Human IgG2 constant region, Uniprot: P01859 ASTKGPSVFPLAPCSRSTSESTAALGCLVKDYFPEPVTVSWNSGALTSGVHTFPAVL QSSGLYSLSSVVTVPSSNFGTQTYTCNVDHKPSNTKVDKTVERKCCVECPPCPAPP VAGPSVFLFPPKPKDTLMISRTPEVTCVVVDVSHEDPEVQFNWYVDGVEVHNAKT KPREEQFNSTFRVVSVLTVVHQDWLNGKEYKCKVSNKGLPAPIEKTISKTKGQPRE PQVYTLPPSREEMTKNQVSLTCLVKGFYPSDISVEWESNGQPENNYKTTPPMLDSD GSFFLYSKLTVDKSRWQQGNVFSCSVMHEALHNHYTQKSLSLSPGK (SEQ ID NO: 101), or an equivalent thereof.

Human IgG3 constant region, Uniprot: P01860 ASTKGPSVFPLAPCSRSTSGGTAALGCLVKDYFPEPVTVSWNSGALTSGVHTFPAV LQSSGLYSLSSVVTVPSSSLGTQTYTCNVNHKPSNTKVDKRVELKTPLGDTTHTCPR CPEPKSCDTPPPCPRCPEPKSCDTPPPCPRCPEPKSCDTPPPCPRCPAPELLGGPSVFL FPPKPKDTLMISRTPEVTCVVVDVSHEDPEVQFKWYVDGVEVHNAKTKPREEQYN STFRVVSVLTVLHQDWLNGKEYKCKVSNKALPAPIEKTISKTKGQPREPQVYTLPPS REEMTKNQVSLTCLVKGFYPSDIAVEWESSGQPENNYNTTPPMLDSDGSFFLYSKL TVDKSRWQQGNIFSCSVMHEALHNRFTQKSLSLSPGK (SEQ ID NO: 102), or an equivalent thereof.

Human IgM constant region, Uniprot: P01871 GSASAPTLFPLVSCENSPSDTSSVAVGCLAQDFLPDSITLSWKYKNNSDISSTRGFPS VLRGGKYAATSQVLLPSKDVMQGTDEHVVCKVQHPNGNKEKNVPLPVIAELPPKV SVFVPPRDGFFGNPRKSKLICQATGFSPRQIQVSWLREGKQVGSGVTTDQVQAEAK ESGPTTYKVTSTLTIKESDWLGQSMFTCRVDHRGLTFQQNASSMCVPDQDTAIRVF AIPPSFASIFLTKSTKLTCLVTDLTTYDSVTISWTRQNGEAVKTHTNISESHPNATFSA VGEASICEDDWNSGERFTCTVTHTDLPSPLKQTISRPKGVALHRPDVYLLPPAREQL NLRESATITCLVTGFSPADVFVQWMQRGQPLSPEKYVTSAPMPEPQAPGRYFAHSIL TVSEEEWNTGETYTCVAHEALPNRVTERTVDKSTGKPTLYNVSLVMSDTAGTCY (SEQ ID NO: 103), or an equivalent thereof.

Human IgG4 constant region, Uniprot: P01861 ASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPSCPAPEF LGGPSVFLFPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTISKAKGQPRE PQVYTLPPSQEEMTKNQVSLTCLVKGFYPSDIAVEWESNGQPENNYKTTPPVLDSD GSFFLYSRLTVDKSRWQEGNVFSCSVMHEALHNHYTQKSLSLSLGK (SEQ ID NO: 104), or an equivalent thereof.

Human IgA1 constant region, Uniprot: P01876 ASPTSPKVFPLSLCSTQPDGNVVIACLVQGFFPQEPLSVTWSESGQGVTARNFPPSQ DASGDLYTTSSQLTLPATQCLAGKSVTCHVKHYTNPSQDVTVPCPVPSTPPTPSPST PPTPSPSCCHPRLSLHRPALEDLLLGSEANLTCTLTGLRDASGVTFTWTPSSGKSAV QGPPERDLCGCYSVSSVLPGCAEPWNHGKTFTCTAAYPESKTPLTATLSKSGNTFRP EVHLLPPPSEELALNELVTLTCLARGFSPKDVLVRWLQGSQELPREKYLTWASRQE PSQGTTTFAVTSILRVAAEDWKKGDTFSCMVGHEALPLAFTQKTIDRLAGKPTHVN VSVVMAEVDGTCY (SEQ ID NO: 105), or an equivalent thereof.

Human IgA2 constant region, Uniprot: P01877 ASPTSPKVFPLSLDSTPQDGNVVVACLVQGFFPQEPLSVTWSESGQNVTARNFPPSQ DASGDLYTTSSQLTLPATQCPDGKSVTCHVKHYTNPSQDVTVPCPVPPPPCCHPRL SLHRPALEDLLLGSEANLTCTLTGLRDASGATFTWTPSSGKSAVQGPPERDLCGCY SVSSVLPGCAQPWNHGETFTCTAAHPELKTPLTANITKSGNTFRPEVHLLPPPSEEL ALNELVTLTCLARGFSPKDVLVRWLQGSQELPREKYLTWASRQEPSQGTTTFAVTS ILRVAAEDWKKGDTFSCMVGHEALPLAFTQKTIDRMAGKPTHVNVSVVMAEVDG TCY (SEQ ID NO: 106), or an equivalent thereof.

Human Ig kappa constant region, Uniprot: P01834 SEQ ID NO: 107 TVAAPSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGEC (SEQ ID NO: 107), or an equivalent thereof.

In some aspects of the antibodies provided herein, the antibody contains structural modifications to facilitate rapid binding and cell uptake and/or slow release. In some aspects, the CLDN 18.2 antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

The antibodies, fragments, and equivalents thereof can be combined with a carrier, e.g., a pharmaceutically acceptable carrier or other agents to provide a formulation for use and/or storage.

Further provided is an isolated polypeptide comprising, or alternatively consisting essentially of, or yet further consisting of, the amino acid sequence of CLDN 18.2 or a fragment thereof, that are useful to generate antibodies that bind to CLDN 18.2, as well as isolated polynucleotides that encode them. In one aspect, the isolated polypeptides or polynucleotides further comprise a label and/or contiguous polypeptide sequences (e.g., keyhole limpet haemocyanin (KLH) carrier protein) or in the case of polynucleotides, polynucleotides encoding the sequence, operatively coupled to polypeptide or polynucleotide. The polypeptides or polynucleotides can be combined with various carriers, e.g., phosphate buffered saline. Further provided are host cells, e.g., prokaryotic or eukaryotic cells, e.g., bacteria, yeast, mammalian (rat, simian, hamster, or human), comprising the isolated polypeptides or polynucleotides. The host cells can be combined with a carrier.

Yet further provided are the isolated nucleic acids encoding the antibodies and fragments thereof as disclosed herein. They can be combined with a vector or appropriate host cell, and/or a suitable carrier for diagnostic or therapeutic use. In one aspect, the nucleic acids are contained with a host cell for recombinant production of polypeptides and proteins. The host cells can be eukaryotic or prokaryotic.

II. Processes for Preparing Compositions

Antibodies, their manufacture and uses are well known and disclosed in, for example, Harlow, E. and Lane, D., Antibodies: A Laboratory Manual, Cold Spring Harbor Laboratory Press, Cold Spring Harbor, N.Y., 1999. The antibodies may be generated using standard methods known in the art. Examples of antibodies include (but are not limited to) monoclonal, single chain, and functional fragments of antibodies.

Antibodies may be produced in a range of hosts, for example goats, rabbits, rats, mice, humans, and others. They may be immunized by injection with a target antigen or a fragment or oligopeptide thereof which has immunogenic properties, such as an N-terminal or C-terminal fragment of CLDN 18.2 or an isolated polypeptide. Depending on the host species, various adjuvants may be added and used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (Bacille Calmette-Guerin) and *Corynebacterium parvum* are particularly useful. Thus, this disclosure also provides the isolated polypeptide and an adjuvant.

In certain aspects, the antibodies of the present disclosure are polyclonal, i.e., a mixture of plural types of anti-CLDN 18.2 antibodies having different amino acid sequences. In one aspect, the polyclonal antibody comprises a mixture of plural types of anti-CLDN 18.2 antibodies having different CDRs. As such, a mixture of cells which produce different antibodies is cultured, and an antibody purified from the resulting culture can be used (see WO 2004/061104).

Monoclonal Antibody Production. Monoclonal antibodies to CLDN 18.2 may be prepared using any technique which provides for the production of antibody molecules by continuous cell lines in culture. Such techniques include, but are not limited to, the hybridoma technique (see, e.g., Kohler & Milstein, Nature 256: 495-497 (1975)); the trioma technique; the human B-cell hybridoma technique (see, e.g., Kozbor, et al., Immunol. Today 4: 72 (1983)) and the EBV hybridoma technique to produce human monoclonal antibodies (see, e.g., Cole, et al., in: MONOCLONAL ANTIBODIES AND CANCER THERAPY, Alan R. Liss, Inc., pp. 77-96 (1985)). Human monoclonal antibodies can be utilized in the practice of the present technology and can be produced by using human hybridomas (see, e.g., Cote, et al., Proc. Natl. Acad. Sci. 80: 2026-2030 (1983)) or by transforming human B-cells with Epstein Barr Virus in vitro (see, e.g., Cole, et al., in: MONOCLONAL ANTIBODIES AND CANCER THERAPY, Alan R. Liss, Inc., pp. 77-96 (1985)).

For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the CLDN 18.2 polypeptide. Alternatively, hybridomas expressing anti-CLDN 18.2 monoclonal antibodies can be prepared by immunizing a subject, e.g., with an isolated polypeptide comprising, or alternatively consisting essentially of, or yet further consisting of, the amino acid sequence of CLDN 18.2 or a fragment thereof, and then isolating hybridomas from the subject's spleen using routine methods. See, e.g., Milstein et al., (Galfre and Milstein, Methods Enzymol 73: 3-46 (1981)). Screening the hybridomas using standard methods will produce monoclonal antibodies of varying specificity (i.e., for different epitopes) and affinity. A selected monoclonal antibody with the desired properties, e.g., CLDN 18.2 binding, can be (i) used as expressed by the hybridoma, (ii) bound to a molecule such as polyethylene glycol (PEG) to alter its properties, or (iii) a cDNA encoding the monoclonal antibody can be isolated, sequenced and manipulated in various ways. In one aspect, the anti-CLDN 18.2 monoclonal antibody is produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., Antibodies: A Laboratory Manual Cold Spring Harbor Laboratory, Cold Spring Harbor, N.Y., 349 (1988); Hammerling et al., Monoclonal Antibodies And T-Cell Hybridomas, 563-681 (1981).

Phage Display Technique. As noted above, the antibodies of the present disclosure can be produced through the application of recombinant DNA and phage display technology. For example, anti-CLDN 18.2 antibodies, can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g., human or murine) by selecting directly with an antigen, typically an antigen bound or captured to a solid surface or bead. Phage used in these methods are typically filamentous phage including fd and M13 with Fab, $F_v$ or disulfide stabilized $F_v$ antibody domains are recombinantly fused to either the phage gene III or gene VIII protein. In addition, methods can be adapted for the construction of Fab expression libraries (see, e.g., Huse, et al., Science 246: 1275-1281, 1989) to allow rapid and effective identification of monoclonal Fab fragments with the desired specificity for a CLDN 18.2 polypeptide, e.g., a polypeptide or derivatives, fragments, analogs or homologs thereof. Other examples of phage display methods that can be used to make the isolated antibodies of the present disclosure include those disclosed in Huston et al., Proc. Natl. Acad. Sci. U.S.A., 85: 5879-5883 (1988); Chaudhary et al., Proc. Natl. Acad. Sci. U.S.A., 87: 1066-1070 (1990); Brinkman et al., J. Immunol. Methods 182: 41-50 (1995);

Ames et al., J. Immunol. Methods 184: 177-186 (1995); Kettleborough et al., Eur. J. Immunol. 24: 952-958 (1994); Persic et al., Gene 187: 9-18 (1997); Burton et al., Advances in Immunology 57: 191-280 (1994); PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., BioTechniques 12: 864-869 (1992); Sawai et al., AJRI 34: 26-34 (1995); and Better et al., Science 240: 1041-1043 (1988).

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See e.g. Barbas III et al., Phage Display, A Laboratory Manual (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Alternate Methods of Antibody Production. Antibodies may also be produced by inducing in vivo production in the lymphocyte population or by screening recombinant immunoglobulin libraries or panels of highly specific binding reagents (Orlandi et al., PNAS 86: 3833-3837 (1989); Winter, G. et al., Nature, 349: 293-299 (1991)).

Alternatively, techniques for the production of single chain antibodies may be used. Single chain antibodies (scF$_v$s) comprise a heavy chain variable region and a light chain variable region connected with a linker peptide (typically around 5 to 25 amino acids in length). In the scF$_v$, the variable regions of the heavy chain and the light chain may be derived from the same antibody or different antibodies. scF$_v$s may be synthesized using recombinant techniques, for example by expression of a vector encoding the scF$_v$ in a host organism such as E. coli. DNA encoding scF$_v$ can be obtained by performing amplification using a partial DNA encoding the entire or a desired amino acid sequence of a DNA selected from a DNA encoding the heavy chain or the variable region of the heavy chain of the above-mentioned antibody and a DNA encoding the light chain or the variable region of the light chain thereof as a template, by PCR using a primer pair that defines both ends thereof, and further performing amplification combining a DNA encoding a polypeptide linker portion and a primer pair that defines both ends thereof, so as to ligate both ends of the linker to the heavy chain and the light chain, respectively. An expression vector containing the DNA encoding scF$_v$ and a host transformed by the expression vector can be obtained according to conventional methods known in the art.

Antigen binding fragments may also be generated, for example the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., Science, 256: 1275-1281 (1989)).

Antibody Modifications. The antibodies of the present disclosure may be multimerized to increase the affinity for an antigen. The antibody to be multimerized may be one type of antibody or a plurality of antibodies which recognize a plurality of epitopes of the same antigen. As a method of multimerization of the antibody, binding of the IgG CH3 domain to two scF$_v$ molecules, binding to streptavidin, introduction of a helix-turn-helix motif and the like can be exemplified.

The antibody compositions disclosed herein may be in the form of a conjugate formed between any of these antibodies and another agent (such as an antibody drug conjugate (ADC) or an immunoconjugate). Non-limiting examples suitable to conjugate or fuse with the antibodies disclosed herein include therapeutic agents, e.g. detectable labels such as radioactive labels, an immunomodulator, a hormone, an enzyme, an oligonucleotide, a photoactive therapeutic or diagnostic agent, a cytotoxic agent, a drug or a toxin, an ultrasound enhancing agent, a non-radioactive label, a combination thereof and other such agents known in the art. In some embodiments, the antibodies may be conjugated to therapeutic agents, prodrugs, peptides, proteins, enzymes, viruses, lipids, biological response modifiers, pharmaceutical agents, and/or polyethylene glycol (PEG).

Bispecific Antibodies. CLDN 18.2 is over-expressed in cancer tissues but has restricted off-target positivity. It is contemplated that bi-functional molecules that combine an anti-CLDN 18.2 antibody or fragment with another molecule or fragment that has specificity (second specificity) to a cytokine, an immune checkpoint, or a cancer or tumor antigen would have synergistic effect in treatments. Thus, the antibody compositions disclosed herein may be in the form of a bispecific antibody comprising the binding domain of the disclosed antibody and the binding domain with a second specificity. In some embodiments, the second specificity is to a molecule selected from IL-1, CD3, CD16, CD19, CD28, and CD64. Other examples include PD-1, PD-L1, CTLA-4, LAG-3 (also known as CD223), CD28, CD122, 4-1BB (also known as CD137), TIM3, OX-40 or OX40L, CD40 or CD40L, CD47, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs). An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP and Tenascin.

Different formats of bispecific antibodies are also provided. In some embodiments, each of the anti-CLDN 18.2 fragment and the second fragment each is independently selected from a Fab fragment, a single-chain variable fragment (scF$_v$), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to CLDN 18.2, such as those described here, can be combined with an immune cytokine or ligand optionally through a peptide linker. The linked immune cytokines or ligands include, but not limited to, IL-1, IL-2, IL-3, IL-4, IL-5, IL-6, IL-7, IL-10, IL-12, IL-13, IL-15, GM-CSF, TNF-alpha, CD40L, OX40L, CD27L, CD30L, 4-1BBL, LIGHT and GITRL. Such bi-functional molecules can lead to specific tumor site local immune modulation.

Antibody Screening. Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between CLDN 18.2, or any fragment or oligopeptide thereof and its specific antibody. A two-site, monoclonal-based immunoassay utilizing monoclonal antibodies specific to two non-interfering CLDN 18.2 epitopes may be used, but a competitive binding assay may also be employed (Maddox et al., J. Exp. Med., 158: 1211-1216 (1983)).

Automated immunohistochemistry (IHC) screening of potential anti-CLDN 18.2 antibodies can be performed using a Ventana Medical Systems, Inc (VMSI) Discovery XT and formalin-fixed, paraffin-embedded human tissue on glass slides. Tissue samples first undergo deparaffinization, antigen retrieval, followed by the addition of the potential anti-CLDN 18.2 antibody and a detection antibody. The detection antibody is visualized using a chromogen detection reagent from VMSI. Stained slides are manually screened under a microscope. Samples having a correct primary antibody staining pattern are selected as potential anti-CLDN 18.2 candidates.

Antibody Purification. The antibodies disclosed herein can be purified to homogeneity. The separation and purification of the antibodies can be performed by employing conventional protein separation and purification methods.

By way of example only, the antibody can be separated and purified by appropriately selecting and combining use of chromatography columns, filters, ultrafiltration, salt precipitation, dialysis, preparative polyacrylamide gel electrophoresis, isoelectric focusing electrophoresis, and the like. Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988).

Examples of chromatography include affinity chromatography, ion exchange chromatography, hydrophobic chromatography, gel filtration chromatography, reverse phase chromatography, and adsorption chromatography. In one aspect, chromatography can be performed by employing liquid chromatography such as HPLC or FPLC.

In one aspect, a Protein A column or a Protein G column may be used in affinity chromatography. Other exemplary columns include a Protein A column, Hyper D, POROS, Sepharose F. F. (Pharmacia) and the like.

CAR T-cells are genetically engineered autologous T-cells in which single chain antibody fragments (scFv) or ligands are attached to the T-cell signaling domain capable of facilitating T-cell activation (Maher, J. (2012) ISRN Oncol. 2012:278093; Curran, K. J. et al. (2012) J. Gene Med. 14:405-415; Fedorov, V. D. et al. (2014) Cancer J. 20:160-165; Barrett, D. M. et al. (2014) Annu. Rev. Med. 65:333-347). CARs combine HLA-independent targeting specificity of a monoclonal antibody with the cytolytic activity and homing properties of activated T-cells. These properties enable the recognition of target cells with reduced HLA expression or down-regulated antigen processing pathways, two common methods tumors employ to evade the host immune response (Jakobsen, M. K. et al. (1995) J. Immunother. Emphasis Tumor Immunol. 17:222-228; Lou, Y. et al. (2008) Clin. Cancer Res. 14:1494-1501; Singh, R. et al. (2007) Cancer Res. 67:1887-1892). CAR-modified T-cells have shown great promise in preclinical and clinical settings as novel therapeutics in various diseases including ovarian carcinomas (Chu, C. S. et al. (2008) Expert Rev. Anticancer Ther. 8:243-257; Chekmasova, A. A. et al. (2010) Discov. Med. 9:62-70; Porter, D. L. et al. (2011) NEJM 365:725-733). To date, CAR T-cells generated against a variety of targets. In addition, antibodies to CLDN 18.2 have been disclosed and approved for treatment of certain cancers. Consistent with these principles and discoveries, this disclosure provides the following embodiments.

III. Methods of Use

General. The antibodies disclosed herein are useful in methods known in the art relating to the localization and/or quantitation of a CLDN 18.2 polypeptide (e.g., for use in measuring levels of the CLDN 18.2 polypeptide within appropriate physiological samples, for use in diagnostic methods, for use in imaging the polypeptide, and the like). The antibodies disclosed herein are useful in isolating a CLDN 18.2 polypeptide by standard techniques, such as affinity chromatography or immunoprecipitation. A CLDN 18.2 antibody disclosed herein can facilitate the purification of natural CLDN 18.2 polypeptides from biological samples, e.g., mammalian sera or cells as well as recombinantly-produced CLDN 18.2 polypeptides expressed in a host system. Moreover, CLDN 18.2 antibody can be used to detect a CLDN 18.2 polypeptide (e.g., in plasma, a cellular lysate or cell supernatant) in order to evaluate the abundance and pattern of expression of the polypeptide. The CLDN 18.2 antibodies disclosed herein can be used diagnostically to monitor CLDN 18.2 levels in tissue as part of a clinical testing procedure, e.g., to determine the efficacy of a given treatment regimen and/or to determine and identify subjects or patient who are most likely to respond to the treatment because the tumors or cancer cells express the antigen. The detection can be facilitated by coupling (i.e., physically linking) the CLDN 18.2 antibodies disclosed herein to a detectable substance.

In another aspect, provided herein is a composition comprising an antibody or antigen binding fragment as disclosed herein bound to a peptide comprising, for example, a human CLDN 18.2 protein or a fragment thereof. In one aspect, the peptide is associated with a cell. For example, the composition may comprise a disaggregated cell sample labeled with an antibody or antibody fragment as disclosed herein, which composition is useful in, for example, affinity chromatography methods for isolating cells or for flow cytometry-based cellular analysis or cell sorting. As another example, the composition may comprise a fixed tissue sample or cell smear labeled with an antibody or antibody fragment as disclosed herein, which composition is useful in, for example, immunohistochemistry or cytology analysis. In another aspect, the antibody or the antibody fragment is bound to a solid support, which is useful in, for example: ELISAs; affinity chromatography or immunoprecipitation methods for isolating CLDN 18.2 proteins or fragments thereof, CLDN 18.2-positive cells, or complexes containing CLDN 18.2 and other cellular components. In another aspect, the peptide is bound to a solid support. For example, the peptide may be bound to the solid support via a secondary antibody specific for the peptide, which is useful in, for example, sandwich ELISAs. As another example, the peptide may be bound to a chromatography column, which is useful in, for example, isolation or purification of antibodies according to the present technology. In another aspect, the peptide is disposed in a solution, such as a lysis solution or a solution containing a sub-cellular fraction of a fractionated cell, which is useful in, for example, ELISAs and affinity chromatography or immunoprecipitation methods of isolating CLDN 18.2 proteins or fragments thereof or complexes containing CLDN 18.2 and other cellular components. In another aspect, the peptide is associated with a matrix, such as, for example, a gel electrophoresis gel or a matrix commonly used for western blotting (such as membranes made of nitrocellulose or polyvinylidene difluoride), which compositions are useful for electrophoretic and/or immunoblotting techniques, such as Western blotting.

Detection of CLDN 18.2 Polypeptide. An exemplary method for detecting the level of CLDN 18.2 polypeptides in a biological sample involves obtaining a biological sample from a subject and contacting the biological sample with a CLDN 18.2 antibody disclosed herein which is capable of detecting the CLDN 18.2 polypeptides.

In one aspect, the CLDN 18.2 antibodies T155S2, T158S2, T224S8, T192S2, and T252S4, or fragments thereof are detectably labeled. The term "labeled", with regard to the antibody is intended to encompass direct labeling of the antibody by coupling (i.e., physically linking) a detectable substance to the antibody, as well as indirect labeling of the antibody by reactivity with another compound that is directly labeled. Non-limiting examples of indirect labeling include detection of a primary antibody using a fluorescently-labeled secondary antibody and end-labeling of a DNA probe with biotin such that it can be detected with fluorescently-labeled streptavidin.

The detection method of the present disclosure can be used to detect expression levels of CLDN 18.2 polypeptides in a biological sample in vitro as well as in vivo. In vitro techniques for detection of CLDN 18.2 polypeptides include enzyme linked immunosorbent assays (ELISAs), Western blots, flow cytometry, immunoprecipitations, radioimmunoassay, and immunofluorescence (e.g., IHC). Furthermore, in vivo techniques for detection of CLDN 18.2 polypeptides include introducing into a subject a labeled anti-CLDN 18.2 antibody. By way of example only, the antibody can be labeled with a radioactive marker whose presence and location in a subject can be detected by standard imaging techniques. In one aspect, the biological sample contains polypeptide molecules from the test subject.

Immunoassay and Imaging. A CLDN 18.2 antibody disclosed herein can be used to assay CLDN 18.2 polypeptide levels in a biological sample (e.g. human plasma) using antibody-based techniques. For example, protein expression in tissues can be studied with classical immunohistochemical (IHC) staining methods. Jalkanen, M. et al., J. Cell. Biol. 101: 976-985 (1985); Jalkanen, M. et al., J. Cell. Biol. 105: 3087-3096 (1987). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agents, such as iodine ($^{125}$I, $^{121}$I, $^{131}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin.

In addition to assaying CLDN 18.2 polypeptide levels in a biological sample, CLDN 18.2 polypeptide levels can also be detected in vivo by imaging. Labels that can be incorporated with anti-CLDN 18.2 antibodies for in vivo imaging of CLDN 18.2 polypeptide levels include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the CLDN 18.2 antibody by labeling of nutrients for the relevant scF$_v$ clone.

A CLDN 18.2 antibody which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled CLDN 18.2 antibody will then preferentially accumulate at the location of cells which contain the specific target polypeptide. For example, in vivo tumor imaging is described in S. W. Burchiel et al., Tumor Imaging: The Radiochemical Detection of Cancer 13 (1982).

In some aspects, CLDN 18.2 antibodies containing structural modifications that facilitate rapid binding and cell uptake and/or slow release are useful in in vivo imaging detection methods. In some aspects, the CLDN 18.2 antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

Diagnostic Uses of CLDN 18.2 antibodies. The CLDN 18.2 antibody compositions disclosed herein are useful in diagnostic and prognostic methods. As such, the present disclosure provides methods for using the antibodies disclosed herein in the diagnosis of CLDN 18.2-related medical conditions in a subject. Antibodies disclosed herein may be selected such that they have a high level of epitope binding specificity and high binding affinity to the CLDN 18.2 polypeptide. In general, the higher the binding affinity of an antibody, the more stringent wash conditions can be performed in an immunoassay to remove nonspecifically bound material without removing the target polypeptide. Accordingly, CLDN 18.2 antibodies of the present technology useful in diagnostic assays usually have binding affinities of at least $10^{-6}$, $10^{-7}$, $10^{-8}$, $10^{-9}$, $10^{-10}$, $10^{-11}$, or $10^{-12}$ M. In certain aspects, CLDN 18.2 antibodies used as diagnostic reagents have a sufficient kinetic on-rate to reach equilibrium under standard conditions in at least 12 hours, at least 5 hours, at least 1 hour, or at least 30 minutes.

Some methods of the present technology employ polyclonal preparations of anti-CLDN 18.2 antibodies and polyclonal anti-CLDN 18.2 antibody compositions as diagnostic reagents, and other methods employ monoclonal isolates. In methods employing polyclonal human anti-CLDN 18.2 antibodies prepared in accordance with the methods described above, the preparation typically contains an assortment of CLDN 18.2 antibodies, e.g., antibodies, with different epitope specificities to the target polypeptide. The monoclonal anti-CLDN 18.2 antibodies of the present disclosure are useful for detecting a single antigen in the presence or potential presence of closely related antigens.

The CLDN 18.2 antibodies of the present disclosure can be used as diagnostic reagents for any kind of biological sample. In one aspect, the CLDN 18.2 antibodies disclosed herein are useful as diagnostic reagents for human biological samples. CLDN 18.2 antibodies can be used to detect CLDN 18.2 polypeptides in a variety of standard assay formats. Such formats include immunoprecipitation, Western blotting, ELISA, radioimmunoassay, flow cytometry, IHC and immunometric assays. See Harlow & Lane, Antibodies, A Laboratory Manual (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue (including biopsies), cell or body fluid of a subject.

Prognostic Uses of CLDN 18.2 antibodies. The present disclosure also provides for prognostic (or predictive) assays for determining whether a subject is at risk of developing a medical disease or condition associated with increased CLDN 18.2 polypeptide expression or activity (e.g., detection of a precancerous cell). Such assays can be used for prognostic or predictive purpose to thereby prophylactically treat an individual prior to the onset of a medical disease or condition characterized by or associated with CLDN 18.2 polypeptide expression.

Another aspect of the present disclosure provides methods for determining CLDN 18.2 expression in a subject to thereby select appropriate therapeutic or prophylactic compounds for that subject.

Alternatively, the prognostic assays can be utilized to identify a subject having or at risk for developing gastric, pancreatic, esophageal, ovarian, or lung cancer. Thus, the present disclosure provides a method for identifying a disease or condition associated with increased CLDN 18.2 polypeptide expression levels in which a test sample is obtained from a subject and the CLDN 18.2 polypeptide detected, wherein the presence of increased levels of CLDN 18.2 polypeptides compared to a control sample is predictive for a subject having or at risk of developing a disease or condition associated with increased CLDN 18.2 polypeptide expression levels. In some aspects, the disease or condition associated with increased CLDN 18.2 polypeptide expression levels is selected from the group consisting of gastric, pancreatic, esophageal, ovarian, and lung cancer.

In another aspect, the present disclosure provides methods for determining whether a subject can be effectively treated with a compound for a disorder or condition associated with increased CLDN 18.2 polypeptide expression wherein a biological sample is obtained from the subject and the CLDN 18.2 polypeptide is detected using the CLDN 18.2 antibody. The expression level of the CLDN 18.2 polypeptide in the biological sample obtained from the subject is determined and compared with the CLDN 18.2 expression levels found in a biological sample obtained from a subject who is free of the disease. Elevated levels of the CLDN 18.2 polypeptide in the sample obtained from the subject suspected of having the disease or condition compared with the sample obtained from the healthy subject is indicative of the CLDN 18.2-associated disease or condition in the subject being tested.

There are a number of disease states in which the elevated expression level of CLDN 18.2 polypeptides is known to be indicative of whether a subject with the disease is likely to respond to a particular type of therapy or treatment. Thus, the method of detecting a CLDN 18.2 polypeptide in a biological sample can be used as a method of prognosis, e.g., to evaluate the likelihood that the subject will respond to the therapy or treatment. The level of the CLDN 18.2 polypeptide in a suitable tissue or body fluid sample from the subject is determined and compared with a suitable control, e.g., the level in subjects with the same disease but who have responded favorably to the treatment.

In one aspect, the present disclosure provides for methods of monitoring the influence of agents (e.g., drugs, compounds, or small molecules) on the expression of CLDN 18.2 polypeptides. Such assays can be applied in basic drug screening and in clinical trials. For example, the effectiveness of an agent to decrease CLDN 18.2 polypeptide levels can be monitored in clinical trials of subjects exhibiting elevated expression of CLDN 18.2, e.g., patients diagnosed with cancer. An agent that affects the expression of CLDN 18.2 polypeptides can be identified by administering the agent and observing a response. In this way, the expression pattern of the CLDN 18.2 polypeptide can serve as a marker, indicative of the physiological response of the subject to the agent. Accordingly, this response state may be determined before, and at various points during, treatment of the subject with the agent.

Further aspects of the present disclosure relate to methods for determining if a patient is likely to respond or is not likely to CLDN 18.2 CAR therapy. In specific embodiments, this method comprises contacting a tumor sample isolated from the patient with an effective amount of an CLDN 18.2 antibody and detecting the presence of any antibody bound to the tumor sample. In further embodiments, the presence of antibody bound to the tumor sample indicates that the patient is likely to respond to the CLDN 18.2 CAR therapy and the absence of antibody bound to the tumor sample indicates that the patient is not likely to respond to the CLDN 18.2 therapy. In some embodiments, the method comprises the additional step of administering an effective amount of the CLDN 18.2 CAR therapy to a patient that is determined likely to respond to the CLDN 18.2 CAR therapy.

Automated Embodiments. A person of ordinary skill in the art will appreciate that aspects of the methods for using the CLDN 18.2 antibodies disclosed herein can be automated. Particular aspects of CLDN 18.2 staining procedures can be conducted using various automated processes.

IV. Kits

As set forth herein, the present disclosure provides diagnostic methods for determining the expression level of CLDN 18.2. In one particular aspect, the present disclosure provides kits for performing these methods as well as instructions for carrying out the methods of the present disclosure such as collecting tissue and/or performing the screen, and/or analyzing the results.

The kit comprises, or alternatively consists essentially of, or yet further consists of, a CLDN 18.2 antibody composition (e.g., monoclonal antibodies) disclosed herein, and instructions for use. The kits are useful for detecting the presence of CLDN 18.2 polypeptides in a biological sample e.g., any body fluid including, but not limited to, e.g., sputum, serum, plasma, lymph, cystic fluid, urine, stool, cerebrospinal fluid, acetic fluid or blood and including biopsy samples of body tissue. The test samples may also be a tumor cell, a normal cell adjacent to a tumor, a normal cell corresponding to the tumor tissue type, a blood cell, a peripheral blood lymphocyte, or combinations thereof. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

In some aspects, the kit can comprise: one or more CLDN 18.2 antibodies capable of binding a CLDN 18.2 polypeptide in a biological sample (e.g., an antibody or antigen-binding fragment thereof having the same antigen-binding specificity of CLDN 18.2 antibody B7H4 5F6, B7H4 #33-14, or B7H4 #36-1); means for determining the amount of the CLDN 18.2 polypeptide in the sample; and means for comparing the amount of the CLDN 18.2 polypeptide in the sample with a standard. One or more of the CLDN 18.2 antibodies may be labeled. The kit components, (e.g., reagents) can be packaged in a suitable container. The kit can further comprise instructions for using the kit to detect the CLDN 18.2 polypeptides. In certain aspects, the kit comprises a first antibody, e.g., attached to a solid support, which binds to a CLDN 18.2 polypeptide; and, optionally; 2) a second, different antibody which binds to either the CLDN 18.2 polypeptide or the first antibody and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present disclosure may contain a written product on or in the kit container. The written product describes how to use the reagents contained in the kit.

As amenable, these suggested kit components may be packaged in a manner customary for use by those of skill in the art. For example, these suggested kit components may be provided in solution or as a liquid dispersion or the like.

V. Carriers

The antibodies or CLDN 18.2 CARs also can be bound to many different carriers. Thus, this disclosure also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding antibodies, or will be able to ascertain such, using routine experimentation.

Chimeric Antigen Receptors and Uses Thereof

I. Compositions

The present disclosure provides chimeric antigen receptors (CAR) that bind to CLDN 18.2 comprising, or consisting essentially of, an extracellular and intracellular domain. The extracellular domain comprises a target-specific binding element otherwise referred to as the antigen binding domain. The intracellular domain or cytoplasmic domain comprises a costimulatory signaling region and a zeta chain portion. The CAR may optionally further comprise a spacer domain of up to 300 amino acids, preferably 10 to 100 amino acids, more preferably 25 to 50 amino acids.

Antigen Binding Domain. In certain aspects, the present disclosure provides a CAR that comprises, or alternatively consists essentially thereof, or yet consists of an antigen binding domain specific to CLDN 18.2. In some embodiments, the antigen binding domain comprises, or alternatively consists essentially thereof, or yet consists of the antigen binding domain of an anti-CLDN 18.2 antibody. In further embodiments, the heavy chain variable region and light chain variable region of an anti-CLDN 18.2 antibody comprises, or alternatively consists essentially thereof, or yet consists of the antigen binding domain the anti-CLDN 18.2 antibody. These antibodies and their sequences are disclosed herein. As is apparent to the skilled artisan, the antibody fragments against CLDN 18.2 as disclosed herein can be used to generate a CAR. Thus, the relevant disclosure is incorporated herein.

Transmembrane Domain. The transmembrane domain may be derived either from a natural or from a synthetic source. Where the source is natural, the domain may be derived from any membrane-bound or transmembrane protein. Transmembrane regions of particular use in this invention may be derived from CD8, CD28, CD3, CD45, CD4, CD5, CDS, CD9, CD16, CD22, CD33, CD37, CD64, CD80, CD86, CD134, CD137, CD154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Cytoplasmic Domain. The cytoplasmic domain or intracellular signaling domain of the CAR is responsible for activation of at least one of the traditional effector functions of an immune cell in which a CAR has been placed. The intracellular signaling domain refers to a portion of a protein which transduces the effector function signal and directs the immune cell to perform its specific function. An entire signaling domain or a truncated portion thereof may be used so long as the truncated portion is sufficient to transduce the effector function signal. Cytoplasmic sequences of the TCR and co-receptors as well as derivatives or variants thereof can function as intracellular signaling domains for use in a CAR. Intracellular signaling domains of particular use in this invention may be derived from FcR, TCR, CD3, CDS, CD22, CD79a, CD79b, CD66d. Since signals generated through the TCR are alone insufficient for full activation of a T cell, a secondary or co-stimulatory signal may also be required. Thus, the intracellular region of a co-stimulatory signaling molecule, including but not limited CD27, CD28, 4-IBB (CD137), OX40, CD30, CD40, PD-1, ICOS, lymphocyte function-associated antigen-1 (LFA-1), CD2, CD7, LIGHT, NKG2C, B7-H3, or a ligand that specifically binds with CD83, to may also be included in the cytoplasmic domain of the CAR.

In some embodiments, the cell activation moiety of the chimeric antigen receptor is a T-cell signaling domain comprising, or alternatively consisting essentially of, or yet further consisting of, one or more proteins or fragments thereof selected from the group consisting of CD8 protein, CD28 protein, 4-1BB protein, and CD3-zeta protein.

In specific embodiments, the CAR comprises, or alternatively consists essentially thereof, or yet consists of an antigen binding domain of an anti-CLDN 18.2 antibody, a CD8α hinge domain, a CD8α transmembrane domain, a costimulatory signaling region, and a CD3 zeta signaling domain. In further embodiments, the costimulatory signaling region comprises either or both a CD28 costimulatory signaling region and a 4-1BB costimulatory signaling region.

In some embodiments, the CAR can further comprise a detectable marker or purification marker.

II. Process for Preparing CARs

Aspects of the present disclosure relate to an isolated cell comprising a CAR and methods of producing such cells. The cell is a prokaryotic or a eukaryotic cell. In one aspect, the cell is a T-cell, a B cell, a NK cell, a dendritic cell, a myeloid cell, a monocyte, a macrophage, any subsets thereof, or any other immune cell. The eukaryotic cell can be from any preferred species, e.g., an animal cell, a mammalian cell such as a human, a feline or a canine cell. The cells may be derived from patients, donors, or cell lines, such as those available off-the-shelf.

In specific embodiments, the isolated cell comprises, or alternatively consists essentially of, or yet further consists of an exogenous CAR comprising, or alternatively consisting essentially of, or yet further consisting of, an antigen binding domain of a anti-CLDN 18.2 antibody, a CD8α hinge domain, a CD8α transmembrane domain, a CD28 costimulatory signaling region and/or a 4-1BB costimulatory signaling region, and a CD3 zeta signaling domain. In certain embodiments, the isolated cell is a T-cell, e.g., an animal T-cell, a mammalian T-cell, a feline T-cell, a canine T-cell or a human T-cell. In certain embodiments, the isolated cell is an NK-cell, e.g., an animal NK-cell, a mammalian NK-cell, a feline NK-cell, a canine NK-cell or a human NK-cell. In certain embodiments, the isolated cell is a B-cell, e.g., an animal B-cell, a mammalian B-cell, a feline B-cell, a canine B-cell or a human B-cell. It is appreciated that the same or similar embodiments for each species apply with respect to dendritic cells, myeloid cells, monocytes, macrophages, any subsets of these or the T-cells, NK-cells, and B-cells described, and/or any other immune cells.

In certain embodiments, methods of producing CAR expressing cells are disclosed the method comprising, or alternatively consisting essentially of or yet further consisting of transducing a population of isolated cells with a nucleic acid sequence encoding a CAR. In a further aspect, a subpopulation of cells that have been successfully transduced with said nucleic acid sequence is selected. In some embodiments, the isolated cells are T-cells, an animal T-cell, a mammalian T-cell, a feline T-cell, a canine T-cell or a human T-cell, thereby producing CAR T-cells. In certain embodiments, the isolated cell is an NK-cell, e.g., an animal NK-cell, a mammalian NK-cell, a feline NK-cell, a canine NK-cell or a human NK-cell, thereby producing CAR NK-cells. In some embodiments, the isolated cells are B-cells, an animal B-cell, a mammalian B-cell, a feline B-cell, a canine B-cell or a human B-cell, thereby producing CAR B-cells. It is appreciated that the same or similar embodiments for each species apply with respect to dendritic cells, myeloid cells, monocytes, macrophages, any subsets of these or the T-cells, NK-cells, and B-cells described, and/or any other immune cells.

Sources of Isolated Cells. Prior to expansion and genetic modification of the cells disclosed herein, cells may be obtained from a subject—for instance, in embodiments involving autologous therapy—or a commercially available culture.

Cells can be obtained from a number of sources in a subject, including peripheral blood mononuclear cells, bone marrow, lymph node tissue, cord blood, thymus tissue, tissue from a site of infection, ascites, pleural effusion, spleen tissue, and tumors.

Methods of isolating relevant cells are well known in the art and can be readily adapted to the present application; an exemplary method is described in the examples below. Isolation methods for use in relation to this disclosure include, but are not limited to Life Technologies Dynabeads® system; STEMcell Technologies EasySep™, RoboSep™ RosetteSep™, SepMate™; Miltenyi Biotec MACS™ cell separation kits, and other commercially available cell separation and isolation kits. Particular subpopulations of immune cells may be isolated through the use of beads or other binding agents available in such kits specific to unique cell surface markers. For example, MACS™ CD4+ and CD8+MicroBeads may be used to isolate CD4+ and CD8+T-cells. Alternate non-limiting examples of cells that may be isolated according to known techniques include bulked T-cells, NK T-cells, and gamma delta T-cells.

Alternatively, cells may be obtained through commercially available cell cultures, including but not limited to, for T-cells, lines BCL2 (AAA) Jurkat (ATCC® CRL-2902™) BCL2 (S70A) Jurkat (ATCC® CRL-2900™), BCL2 (S87A) Jurkat (ATCC® CRL-2901™) BCL2 Jurkat (ATCC® CRL-2899™), Neo Jurkat (ATCC® CRL-2898™); for B cells, lines AHH-1 (ATCC® CRL-8146™), BC-1 (ATCC® CRL-2230™), BC-2 (ATCC® CRL-2231™) BC-3 (ATCC® CRL-2277™), CA46 (ATCC® CRL-1648™), DG-75[DG-75] (ATCC® CRL-2625™), DS-1 (ATCC® CRL-11102™), EB-3[EB3] (ATCC® CCL-85™), Z-138 (ATCC #CRL-3001), DB (ATCC CRL-2289), Toledo (ATCC CRL-2631), Pfiffer (ATCC CRL-2632), SR (ATCC CRL-2262), JM-1 (ATCC CRL-10421), NFS-5 C-1 (ATCC CRL-1693); NFS-70 C10 (ATCC CRL-1694), NFS-25 C-3 (ATCC CRL-1695), and SUP-B15 (ATCC CRL-1929); and, for NK cells, lines NK-92 (ATCC® CRL-2407™), NK-92MI (ATCC® CRL-2408™) Further examples include but are not limited to mature T-cell lines, e.g., Deglis, EBT-8, HPB-MLp-W, HUT 78, HUT 102, Karpas 384, Ki 225, My-La, Se-Ax, SKW-3, SMZ-1 and T34; immature T-cell lines, e.g., ALL-SIL, Be13, CCRF-CEM, CML-T1, DND-41, DU.528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4;11 (ATCC CRL-1873), CCRF-CEM (ATCC CRM-CCL-119); cutaneous T-cell lymphoma lines, e.g., HuT78 (ATCC CRM-TIB-161), MJ[G11] (ATCC CRL-8294), HuT102 (ATCC TIB-162); B-cell lines derived from anaplastic and large cell lymphomas, e.g., DEL, DL-40, FE-PD, JB6, Karpas 299, Ki-JK, Mac-2A Ply1, SR-786, SU-DHL-1, -2, -4, -5, -6, -7, -8, -9, -10, and -16, DOHH-2, NU-DHL-1, U-937, Granda 519, USC-DHL-1, RL; Hodgkin's lymphomas, e.g., DEV, HD-70, HDLM-2, HD-MyZ, HKB-1, KM-H2, L428, L540, L1236, SBH-1, SUP-HD1, and SU/RH-HD-1; and NK lines such as HANK1, KHYG-1, NKL, NK-YS, NOI-90, and YT. Null leukemia cell lines, including but not limited to REH, NALL-1, KM-3, L92-221, are a another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (www.atcc.org/) and the German Collection of Microorganisms and Cell Cultures (www.dsmz.de/).

In some embodiments, T-cells expressing the disclosed CARs may be further modified to reduce or eliminate expression of endogenous TCRs. Reduction or elimination of endogenous TCRs can reduce off-target effects and increase the effectiveness of the T cells. T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs.

The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

Even though some TCR complexes can be recycled to the cell surface when RNA interference is used, the RNA (e.g., shRNA, siRNA, miRNA, etc.) will prevent new production of TCR proteins resulting in degradation and removal of the entire TCR complex, resulting in the production of a T cell having a stable deficiency in functional TCR expression.

Expression of inhibitory RNAs (e.g., shRNA, siRNA, miRNA, etc.) in primary T cells can be achieved using any conventional expression system, e.g., a lentiviral expression system. Although lentiviruses are useful for targeting resting primary T cells, not all T cells will express the shRNAs. Some of these T cells may not express sufficient amounts of the RNAs to allow enough inhibition of TCR expression to alter the functional activity of the T cell. Thus, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3.

Expression of CRISPR in primary T cells can be achieved using conventional CRISPR/Cas systems and guide RNAs specific to the target TCRs. Suitable expression systems, e.g. lentiviral or adenoviral expression systems are known in the art. Similar to the delivery of inhibitor RNAs, the CRISPR system can be use to specifically target resting primary T cells or other suitable immune cells for CAR cell therapy. Further, to the extent that CRISPR editing is unsuccessful, cells can be selected for success according to the methods disclosed above. For example, as noted above, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3. It is further appreciated that a CRISPR editing construct may be useful in both knocking out the endogenous TCR and knocking in the CAR constructs disclosed herein. Accordingly, it is appreciated that a CRISPR system can be designed for to accomplish one or both of these purposes.

Vectors. CAR cells may be prepared using vectors. Aspects of the present disclosure relate to an isolated nucleic acid sequence encoding (i) a CAR or (ii) a polynucleotide encoding an immunoregulatory molecule and vectors comprising, or alternatively consisting essentially of, or yet further consisting of, an either one or both of these nucleic acids and/or complements and/or equivalents of each thereof.

In some embodiments, the isolated nucleic acid sequence encodes for a CAR comprising, or alternatively consisting essentially of, or yet further consisting of an antigen binding domain of a cancer or tumor targeting antibody, a CD8α hinge domain, a CD8α transmembrane domain, a CD28 costimulatory signaling region and/or a 4-1BB costimulatory signaling region, and a CD3 zeta signaling domain. In specific embodiments, the isolated nucleic acid sequence comprises, or alternatively consisting essentially thereof, or yet further consisting of, sequences encoding (a) an antigen binding domain of an anti-CLDN 18.2 antibody followed by (b) a CD8α hinge domain, (c) a CD8α transmembrane domain followed by (d) a CD28 costimulatory signaling region and/or a 4-1BB costimulatory signaling region followed by (e) a CD3 zeta signaling domain.

In some embodiments, the isolated nucleic acid sequence encodes for a CAR and comprises, or alternatively consists essentially of, or yet further consists of, a Kozak consensus sequence upstream of the sequence encoding the antigen binding domain of the anti-CLDN 18.2 antibody.

In some embodiments, the isolated nucleic acid comprises a detectable label and/or a polynucleotide conferring antibiotic resistance. In one aspect, the label or polynucleotide are useful to select cells successfully transduced with the isolated nucleic acids.

In some embodiments, the isolated nucleic acid sequence is comprised within a vector. In certain embodiments, the vector is a plasmid. In other embodiments, the vector is a viral vector. Non-limiting examples of such include without limitation a retroviral vector, a lentiviral vector, an adenoviral vector, and an adeno-associated viral vector. In specific embodiments, the vector is a lentiviral vector.

The preparation of exemplary vectors and the generation of CAR expressing cells using said vectors is discussed in detail in the examples below. In summary, the expression of natural or synthetic nucleic acids encoding CARs or immunoregulatory molecules is typically achieved by operably linking a nucleic acid encoding the CAR polypeptide or portions thereof to a promoter, and incorporating the construct into an expression vector. A similar method may be used to construct the isolated nucleic acid sequence comprising a polynucleotide encoding an immunoregulatory molecule. The vectors can be suitable for replication and integration eukaryotes. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

In one aspect, the term "vector" intends a recombinant vector that retains the ability to infect and transduce non-dividing and/or slowly-dividing cells and integrate into the target cell's genome. In several aspects, the vector is derived from or based on a wild-type virus. In further aspects, the vector is derived from or based on a wild-type lentivirus. Examples of such include without limitation, human immunodeficiency virus (HIV), equine infectious anemia virus (EIAV), simian immunodeficiency virus (SIV) and feline immunodeficiency virus (FIV). Alternatively, it is contemplated that other retrovirus can be used as a basis for a vector backbone such murine leukemia virus (MLV). It will be evident that a viral vector according to the disclosure need not be confined to the components of a particular virus. The viral vector may comprise components derived from two or more different viruses, and may also comprise synthetic components. Vector components can be manipulated to obtain desired characteristics such as target cell specificity.

The recombinant vectors of this disclosure are derived from primates and non-primates. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,419,829 and 7,442,551, incorporated herein by reference.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5' end of the RNA. The sizes of the three elements can vary considerably among different retroviruses. For the viral genome- and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways.

The techniques involved are known to those skilled in the art.

Retroviral vectors for use in this disclosure include, but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charité Medical School, Institute of Virology (CBF), Berlin, Germany.

Further methods of introducing exogenous nucleic acids into the art are known and include but are not limited to gene delivery using one or more of RNA electroporation, nanotechnology, sleeping beauty vectors, retroviruses, and/or adenoviruses.

Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELiSAs and Western blots) or by assays described herein to identify agents falling within the scope of the disclosure.

Packaging vector and cell lines. The isolated nucleic acids can be packaged into a retroviral packaging system by using a packaging vector and cell lines. The packaging vector includes, but is not limited to retroviral vector, lentiviral vector, adenoviral vector, and adeno-associated viral vector. The packaging vector contains elements and sequences that facilitate the delivery of genetic materials into cells. For example, the retroviral constructs are packaging vectors comprising at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus. The retroviral DNA sequence lacks the region encoding the native enhancer and/or promoter of the viral 5' LTR of the virus, and lacks both the psi function sequence responsible for packaging helper genome and the 3' LTR, but encodes a foreign polyadenylation site, for example the SV40 polyadenylation site, and a foreign enhancer and/or promoter which directs efficient transcription in a cell type where virus production is desired. The retrovirus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter. The retroviral packaging vector may consist of two retroviral helper DNA sequences encoded by plasmid based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell.

In the packaging process, the packaging vectors and retroviral vectors are transiently cotransfected into a first population of mammalian cells that are capable of producing virus, such as human embryonic kidney cells, for example 293 cells (ATCC No. CRL1573, ATCC, Rockville, Md.) to produce high titer recombinant retrovirus-containing supernatants. In another method of the disclosure this transiently transfected first population of cells is then cocultivated with mammalian target cells, for example human lymphocytes, to transduce the target cells with the foreign gene at high efficiencies. In yet another method of the invention the supernatants from the above described transiently transfected first population of cells are incubated with mammalian target cells, for example human lymphocytes or hematopoietic stem cells, to transduce the target cells with the foreign gene at high efficiencies.

In another aspect, the packaging vectors are stably expressed in a first population of mammalian cells that are capable of producing virus, such as human embryonic kidney cells, for example 293 cells. Retroviral or lentiviral vectors are introduced into cells by either cotransfection with a selectable marker or infection with pseudotyped virus. In both cases, the vectors integrate. Alternatively, vectors can be introduced in an episomally maintained plasmid. High titer recombinant retrovirus-containing supernatants are produced.

Activation and Expansion of CAR Cells. Whether prior to or after genetic modification of the cells to express a desirable CAR, the cells can be activated and expanded using generally known methods such as those described in U.S. Pat. Nos. 6,352,694; 6,534,055; 6,905,680; 6,692,964; 5,858,358; 6,887,466; 6,905,681; 7, 144,575; 7,067,318; 7, 172,869; 7,232,566; 7, 175,843; 5,883,223; 6,905,874; 6,797,514; 6,867,041 and references such as Lapateva et al. (2014) Crit Rev Oncog 19(1-2):121-32; Tam et al. (2003) Cytotherapy 5(3):259-72; Garcia-Marquez et al. (2014) Cytotherapy 16(11):1537-44. Stimulation with the CLDN 18.2 antigen ex vivo can activate and expand the selected CAR expressing cell subpopulation. Alternatively, the cells may be activated in vivo by interaction with CLDN 18.2 antigen.

In the case of certain immune cells, additional cell populations, soluble ligands and/or cytokines, or stimulating agents may be required to activate and expand cells. The relevant reagents are well known in the art and are selected according to known immunological principles. For instance, soluble CD-40 ligand may be helpful in activating and expanding certain B-cell populations; similarly, irradiated feeder cells may be used in the procedure for activation and expansion of NK cells.

Methods of activating relevant cells are well known in the art and can be readily adapted to the present application; an exemplary method is described in the examples below. Isolation methods for use in relation to this disclosure include, but are not limited to Life Technologies Dynabeads® system activation and expansion kits; BD Biosciences Phosflow™ activation kits, Miltenyi Biotec MACS™ activation/expansion kits, and other commercially available cell kits specific to activation moieties of the relevant cell. Particular subpopulations of immune cells may be activated or expanded through the use of beads or other agents available in such kits. For example, α-CD3/α-CD28 Dynabeads® may be used to activate and expand a population of isolated T-cells.

As disclosed above, chimeric antigen receptors comprise an antigen recognition moiety and a cell activation moiety. Aspects of the present disclosure related to a chimeric antigen receptor (CAR) comprising an antigen binding domain specific to CLDN 18.2.

In one embodiment, the CAR of the present disclosure is characterized in that it comprises, or alternatively consists essentially of, or yet further consists an antigen binding domain of an anti-luteinizing hormone receptor ("CLDN 18.2") antibody, a CD8α hinge domain; a CD8α transmembrane domain; a CD28 and/or a 4-1BB costimulatory signaling region; and a CD3 zeta signaling domain.

In another embodiment, the antigen binding domain of the anti-CLDN 18.2 antibody comprises an anti-CLDN 18.2 heavy chain variable region and an anti-CLDN 18.2 light chain variable region. As apparent to the skilled artisan, antibodies having the detailed elements are also within the scope of this disclosure.

In some embodiments, the isolated nucleic acid further comprises, or alternatively consists essentially of, or yet further consists of a Kozak consensus sequence located upstream of the antigen binding domain of the anti-CLDN 18.2 antibody.

In some aspect of the disclosure, the isolated nucleic sequence further comprises, or alternatively consists essentially of, or yet further consists of polynucleotide encoding an antibiotic resistance marker.

In another embodiment, the disclosure provides a vector comprising, or alternatively consisting essentially of, or yet further consisting of the isolated nucleic acid sequence encoding the anti-CLDN 18.2 CAR polypeptide as disclosed above or a complement thereof. In a further aspect, the polynucleotide can be incorporated into a vector. Non-limiting examples of such include a retroviral vector, a plasmid, a lentiviral vector, an adenoviral vector, and an adeno-associated viral vector.

In one embodiment, the disclosure is an isolated cell comprising, or alternatively consisting essentially of, or yet further consisting of an exogenously added polynucleotide encoding the anti-CLDN 18.2 CAR as described above alone or in combination with a vector as described above; and/or the exogenously added the anti-CLDN 18.2 CAR; as describe above.

In one aspect of the disclosure, the isolated cell can be a T-cell or a natural killer (NK) cell.

III. Methods of Use

Therapeutic Application. The CAR T-cells of the present invention may be used to treat tumors and cancers. The CAR-T cells of the present invention may be administered either alone or in combination with diluents, known anticancer therapeutics, and/or with other components such as cytokines or other cell populations that are immunostimulatory.

Method aspects of the present disclosure relate to methods for inhibiting the growth of a tumor in a subject in need thereof and/or for treating a cancer patient in need thereof. In some embodiments, the tumor is a solid tumor. In some embodiments, the tumors/cancer is gastric, pancreatic, esophageal, ovarian, or lung tumors/cancer. In some embodiments, the tumor or cancer expresses or overexpresses CLDN 18.2. In certain embodiments, these methods comprise, or alternatively consist essentially of, or yet further consist of, administering to the subject or patient an effective amount of the isolated cell. In further embodiments, this isolated cell comprises a CLDN 18.2 CAR. In still further embodiments, the isolated cell is a T-cell or an NK cell. In some embodiments, the isolated cell is autologous to the subject or patient being treated. In a further aspect, the tumor expresses CLDN 18.2 antigen and the subject has been selected for the therapy by a diagnostic, such as the one described herein.

The CAR cells as disclosed herein may be administered either alone or in combination with diluents, known anticancer therapeutics, and/or with other components such as cytokines or other cell populations that are immunostimulatory. They may be first line, second line, third line, fourth line, or further therapy. The can be combined with other therapies. Non-limiting examples of such include chemotherapies or biologics. Appropriate treatment regimes will be determined by the treating physician or veterinarian.

Pharmaceutical compositions comprising the CLDN 18.2 CAR of the present invention may be administered in a manner appropriate to the disease to be treated or prevented. The quantity and frequency of administration will be determined by such factors as the condition of the patient, and the type and severity of the patient's disease, although appropriate dosages may be determined by clinical trials.

In another aspect, the disclosure provides a method of inhibiting the growth of a solid tumor in a subject in need thereof, comprising administering to the subject an effective amount of the isolated cell of anti-CLDN 18.2 CAR T-cell or NK-cell. In one embodiment, the isolated T-cells or NK-cells are autologous to the subject being treated. In another embodiment, the tumor is a gastric, colon, colorectal, pancreatic, esophageal, ovarian, or lung tumor. The method of inhibiting the growth of a tumor can be applied to a subject including but not limited to human, dog, cat, horse, and other species.

In another aspect, the disclosure provides a method of treating a cancer patient in need thereof, comprising, or alternatively consisting essentially of, or yet further consisting of administering to the subject an effective amount of the isolated cell of anti-CLDN 18.2 T-cell or NK-cell. The isolated T-cells or NK-cells can be autologous to the subject being treated. The tumor is gastric, pancreatic, esophageal, ovarian, or lung cancer. In one embodiment, the subject treated for cancer is a human patient.

In one embodiment, the disclosure provides a method for determining if a patient is likely to respond or is not likely to anti-CLDN 18.2 CAR therapy, comprising, or alternatively consisting essentially of, or yet further consisting of contacting a tumor sample isolated from the patient with an effective amount of an anti-CLDN 18.2 antibody and detecting the presence of any antibody bound to the tumor sample, wherein the presence of antibody bound to the tumor sample indicates that the patient is likely to respond to the anti-CLDN 18.2 CAR therapy and the absence of antibody bound to the tumor sample indicates that the patient is not likely to respond to the anti-CAR therapy. In another embodiment, the method further comprises administering an effective amount of the anti-CLDN 18.2 CAR therapy to the patient that is determined likely to respond to the anti-CLDN 18.2 CAR therapy. In this method, the patient can suffer from gastric, pancreatic, esophageal, ovarian, or lung cancer.

The present disclosure also provides diagnostic methods for determining the expression level of CLDN 18.2. In one particular aspect, the present disclosure provides kits for performing these methods as well as instructions for carrying out the methods of the present disclosure such as collecting tissue and/or performing the screen, and/or analyzing the results.

In one embodiment, the disclosure provides a method of detecting CLDN 18.2 in a biological sample comprising, or alternatively consisting essentially of, or yet further consisting of contacting the sample with an anti-CLDN 18.2 antibody or an antigen binding fragment capable of binding a peptide comprising SEQ ID NOs: 42 and 43, and detecting a complex formed by the binding of the antibody or antigen binding fragment to CLDN 18.2.

In one aspect, the sample comprises a cell sample or a tissue sample.

In one aspect, the sample is obtained from a subject that is diagnosed as having, suspected as having, or at risk of having cancer.

In another aspect, the cancer is gastric, pancreatic, esophageal, ovarian, or lung cancer. In a further aspect, the cancer cell or tumor cell expresses or overexpresses CLDN 18.2.

In one aspect, the detection comprises, or alternatively consists essentially of, or yet further consists of one or more of immunohistochemistry (IHC), Western blotting, Flow cytometry or ELISA.

In one aspect, the method comprises, or alternatively consists essentially of, or yet further consists of isolating the biological sample from the subject.

In one aspect, the subject is a mammal.

In another aspect, the mammal is selected from the group of: a human, an animal, a non-human primate, a dog, cat, a sheep, a mouse, a horse, or a cow.

In one embodiment, the disclosure provides a method of detecting a pathological cell in a sample isolated from a subject, comprising, or alternatively consisting essentially of, or yet further consisting of (a) detecting the level of CLDN 18.2 in a biological sample from the subject by detecting a complex formed by an anti-CLDN 18.2 antibody or an antigen binding fragment capable of binding a peptide comprising CLDN 18.2 and (b) comparing the levels of CLDN 18.2 observed in step (a) with the levels of CLDN 18.2 observed in a control biological sample; wherein the pathological cell is detected when the level of CLDN 18.2 is elevated compared to that observed in the control biological sample.

In one aspect, the biological sample of the subject comprises, or alternatively consists essentially of, or yet further consists of one or more of a sample isolated from gastric, pancreatic, esophageal, ovarian, or lung tissue.

In another aspect, the detection comprises, or alternatively consists essentially of, or yet further consists of one or more of immunohistochemistry (IHC), Western Blotting, Flow cytometry or ELISA.

In one aspect, the method comprises, or alternatively consists essentially of, or yet further consists of isolating the biological sample from the subject.

In one aspect, the subject is a mammal.

In another aspect, the mammal is selected from the group of: a human, an animal, a non-human primate, a dog, cat, a sheep, a mouse, a horse, or a cow.

IV. Carriers

Additional aspects of the invention relate to compositions comprising a carrier and one or more of the products—e.g., an isolated cell comprising a CLDN 18.2 CAR, an isolated nucleic acid, a vector, an isolated cell of any anti-CLDN 18.2 antibody or CAR cell, an anti-CLDN 18.2—described in the embodiments disclosed herein.

Briefly, pharmaceutical compositions of the present invention including but not limited to any one of the claimed compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

Briefly, pharmaceutical compositions of the present invention including but not limited to any one of the claimed compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated or prevented. The quantity and frequency of administration will be determined by such factors as the condition of the patient, and the type and severity of the patient's disease, although appropriate dosages may be determined by clinical trials.

The following examples are provided to illustrate, and not limit the disclosure.

EXAMPLES

Example 1: Generation of Mouse Monoclonal Antibodies Against Human CLDN 18.2

Anti-human CLDN 18.2 mouse monoclonal antibodies were generated using the hybridoma technology.

Antigens: a) cDNA encoding human CLDN 18.2EC1 (extra-cellular domain 1) human Fc protein; b) human CLDN 18.2EC1 (extra-cellular domain 1) human Fc protein; c) CHO cells expressing full length human CLDN 18.2.

Immunization: To generate mouse monoclonal antibodies to human CLDN 18.2, 4-6 week female Swiss Webster mice were first immunized with cDNAs encoding human CLDN 18.2EC1 human Fc protein at 40ug/mouse. Day 21 and 35 post first immunization, the immunized mice were boosted with 30 ugs of human CLDN 18.2EC1 human Fc protein each mouse. The immunized mice were further boosted with CHO cells expressing full length human CLDN 18.2. To select mice producing antibodies that bound to human CLDN 18.2, sera from immunized mice were tested by ELISA and FACS analysis.

For ELISA assays, microtiter plates were coated with human CLDN 18.2 EC1 human Fc protein at 1 µg/ml in PBS, 100 µl/well at 4° C. overnight and blocked with 100 µl/well of 2% BSA for 1 hour at RT. Dilutions of serum from immunized mice were added to each well and incubated for 1-2 hours at RT. The plates were washed with PBS/Tween and then incubate with anti-mouse IgG antibody conjugated with Horse Radish Peroxidase (HRP) for 1 hour at RT. After washing, the plates were developed with TMB peroxidase substrate and analyzed by spectrophotometer at OD 450 nm.

For FACS based titer analysis, 96 well microtiter plates were seeded with human CLDN 18.2/CHO cells or CLDN 18.1/CHO cells at 200,000 cells/well. Dilutions of serum from immunized mice were added to each well. The cells were mixed well and incubated at 4° C. for 15 min. The cells were then washed with PBS three times, followed by incubation with PE-labeled anti-mouse Fc gamma specific antibody (Jackson Immuno-Research) at 4° C. for 15 min. The cells were washed again with PBS three times and analyzed using an FACS Caliber instrument (Becton-Dickinson). Mice with sufficient specific titers to CLDN 18.2 were boosted with 30ug human CLDN 18.2EC1 huFc protein 3-4 days before fusions.

Hybridoma fusions were done using BTX2001 electrocell manipulator (Harvard Apparatus) and the standard protocol for hybridoma electro-fusion. Total mouse lymphocytes isolated from both lymph nodes and the spleens were fused with SP2/0 cells (ATCC) and hybridoma were selected using media containing Azaserine (Sigma). Hybridoma supernatants were screened using both the ELISA and FACS assays. Positive wells were further subcloned using the limited dilution method.

Hybridoma clones T13S2, T88S1, T138S2, T155S2, T158S2, T192S2, T224S8, T252S4 and LN27S4 were selected for hybridoma sequencing. Briefly, RNAs were extracted from hybridoma cells using Trizol reagents (Invitrogen) and cDNAs were prepared using the PrimeScript™ Reverse Transcriptase). Antibody heavy and light chain V regions were PCR amplified using the cDNAs and the mouse Ig-Primer Set (Novagen, TB326 Rev.B 0503) and sequences were obtained using the standard DNA sequencing techniques.

The amino acid and polynucleotide sequences of the variable regions of the antibodies are provided in Table 1 and Table 2 below.

TABLE 1

CDR combinations for anti-CLDN18.2 antibodies

| Clone Name | Comb # | CDRL combinations | | | CDRH combinations | | |
|---|---|---|---|---|---|---|---|
| | | CDRL1 | CDRL2 | CDRL3 | CDRH1 | CDRH2 | CDRH3 |
| T155S2 | 1 | QNLLNSSNQKNY | FAS | QQHYSTPLT | GFTFSSYA | ISGGGST | GGNIYDGYPYYFDY |
| | SEQ ID NO: | 1 | 2 | 3 | 4 | 5 | 6 |
| T158S2 | 2 | ESVDNYGFSF | RAS | QQSNOGPLT | GFTFSDYY | ISDGGGDT | ARHRGSLDY |
| | SEQ ID NO: | 7 | 8 | 9 | 10 | 11 | 12 |
| T224S8 | 3 | QSLVHSNGNTY | KVS | SQNTHVPRT | GFNIKDYF | IDPENGDT | NVLGYGNYGHFYYAMDY |
| | SEQ ID NO: | 13 | 14 | 15 | 16 | 17 | 18 |
| T192S2 | 4 | ESVDNYGFSF | RAS | QQSNKVPLT | GFTFSDYY | ISNGGGST | ARHRGSLDE |
| | SEQ ID NO: | 19 | 20 | 21 | 22 | 23 | 24 |
| T252S4 | 5 | ONLINSGNOKNY | WAS | QNDYIYPLP | GYSFTGYN | INPYNGGT | ARMGLGNAMDY |
| | SEQ ID NO: | 25 | 26 | 27 | 28 | 29 | 30 |
| T88S1 | 6 | ESVDNYGFSF | RAS | QQSNOGPLT | GFSLTSYG | IWSDGRT | ARHGRYDPYAMDY |
| | SEQ ID NO: | 31 | 32 | 33 | 34 | 35 | 36 |

TABLE 2

Anti-CLDN18.2 mAb heavy and light chain variable region sequences. Antibody CDRs are underlined.

| Name | Sequence | SEQ ID NO: |
|---|---|---|
| T155S2 VH | GAAGTGAAGCTGGTGGAGTCTGGGGGAGGCTTAGTGAAGCCTGGAGGGTCCC TGAAACTCTCCTGTGCAGCCTCTGGATTCACTTTCAGTAGCTATGCCATGTC TTGGGTTCGCCAGACTCCAGAGAAGAGGCTGGAGTGGGTCGCATCCATTAGT GGTGGTGGTAGCACCTACTATCCAGACAGTGTGAAGGGCCGATTCACCATCT CCAGAGATAATGCCAGGAACATCCTGTACCTGCAAATGAGCTATCTGAGGTC TGAGGACACGGCCGTGTATTACTGTGCAAGAGGAGGGAATATCTATGATGGT TACCCGTACTACTTTGACTACTGGGGCCAAGGCACCACTCTCACAGTCTCCT CA | 37 |
| T155S2 VH | EVKLVESGGGLVKPGGSLKLSCAASGFTFSSYAMSWVRQTPEKRLEWVASIS GGGSTYYPDSVKGRFTISRDNARNILYLQMSYLRSEDTAVYYCARGGNIYDG YPYYFDYWGQGTTLTVSS | 38 |
| T155S2 VL | GACATTGTGATGACCCAGTCTCCATCCTCCCTGGCTATGTCAGTAGGACAGA AGGTCACTATGAGCTGCAAGTCCAGTCAGAACCTTTTAAATAGTAGCAATCA AAAGAACTATTTGGCCTGGTACCAGCAGAAACCAGGACAGTCTCCTAAACTT CTGGTATACTTTGCATCCACTAGGGAATCTGGGGTCCCTGATCGCTTCACAG GCAGTGGATCTGGGACAGATTTCACTCTTACCATCAGCAGTGTGCAGGCTGA AGACCTGGCAGTTTATTACTGTCAGCAACATTATAGCACTCCGCTCACGTTC GGTGCTGGGACCAAGCTGGAGCTGAAA | 39 |
| T155S2 VL | DIVMTQSPSSLAMSVGQKVTMSCKSSQNLLNSSNQKNYLAWYQQKPGQSPKL LVYFASTRESGVPDRFTGSGSGTDFTLTISSVQAEDLAVYYCQQHYSTPLTF GAGTKLELK | 40 |
| T158S2 VH | GAAGTGAAGCTGGTGGAGTCTGGGGGAGGCTTAGTGCAGCCTGGAGGGTCCC TGAAACTCTCCTGTGCAACCTCTGGATTCACTTTCAGTGACTATTACATGTT TTGGATTCGCCAGACTCCAGAGAAGAGGCTGGAGTGGGTCGCCTCCATTAGT GATGGTGGTGGTGACACCTATTATCCAGACACTGTAAAGGGCCGATTCACCA TCTCCAGAGACAATGCCAAGAACACCCTGTACCTGCAAATGAGCCGTCTGAA GTCTGAGGACACAGCCATGTATTACTGTGCAAGACATAGGGGCTCTCTTGAC TACTGGGGCCAAGGCACCACTCTCACAGTCTCCTCA | 41 |

TABLE 2-continued

Anti-CLDN18.2 mAb heavy and light chain variable region sequences. Antibody CDRs are underlined.

| Name | Sequence | SEQ ID NO: |
|---|---|---|
| T158S2 VH | EVKLVESGGGLVQPGGSLKLSCATSGFTFSDYMFWIRQTPEKRLEWVASIS DGGGDTYYPDTVKGRFTISRDNAKNTLYLQMSRLKSEDTAMYYCARHRGSLD YWGQGTTLTVSS | 42 |
| T158S2 VL | GACATTGTGCTGACCCAATCTCCAGCTTCTTTGGCTGTGTCTCTAGGGCAGA GGGCCACCATCTCCTGCAGAGCCAGCGAGAGTGTGGATAACTATGGCTTTAG TTTTCTGCACTGGTACCAGCAGAAACCAGGACAGCCACCCAAACTCCTCATC TATCGTGCATCCAACCTAGCATCTGGGATCCCTGCCAGGTTCAGTGGCAGTG GGTCTAGGACAGACTTCACCCTCACCATTAATCCTGTGGAGACTGATGATGT TGCAACCTATTACTGTCAGCAAAGTAATCAGGGTCCACTCACGTTCGGTGCT GGGACCAAGCTGGAGCTGAAA | 43 |
| T158S2 VL | DIVLTQSPASLAVSLGQRATISCRASESVDNYGFSFLHWYQQKPGQPPKLLI YRASNLASGIPARFSGSGSRTDFTLTINPVETDDVATYYCQQSNQGPLTFGA GTKLELK | 44 |
| T224S8 VH | GAGGTTCAGCTGCAGCAGTCTGGGACAGAGCTTGTGAGGTCAGGGGCCTCAG TCAAGTTGTCCTGCACAACTTCTGGCTTCAACATTAAAGACTACTTTTTACA CTGGGTGAAGCAGAGGCCTGAACAGGGCCTGGAGTGGATTGGATGGATTGAT CCTGAGAATGGTGATACTAAATATGCCCCGAAGTTCCAGGACAAGGTCACCA TGACTGTGGACACATCCTCCAACACAGCCTGCCTGCACCTCAGCAGCCTGAC ATCTGATGACACTGCCGTCTATTACTGTAATGTACTAGGCTACGGTAATTAC GGACATTTTTACTATGCTATGGACTACTGGGGTCAAGGAACCCTCAGTCACCG TCTCCTCT | 45 |
| T224S8 VH | EVQLQQSGTELVRSGASVKLSCTTSGFNIKDYFLHWVKQRPEQGLEWIGWID PENGDTKYAPKFQDKVTMTVDTSSNTACLHLSSLTSDDTAVYYCNVLGYGNY GHFYYAMDYWGQGTSVTVSS | 46 |
| T224S8 VL | GATGTTGTGATGACCCAAACTCCACTCTCCCTGCCTGTCAGTCTTGGAGATC AGGCCTCCATCTCTTGCAGATCTAGTCAGAGCCTTGTACACAGTAATGGAAA CACCTATTTACATTGGTACCTGCAGAAGCCAGGCCAGTCTCCAAAGCTCCTG ATCTACAAAGTTTCCAACCGATTTTCTGGGGTCCCAGACAGGTTCAGTGGCA GTGAATCAGGGACAGATTTCACACTCAAGATCAGCAGAGTGGAGGCTGAGGA TCTGGGAATTTATTTCTGCTCTCAAAATACACATGTTCCTCGGACGTTCGGT GGAGGCACCAAGCTGGAAATCAGA | 47 |
| T224S8 VL | DVVMTQTPLSLPVSLGDQASISCRSSQSLVHSNGNTYLHWYLQKPGQSPKLL IYKVSNRFSGVPDRFSGSESGTDFTLKISRVEAEDLGIYFCSQNTHVPRTFG GGTKLEIR | 48 |
| T192S2 VH | GAAGTGAAGCTGGTGGAGTCTGGGGGAGGCTTAGTGCAGCCTGGAGGGTCCC TGAAACTCTCCTGTGCAACCTCTGGATTCACTTTCAGTGACTATTACATGTA TTGGGTTCGCCAGACTCCAGAGAAGAGGCTGGAGTGGGTCGCATACATTAGT AATGGTGGTGGTTCCACCTATTATCCAGACACTGTGAAGGGCCGATTCACCA TCTCCAGAGACAATGCCAAGAACACCCTGTACCTGCAAATGAGCCGTCTGAA GTCTGAGGACACAGCCATGTATTACTGTGCAAGACATAGGGGCTCTCTTGAC TTCTGGGGCCAAGGCACCACTCTCACAGTCTCCTCA | 49 |
| T192S2 VH | EVKLVESGGGLVQPGGSLKLSCATSGFTFSDYYMYWVRQTPEKRLEWVAYIS NGGGSTYYPDTVKGRFTISRDNAKNTLYLQMSRLKSEDTAMYYCARHRGSLD FWGQGTTLTVSS | 50 |
| T192S2 VL | GACATAGTGCTGACACAGTCTCCTGCTTCCTTAGCTGTATCTCTGGGGCAGA GGGCCACCATCTCCTGCAGAGCCAGCGAAAGTGTTGATAATTATGGCTTTAG TTTTATGCACTGGTACCAGCAGAAACCAGGACAGCCACCCAAACTCCTCATC TATCGTGCATCCAACCTAGAATCTGGGATCCCTGCCAGGTTCAGTGGCAGTT GGTCTAGGACAGACTTCACCCTCACCATTAATCCTGTGGAGACTGATGATGT TGCAACCTATTACTGTCAGCAAAGTAATAAGGTTCCGCTCACGTTCGGTGCT GGGACCAAGCTGGAGCTGAAA | 51 |
| T192S2 VL | DIVLTQSPASLAVSLGQRATISCRASESVDNYGFSFMHWYQQKPGQPPKLLI YRASNLESGIPARFSGSWSRTDFTLTINPVETDDVATYYCQQSNKVPLTFGA GTKLELK | 52 |
| T252S4 VH | GAGGTCCAGCTGCAACAGTCTGGACCTGAGCTGGTGAAGCCTGGAGCTTCAA TGAAGATATCCTGCAAGGCTTCTGGTTACTCATTCACTGGCTACAACATGAA CTGGGTGAAGCAGACCCATGGAAAGAACCTTGAGTGGATTGGACTTATTAAT CCTTACAATGGTGGTACTAGGTACAACCAGAAGTTCAAGGGCAAGGCCACAT TAACTGTAGACAAGTCATCCAGCACAGCCTACATGGAGCTCCTCAGTCTGAC ATCTGAGGACTCTGCAGTCTATTTCTGTGCAAGGATGGGACTTGGAAATGCT ATGGACTACTGGGGTCAAGGAACCCTCAGTCACCGTCTCCTCA | 53 |

TABLE 2-continued

Anti-CLDN18.2 mAb heavy and light chain variable region sequences. Antibody CDRs are underlined.

| Name | Sequence | SEQ ID NO: |
|---|---|---|
| T252S4 VH | EVQLQQSGPELVKPGASMKISCKASGYSFTGYNMNWVKQTHGKNLEWIGLIN PYNGGTRYNQKFKGKATLTVDKSSSTAYMELLSLTSEDSAVYFCARMGLGNA MDYWGQGTSVTVSS | 54 |
| T252S4 VL | GACATTGTGATGACACAGTCTCCATCCTCCCTGACTGTGACAGCAGGAGAGA AGGTCACTATGAGCTGCAAGTCCAGTCAGAATCTGTTAAACAGTGGAAATCA AAAGAACTACTTGACCTGGTACCAGCAGAAACCAGGGCAGCCTCCTAAACTG TTGATCTACTGGGCATCCACTATGGAATCTGGGGTCCCTGATCGCTTCACAG GCAGTGGATCTGGAACAGATTTCACTCTCACCATCAGCAGTGTGCAGGCTGA AGACCTGGCAGTTTATTACTGTCAGAATGATTATATTTATCCGCTCCCGTTC GGTGCTGGGACCAAGCTGGAGCTGAAA | 55 |
| T252S4 VL | DIVMTQSPSSLTVTAGEKVTMSCKSSQNLLNSGNQKNYLTWYQQKPGQPPKL LIYWASTMESGVPDRFTGSGSGTDFTLTISSVQAEDLAVYYCQNDYIYPLPF GAGTKLELK | 56 |
| T88S1 VH | CAGGTGCAGCTGAAGGAGTCAGGACCTGGCCTGGTGGCGCCCTCACAGAGCC TGTCCATCACATGCACCATCTCAGGGTTCTCATTAACCAGCTATGGTATACA CTGGGTTCGCCAGCCTCCAGGAAAGGGTCTGGAGTGGCTGGTAGTGATATGG AGTGATGGAAGAACAACCTATAATTCAGCTCTCAAATCCAGACTGAGCATCA GCAAGGACAACTCCAAGAGCCAAGTTTTCTTAAAAATGAACAGTCTCCAAAC TGATGACACAGCCATGTACTACTGTGCCAGACATGGTAGATACGACCCCTAT GCTATGGACTACTGGGGTCAAGGAACCTCAGTCACCGTCTCCTCA | 57 |
| T88S1 VH | QVQLKESGPGLVAPSQSLSITCTISGFSLTSYGIHWVRQPPGKGLEWLVVIW SDGRTTYNSALKSRLSISKDNSKSQVFLKMNSLQTDDTAMYYCARHGRYDPY AMDYWGQGTSVTVSS | 58 |
| T88S1 VL | GACATTGTGCTGACCCAATCTCCAGCTTCTTTGGCTGTGTCTCTAGGGCAGA GGGCCACCATCTCCTGCAGAGCCAGCGAGAGTGTGGATAACTATGGCTTTAG TTTTCTGCACTGGTACCAGCAGAAACCAGGACAGCCACCCAAACTCCTCATC TATCGTGCATCCAACCTAGCATCTGGGATCCCTGCCAGGTTCAGTGGCAGTG GGTCTAGGACAGACTTCACCCTCACCATTAATCCTGTGGAGACTGATGATGT TGCAACCTATTACTGTCAGCAAAGTAATCAGGGTCCACTCACGTTCGGTGCT GGGACCAAGCTGGAGCTGAAA | 59 |
| T88S1 VL | DIVLTQSPASLAVSLGQRATISCRASESVDNYGFSFLHWYQQKPGQPPKLLI YRASNLASGIPARFSGSGSRTDFTLTINPVETDDVATYYCQQSNQGPLTFGA GTKLELK | 60 |

Figure 2:
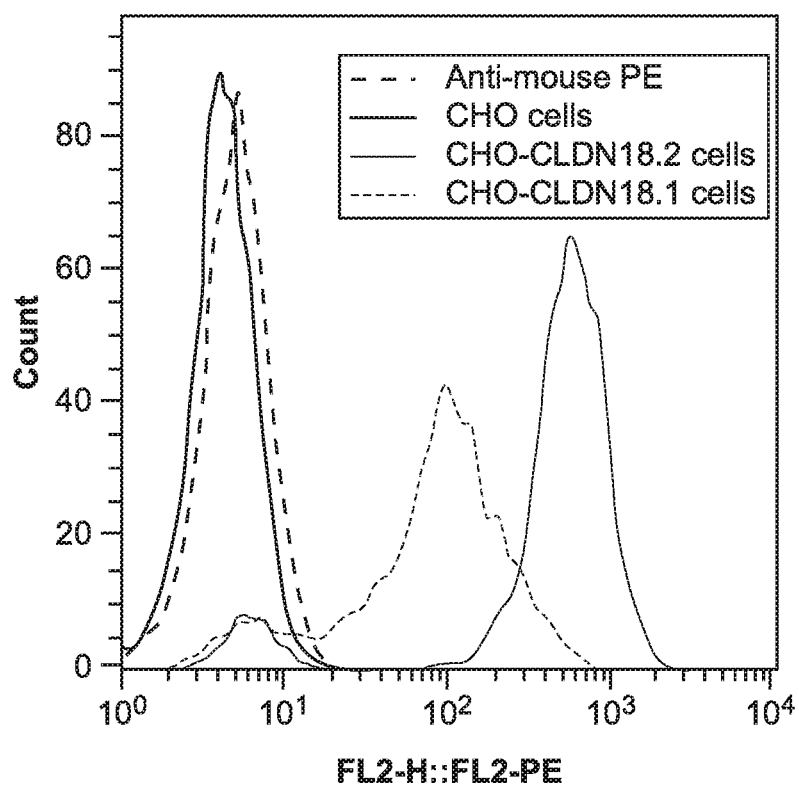
FIG. 2 shows that anti-CLDN 18.2 hybridoma antibody clone T29S9 binds to both CLDN 18.1 and CLDN 18.2 in the FACS analysis. T29S9 was used at 10 µg/ml in the analysis.

Example 2: Anti-CLDN 18.2 Mouse Monoclonal Antibody Binding Specificity and Affinity To evaluate the binding specificity of anti-CLDN 18.2 mouse hybridoma antibodies, the purified antibodies were analyzed by FACS analysis using CHO cells expressing either human CLDN 18.1 or human CLDN 18.2. The FACS analysis was done as described previously. As shown in FIGS. 1a and 1b, all 9 hybridoma antibodies bind to CHO cells expressing human CLDN 18.2 but not to CHO cells expressing human CLDN 18.1. One of the hybridoma antibody T29S9 bind to both CLDN 18.1 and 18.2 (FIG. 2).

Figure 3:
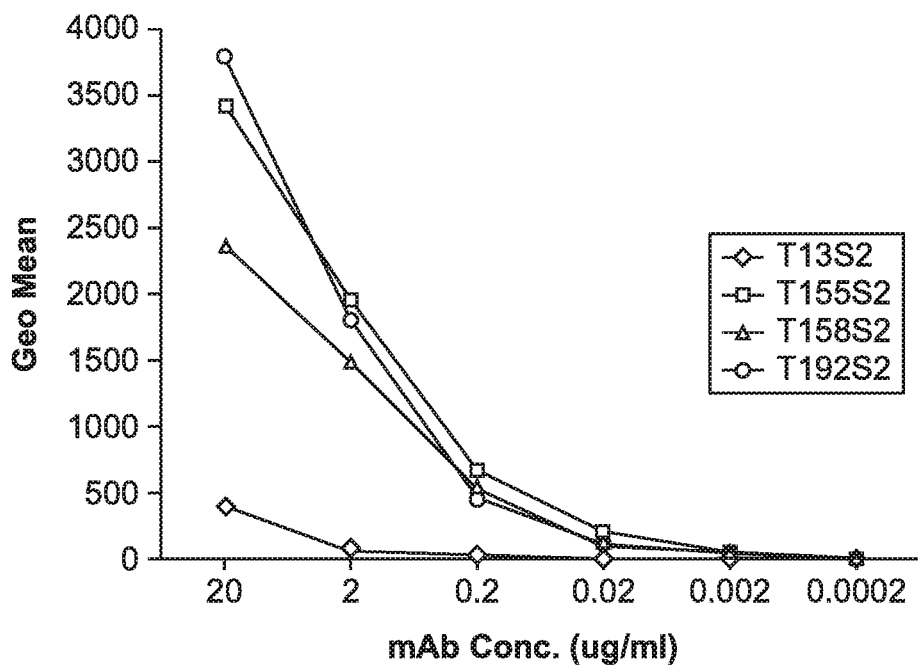
FIG. 3 shows binding of anti-CLDN 18.2 hybridoma antibodies with titration to CHO-CLDN 18.2 cells.
Figure 3:
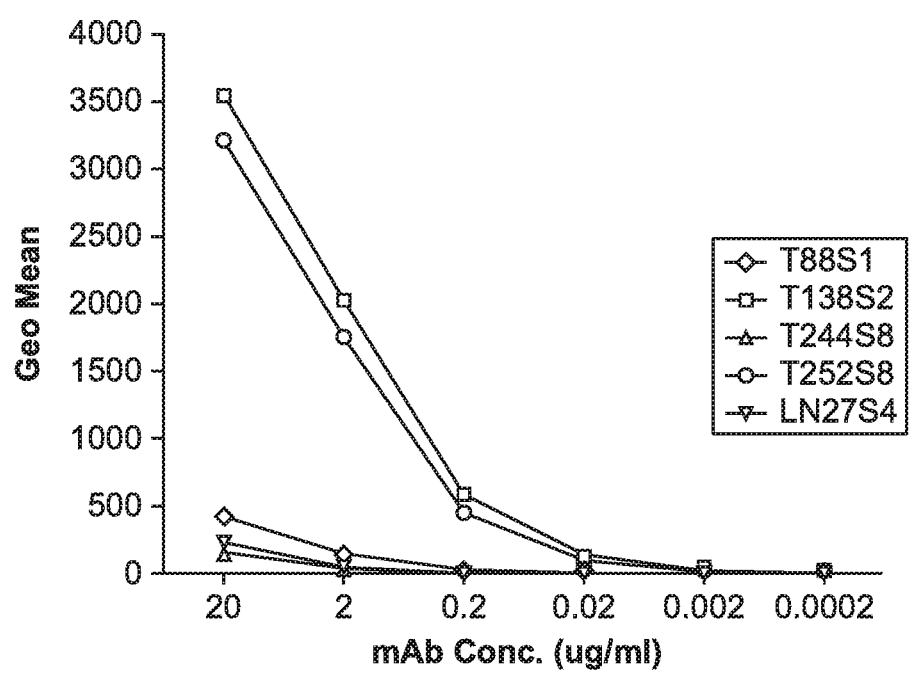

To evaluate the binding affinity of anti-CLDN 18.2 mouse hybridoma antibodies to cell surface expressed human CLDN 18.2, serial dilutions of anti-CLDN 18.2 purified antibodies were analyzed by FACS using CHO cells expressing human CLDN 18.2. As shown in FIG. 3, some of the antibodies had high binding affinity to cell surface CLDN 18.2, such as T138S2, T155S2, T158S2, T192S2, and T252S4 while others had medium to low binding affinities, such as T13S2, T88S1, T224S8 and LN27S4.

Figure 4:
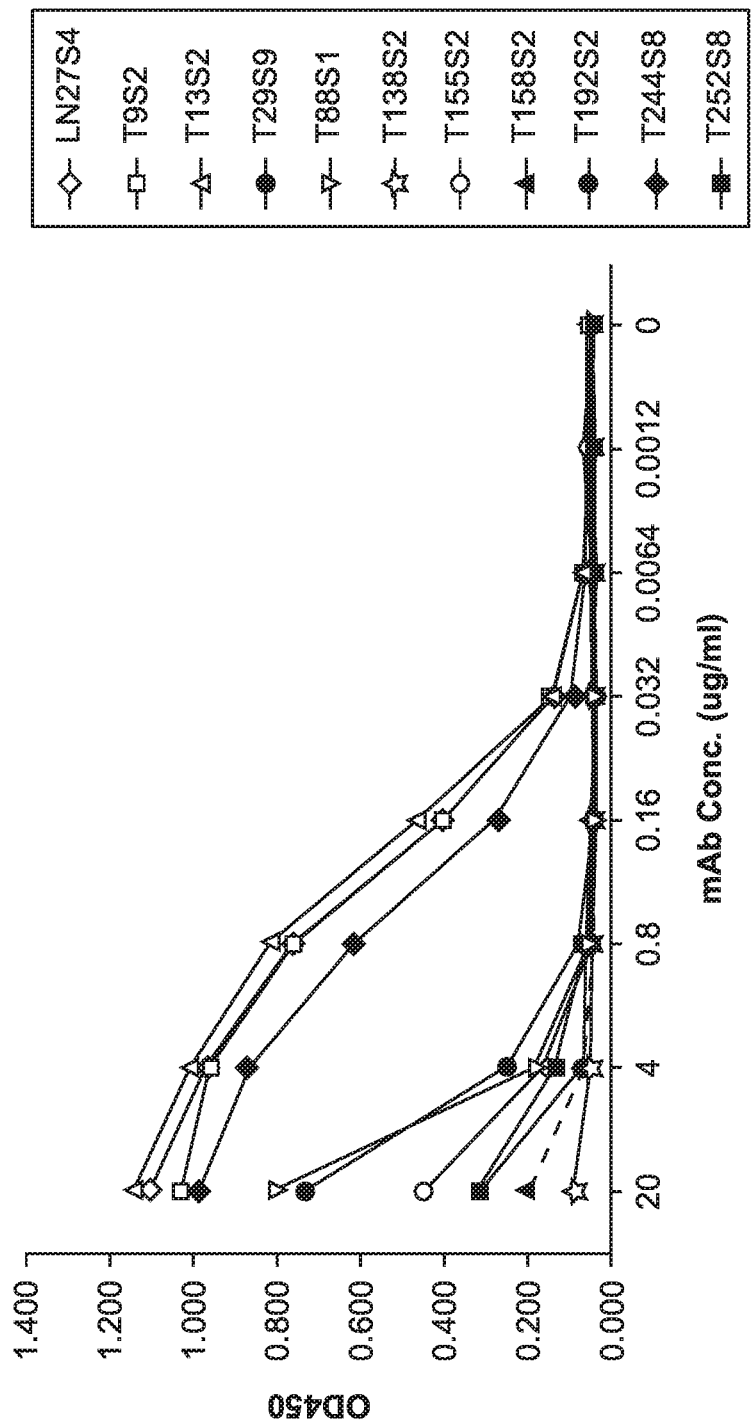
FIG. 4 shows the CLDN 18.2 hybridoma antibody binding to a plate coated with CLDN 18.2 EC1 Protein. Human CLDN 18.2EC1-huFc protein was coated onto ELISA wells at 1 µg/ml.

The binding of anti-human CLDN 18.2 antibody to human CLDN 18.2 can also be evaluated in ELISA assays. Briefly, 96 well microtiter plates were coated with human CLDN 18.2 huFc protein at 1 µ/ml in PBS, 100 µl/well at 4° C. overnight and then blocked with 100 p 1/well of 2% BSA at RT for 1 hour. Five-fold dilutions of purified mouse hybridoma antibodies starting from 20 p g/ml were added to each well and incubated for 1-2 hours at RT. The plates were washed with PBS/Tween and then incubate with goat-anti-mouse IgG antibody conjugated with Horse Radish Peroxidase (HRP) for 1 hour at RT. After washing, the plates were developed with TMB substrate and analyzed by spectrophotometer at OD 450 nm. As shown in FIG. 4, all antibodies can bind to plated coated human CLDN 18.2 protein at various degrees. It was interesting to observe that some of the antibodies which bind to cell surface CLDN 18.2 with high affinities, such as T138S2 and T158S2, did not bind to plate-coated CLDN 18.2 very well (FIG. 4).

Figure 5:
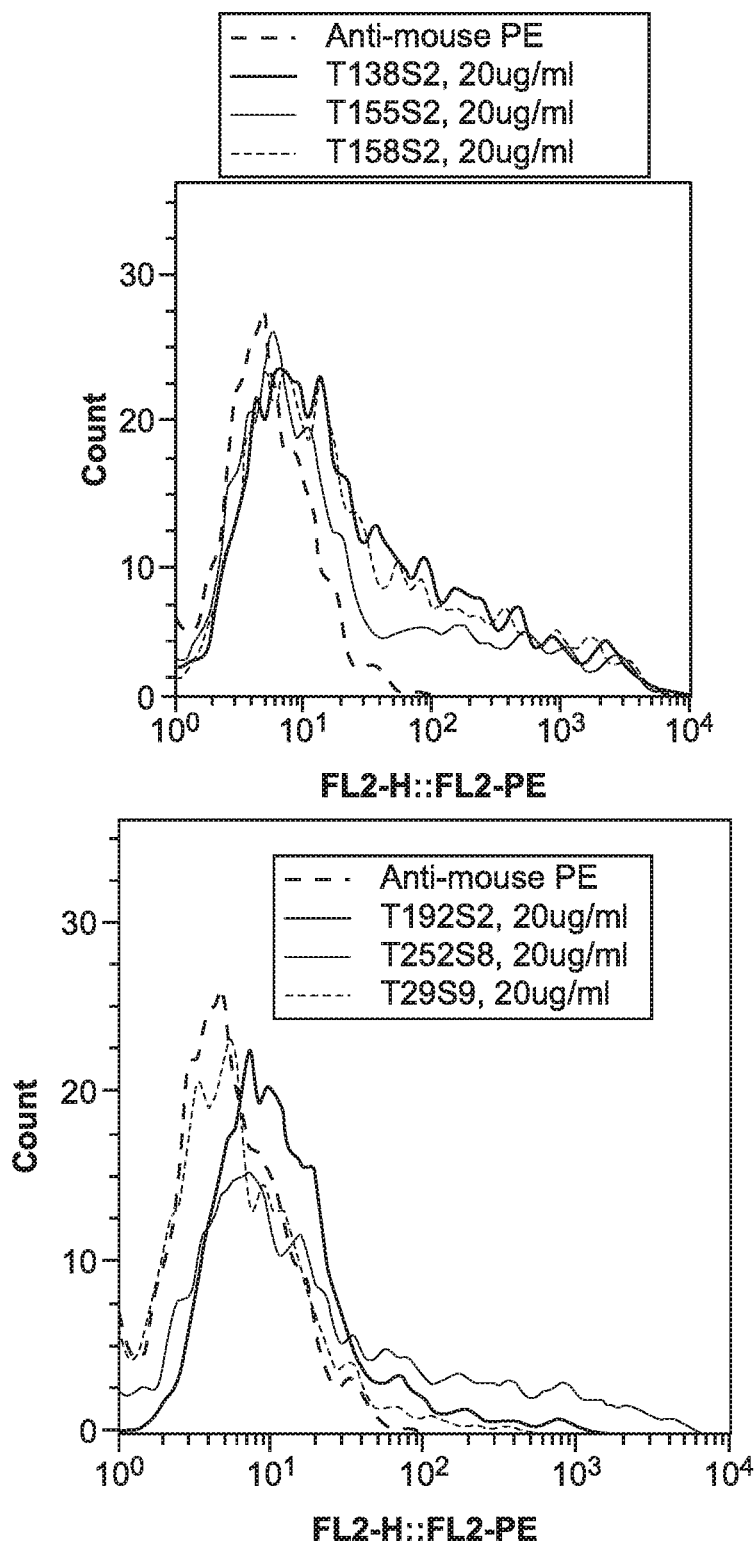
FIG. 5 shows the binding of Anti-CLDN 18.2 hybridoma antibodies to KATO III Cells. Anti-CLDN 18.2 hybridoma antibodies were used at 20 µg/ml in the FACS analysis.

Example 3: Anti-CLDN 18.2 Mouse Monoclonal Antibody Binding to KATO III Cells FACS assay was also used to evaluate the binding of anti-CLDN 18.2 antibodies to human gastric cancer cell line KATO III. As shown in FIG. 5, the six anti-CLDN 18.2 hybridoma antibodies can bind to KATO III cells at various levels.

Example 4: Anti-Human CLDN 18.2 Mouse/Human Chimeric Antibody Binding Affinity to Human CLDN 18.2 and KATO III Cells To produce anti-human CLDN 18.2 mouse/human chimeric antibodies, mouse antibody heavy and light chain V regions were cloned into transient expression vectors containing human antibody heavy chain IgG1 and light chain constant regions. The resulting antibody heavy and light chain expression constructs were used to transfect HEK293 cells. The culture supernatants were harvested and loaded onto protein A Sepharose columns (GE Healthcare). The columns were washed and antibodies were then eluted with eluting buffer (0.1 M glycine buffer, pH 3.0). Collected fractions were neutralized with 1 MTris-HCl, pH 8.0, pooled together and then dialyzed against PBS. Purity of the antibodies was analyzed by sodium dodecyl sulfate polyacrylamide gel electrophoresis (SDS-PAGE) under both reducing and non-reducing conditions. Protein bands were visualized by Coomassie brilliant blue staining.

Figure 6:
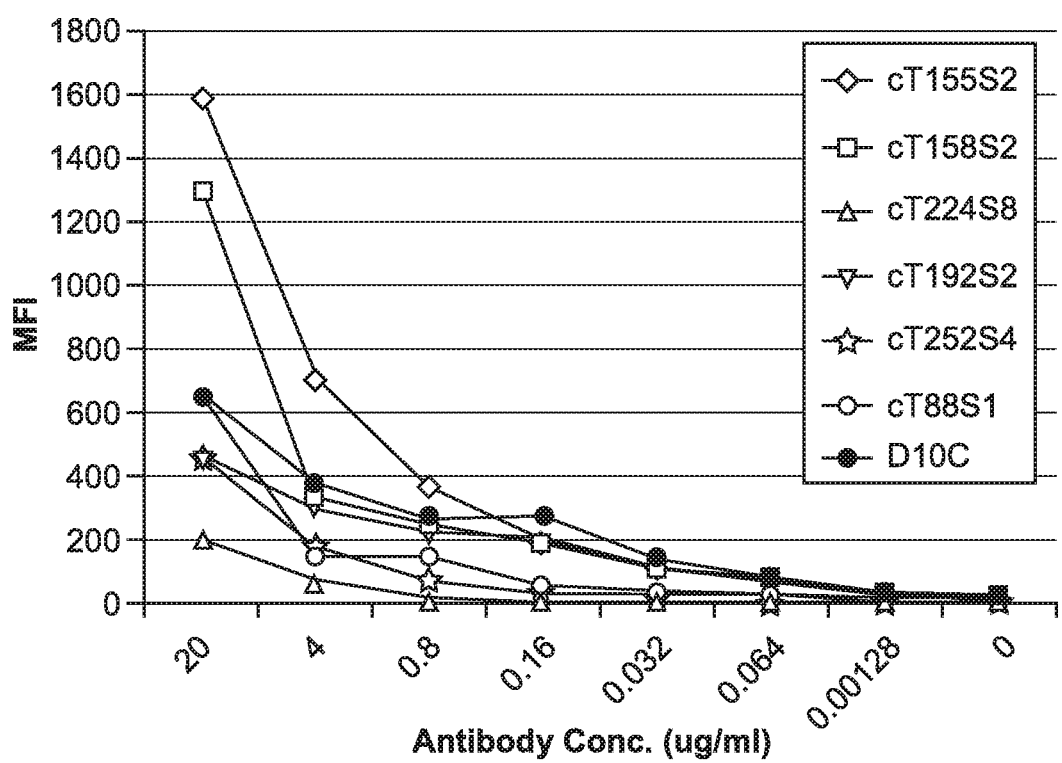
FIG. 6 shows binding of anti-CLDN 18.2 chimeric antibodies with titration to CHO-CLDN 18.2 cells in the FACS analysis.

To evaluate the binding affinity of anti-human CLDN 18.2 mouse/human chimeric antibodies to human CLDN 18.2, CHO cells expressing human CLDN 18.2 were first incubated with five fold serial diluted mouse/human chimeric mAbs starting at 100 μg/ml on ice for 30 min. The cells were then washed with PBS three times, followed by incubation with PE-labeled anti-human Fc gamma specific antibody (Jackson Immuno-Research) at 4° C. for 15 min. The cells were washed again with PBS three times and analyzed using an FACS Caliber instrument (Becton-Dickinson). As shown in FIG. 6, all six chimeric antibodies bind to CHO-CLDN 18.2 cells at similar affinity as their hybridoma counterparts. D10C is an anti-human CLDN 18.2 antibody identified by GanyMed and is used as a control.

Figure 7:
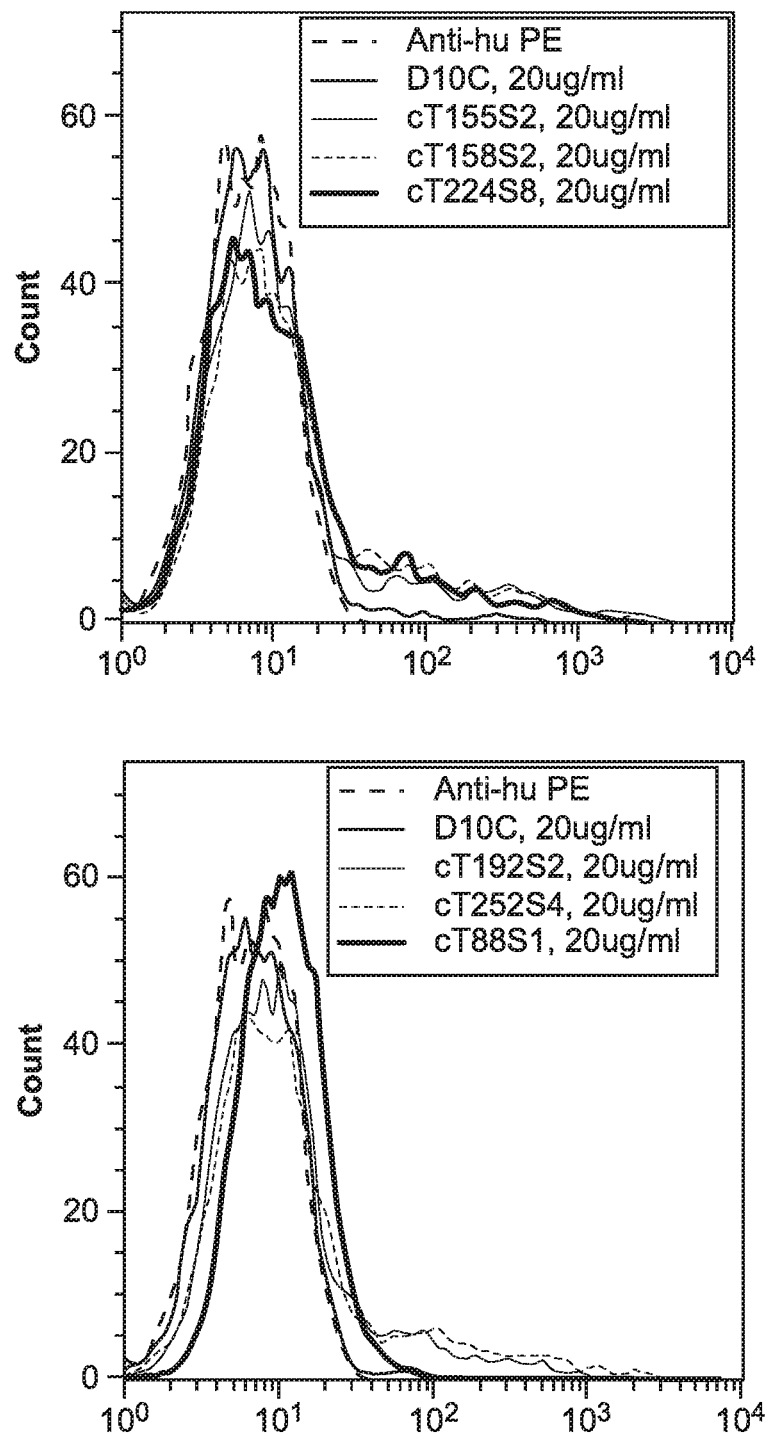
FIG. 7 shows binding of anti-CLDN 18.2 chimeric antibodies to KATO III cells. Anti-CLDN 18.2 chimeric antibodies were used at 20 µg/ml in the FACS analysis.
Figure 8A:
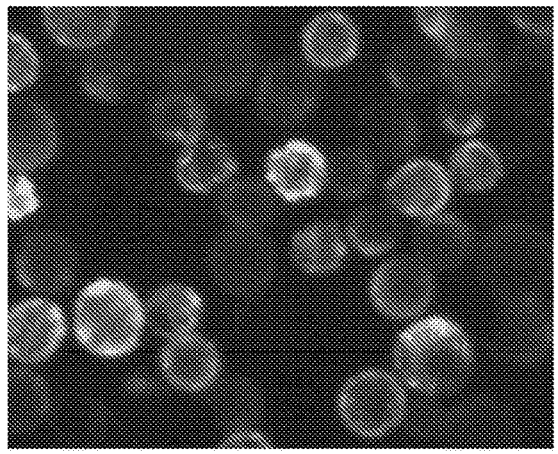
FIG. 8A-8E show anti-human CLDN 18.2 antibody-induced receptor internalization in CHO-CLDN 18.2 cells.
Figure 8A:
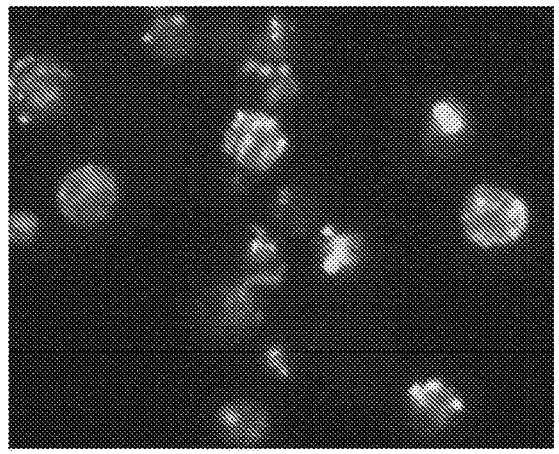
Figure 8B:
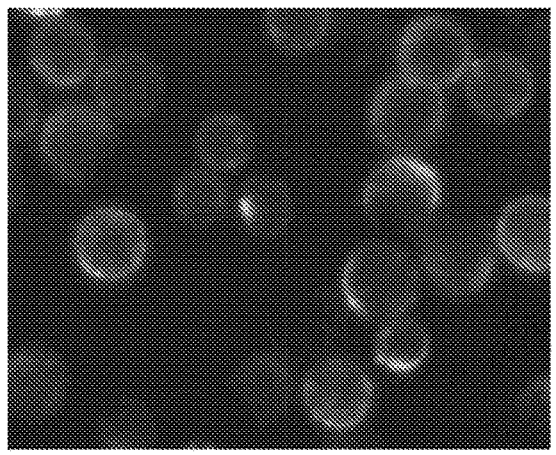
Figure 8B:
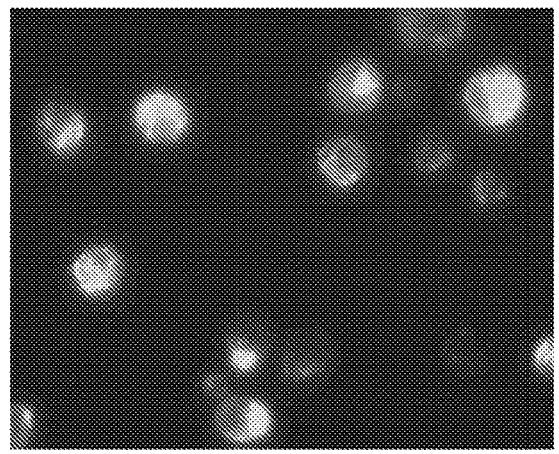
Figure 8C:
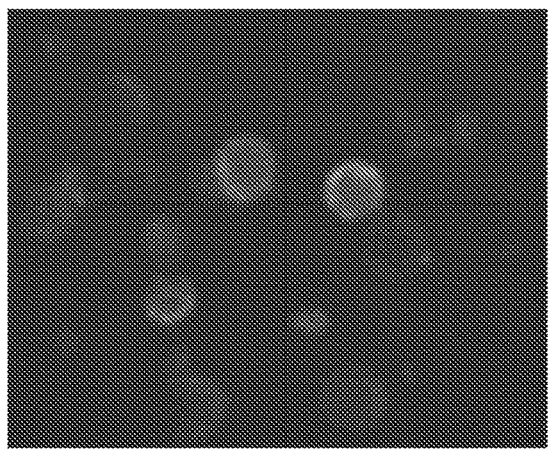
Figure 8C:
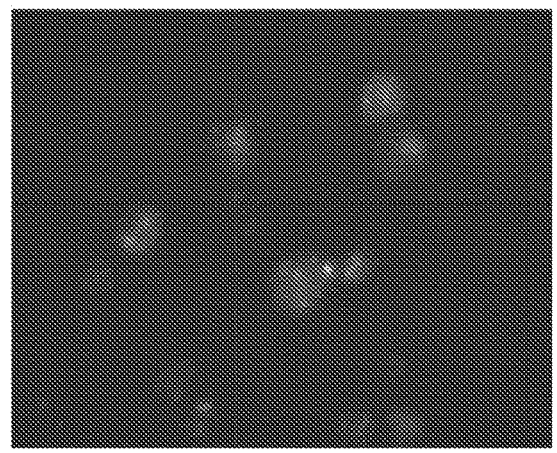
Figure 8D:
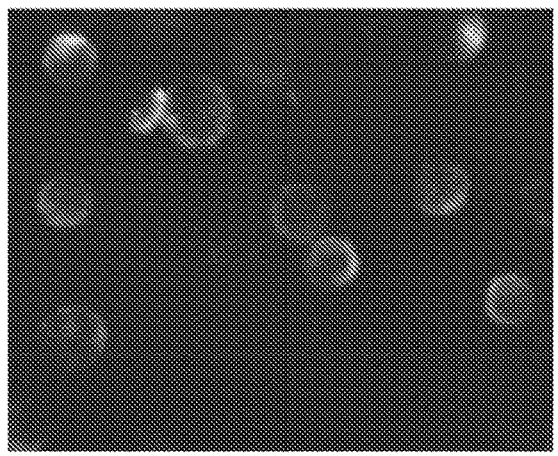
Figure 8D:
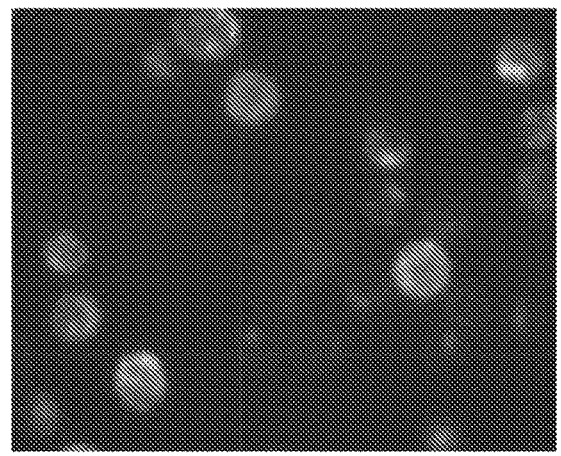
Figure 8E:
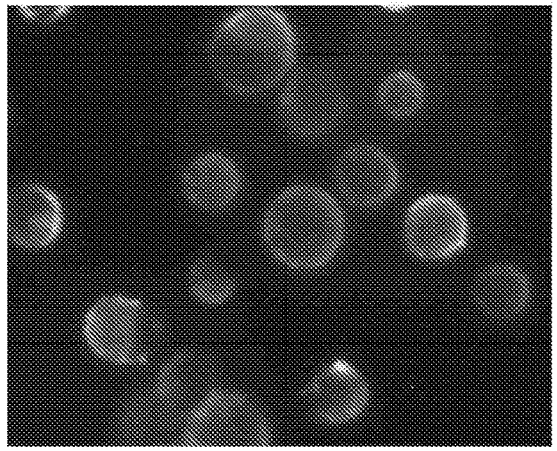
Figure 8E:
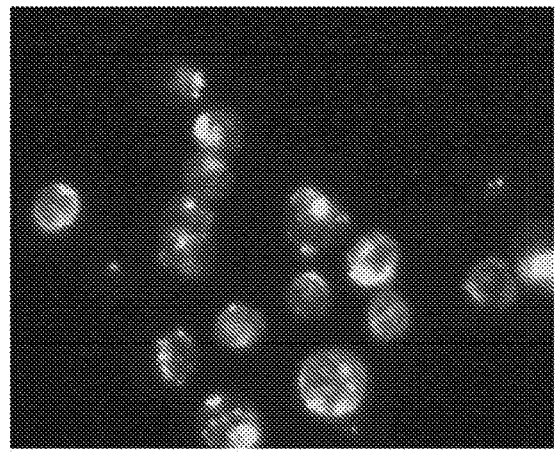

The binding affinities of anti-human CLDN 18.2 chimeric antibodies to human gastric cancer cell line KATO III were also evaluated by FACS. As shown in FIG. 7, the anti-CLDN 18.2 chimeric antibodies bound to only a small fraction of KATO III cells. However, most of the antibodies tested bound to KATO III cells at higher levels compared to the D10C antibody (FIG. 7).

Example 5: Anti-Human CLDN 18.2 Antibody-Induced Receptor Internalization in Target Cells The anti-human CLDN 18.2 antibody-induced CLDN 18/2 internalization was evaluated. Anti-human CLDN 18.2 antibodies, cT155S2, cT158S2, cT224S8, cT192S2, and cT252S4, were conjugated with FITC per manufacturer's instructions (Sigma). CHO-CLDN 18.2 cells were stained with the FITC-labeled antibodies at 4° C. for 20 min and washed with PBS twice, followed by incubation at 37° C. for 0 hr (for cell surface binding) or 3 hr (for antibody internalization). The cells were then analyzed by fluorescence microscopy. As shown in FIGS. 8a-8e, all of the tested anti-human CLDN 18.2 antibodies, including cT155S2, cT158S2, cT224S8, cT192S2, and cT252S4, effectively induced CLDN 18.2 internalization on CHO-CLDN 18.2 cells (FIGS. 8a-8e). These data demonstrated that the anti-CLDN 18.2 antibodies conjugated with a cytotoxin or cytotoxic agents can be internalized by target cancer cells expressing CLDN 18.2. Thus the anti-CLDN 18.2 antibody-toxin conjugates can be used as antibody-drug conjugates (ADCs) for treatment of cancer and other diseases.

Example 6: Humanization of Mouse Anti-Human CLDN 18.2 Antibody T252S4

The mAb T252S4 variable region genes were employed to create a humanized MAb. In the first step of this process, the amino acid sequences of the VH and VK of MAb T252S4 were compared against the available database of human Ig gene sequences to find the overall best-matching human germline Ig gene sequences. For the light chain, the closest human match was the IGKV4-1 gene, and for the heavy chain the closest human match was the IGVH5-51 gene.

Humanized variable domain sequences were then designed where the CDR1, CDR2, and CDR3 sequences (underlined sequences in Table 3) of the T252S4 light chain were grafted onto framework sequences of the IGKV4-1 gene, and the CDR1, CDR2, and CDR3 sequences (underlined sequences in Table 3) of the T252S4 heavy chain were grafted onto framework sequences of the IGVH5-51. A 3D model was then generated to determine if there were any framework positions where replacing the mouse amino acid to the human amino acid could affect binding and/or CDR conformation. The amino acid and nucleotide sequences of some of the humanized antibody are listed in Table 3 below.

TABLE 3

Humanized T252S4 antibody sequences (CDRs are underlined)

| Name | Sequence | SEQ ID NO: |
|---|---|---|
| Chimeric T252S4 VH | EVQLQQSGPELVKPGASMKISCKASGYSFT GYNMN WVKQTHGKNLEWIG LINPYNGGTRYNQKFKG KATLTVDKSSSTAYMELLSLTSEDSAVYFCAR MGLGNAMDY WGQGTSVTVSS | 61 |
| HuT252S4 VH1 | EVQLVQSGAEVKKPGESLKISCKGSGYSFT GYNMN WVRQMPGKGLEWMG LINPYNGGTRYNQKFKG QVTISADKSISTAYLQWSSLKASDTAMYFCAR MGLGNAMDY WGQGTTVTVSS | 62 |
| HuT252S4 VH2 | EVQLVQSGAEVKKPGESLKISCKGSGYSFT GYNMN WVRQMPGKNLEWIG LINPYNGGTRYNQKFKG QVTISADKSISTAYLQWSSLKASDTAMYFCAR MGLGNAMDY WGQGTTVTVSS | 63 |
| HuT252S4 VH3 | EVQLVQSGAEVKKPGESLKISCKGSGYSFT GYNMN WVRQMPGKNLEWIG LINPYNGGTRYNQKFKG KATLSVDKSISTAYLQWSSLKASDTAMYFCAR MGLGNAMDY WGQGTTVTVSS | 64 |

TABLE 3-continued

Humanized T252S4antibody sequences (CDRs are underlined)

| Name | Sequence | SEQ ID NO: |
|---|---|---|
| Chimeric T252S4 VL | DIVMTQSPSSLTVTAGEKVTMSC <u>KSSQNLLNSGNQKNYLT</u> WYQQKPGQPPKLLIY <u>WASTMES</u> GVPDRFTGSGSGTDFTLTISSVQAEDLAVYYC <u>QNDYIYPLP</u> FGAGTKLELK | 65 |
| HuT252S4 VL1 | DIVMTQSPDSLAVSLGERATINC <u>KSSQNLLNSGNQKNYLT</u> WYQQKPGQPPKLLIY <u>WASTMES</u> GVPDRFSGSGSGTDFTLTISSLQAEDVAVYYC <u>QNDYIYPLP</u> FGQGTKLEIK | 66 |
| HuT252S4 VL2 | DIVMTQSPDSLAVSLGERATINC <u>KSSQNLLQSGNQKNYLT</u> WYQQKPGQPPKLLIY <u>WASTRES</u> GVPDRFSGSGSGTDFTLTISSLQAEDVAVYYC <u>QNDYIYPLP</u> FGQGTKLEIK | 67 |
| Chimeric T252S4 VH | GAGGTCCAGCTGCAACAGTCTGGACCTGAGCTGGTGAAGCCTGGAGCTTCAATGAAGAT ATCCTGCAAGGCTTCTGGTTACTCATTCACT<u>GGCTACAACATGAAC</u>TGGGTGAAGCAGA CCCATGGAAAGAACCTTGAGTGGATTGGA<u>CTTATTAATCCTTACAATGGTGGTACTAGG TACAACCAGAAGTTCAAGGGC</u>AAGGCCACATTAACTGTAGACAAGTCATCCAGCACAGC CTACATGGAGCTCCTCAGTCTGACATCTGAGGACTCTGCAGTCTATTTCTGTGCAAGGA <u>TGGGACTTGGAAATGCTATGGACTAC</u>TGGGGTCAAGGAACCTCAGTCACCGTCTCCTCA | 68 |
| HuT252S4 VH1 | GAAGTCCAGCTCGTGCAGTCTGGTGCGGAGGTCAAAAAACCCGGCGAGTCTCTCAAAAT TAGTTGCAAAGGCTCCGGTTATTCATTCACG<u>GGTTACAATATGAAC</u>TGGGTTCGACAAA TGCCGGGTAAGGGACTTGAATGGATGGGA<u>TTGATCAACCCCTATAACGGAGGTACCAGA TACAACCAAAAATTTAAGGGC</u>CAGGTGACTATTAGTGCAGATAAAAGTATCTCCACCGC TTACCTCCAATGGTCTAGTTTGAAGGCGTCTGACACTGCTATGTACTTTTGCGCGAGAA <u>TGGGGTTGGGAAATGCGATGGACTAC</u>TGGGGTCAGGGCACTACGGTTACGGTCTCCTCT | 69 |
| HuT252S4 VH2 | GAGGTACAGCTCGTGCAATCTGGGGCCGAAGTAAAGAAACCTGGAGAAAGTCTTAAAAT AAGCTGCAAGGGCAGTGGGTATAGCTTCACG<u>GGCTACAATATGAAC</u>TGGGTTAGACAAA TGCCAGGTAAGAACCTCGAATGGATAGGA<u>TTGATCAACCCATACAATGGTGGTACGCGC TACAACCAGAAATTCAAAGGT</u>CAGGTTACCATCTCTGCGGATAAAAGCATCTCAACGGC GTATCTTCAATGGTCCTCACTGAAAGCATCCGACACAGCAATGTATTTTTGCGCTAGAA <u>TGGGATTGGGTAATGCCATGGACTAC</u>TGGGGCCAAGGCACCACGGTTACAGTCTCTTCC | 70 |
| HuT252S4 VH3 | GAAGTTCAGCTGGTGCAAAGTGGGGCTGAGGTAAAGAAGCCTGGCGAGAGCCTCAAGAT TTCTTGCAAGGGTAGCGGATACAGTTTTACG<u>GGATATAACATGAAT</u>TGGGTTCGCCAGA TGCCGGGGAAGAACCTTGAATGGATAGGA<u>CTGATAAACCCCTATAATGGGGGAACCCGA TATAATCAGAAGTTTAAGGGA</u>AAAGCAACTTTGTCAGTTGACAAGTCTATCAGCACGGC CTATCTTCAGTGGTCCAGTCTGAAAGCAAGCGACACGGCTATGTACTTTTGTGCACGCA <u>TGGGGCTTGGTAACGCAATGGACTATT</u>GGGGACAAGGAACTACCGTCACTGTCTCTTCA | 71 |
| Chimeric T252S4 VL | GACATTGTGATGACACAGTCTCCATCCTCCCTGACTGTGACAGCAGGAGAGAAGGTCAC TATGAGCTGC<u>AAGTCCAGTCAGAATCTGTTAAACAGTGGAAATCAAAAGAACTACTTGA CCT</u>GGTACCAGCAGAAACCAGGGCAGCCTCCTAAACTGTTGATCTACTGGGCATCCACT <u>ATGGAATCT</u>GGGGTCCCTGATCGCTTCACAGGCAGTGGATCTGGAACAGATTTCACTCT CACCATCAGCAGTGTGCAGGCTGAAGACCTGGCAGTTTATTACTGT<u>CAGAATGATTATA TTTATCCGCTCCCGTT</u>CGGTGCTGGGACCAAGCTGGAGCTGAAA | 72 |
| HuT252S4 VL1 | GACATCGTGATGACCCAGTCCCCGGACAGTCTGGCAGTCAGTCTTGGGGAAAGAGCTAC CATAAACTGC<u>AAATCCAGCCAAAACCTTCTTAATAGCGGCAACCAAAAGAATTACTTGA CTT</u>GGTATCAGCAAAAACCCGGGTCAGCCGCCCAAACTCTTGATATACTGGGCGTCTACG <u>ATGGAAAGC</u>GGCGTCCCCGACCGCTTCAGCGGGAGTGGGTCAGGGACTGATTTCACTTT GACAATCAGTTCCCTTCAGGCAGAGGACGTAGCAGTCTACTACTGT<u>CAGAATGATTATA TATATCCTCTTCCG</u>TTCGGCCAGGGGACGAAGTTGGAGATCAAA | 73 |
| HuT252S4 VL2 | GACATCGTGATGACTCAAGTCCTGACTCCCTTGCTGTTTCACTTGGCGAAAGGGCCAC TATCAACTGT<u>AAGAGTTCTCAGAATCTCTTGCAATCAGGAAACCAGAAGAATTACTTGA CCT</u>GGTATCAACAGAAGCCTGGACAACCACCTAAGCTCTTGATTTACTGGGCTAGTACA <u>AGGGAGTCC</u>GGCGTCCCAGACAGATTTTCCGGTTCTGGATCAGGCACGGACTTCACTCT GACAATCTCAGTCTTCAAGCCGAGGATGTGGCCGTTTATTATTGC<u>CAGAACGATTACA TTTACCCTTTGCCATT</u>TGGTCAAGGTACTAAGTTGGAGATAAAA | 74 |

The humanized VH and VK genes were produced synthetically and then respectively cloned into vectors containing the human gamma 1 and human kappa constant domains. The pairing of the human VH and the human VK created 6 humanized antibodies (see Table 4).

TABLE 4

Humanized T252S4 antibodies with their VH and VL regions

| VH \ VL | Chimeric T252S4VL | HuT252S4VL1 | HuT252S4VL2 |
|---|---|---|---|
| Chimeric T252S4VH | Chimeric T252S4 H/L | | |
| HuT252S4VH1 | | HuT252S4 H1/L1 | HuT252S4 H1/L2 |
| HuT252S4VH2 | | HuT252S4 H2/L1 | HuT252S4 H2/L2 |
| HuT252S4VH3 | | HuT252S4 H3/L1 | HuT252S4 H3/L2 |

Example 7: Humanized T252S4 Antibodies Specifically Bind to Cell Surface Human CLDN 18.2 on CHO Cells Stably Expressing CLDN 18.2

To evaluate the binding activities of the humanized T252S4 antibodies to human CLDN 18.2 on cell surface, humanized T252S4 antibodies were produced from HEK293 cells. Briefly, the three HuT252S4 antibody heavy chain V regions (H1, H2, and H3) and two light chain V regions (L1 and L2) were paired in different combinations (Table 5) to transfect HEK293 cells, resulting in six humanized T252S4 antibodies. The chimeric T252S4 H/L was also expressed for comparison. The culture supernatants were harvested and loaded onto protein A Sepharose columns (GE Healthcare). The columns were washed and antibodies were then eluted with eluting buffer (0.1 M glycine buffer, pH 3.0). Collected fractions were neutralized with 1 M Tris-HCl, pH 8.0, pooled together and then dialyzed against PBS. Purity of the antibodies was analyzed by sodium dodecyl sulfate polyacrylamide gel electrophoresis (SDS-PAGE) under both reducing and non-reducing conditions.

To evaluate the binding activities of the humanized T252S4 antibodies to cell surface-expressed human CLDN 18.2, serial dilutions of purified humanized anti-CLDN 18.2 antibodies were analyzed by FACS using CHO cells expressing human CLDN 18.2. As shown in FIG. 9, all humanized T252S4 antibodies, including HuT252S4 H1/L1, HuT252S4H2/L1, HuT252S4H3/L1, HuT252S4H1/L2, HuT252S4H2/L2, and HuT252S4H3/L2, had high binding affinities to cell surface CLDN 18.2. The humanized T252S4 antibodies, with EC50 ranging from 0.47 to 1 µg/ml, had similar affinities with or higher affinities than the chimeric T252S4 antibody (EC50 at 1 µg/ml) binding to cell surface CLDN 18.2 (FIG. 9).

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed is:

1. An isolated antibody or fragment thereof comprising a heavy chain (HC) immunoglobulin variable domain sequence and a light chain (LC) immunoglobulin variable domain sequence, wherein the antibody binds to an epitope of CLDN 18.2, and does not bind to CLDN 18.1, and wherein the LC comprises (a) a CDR1 comprising the amino acid sequence QNLLNSSNQKNY (SEQ ID NO: 1), (b) a CDR2 comprising the amino acid sequence FAS (SEQ ID NO: 2), (c) a CDR3 comprising the amino acid sequence QQHYSTPLT (SEQ ID NO: 3); and wherein the HC comprises: (d) a CDR1 comprising the amino acid sequence GFTFSSYA (SEQ ID NO: 4), (e) a CDR2 comprising the amino acid sequence ISGGGST (SEQ ID NO: 5), and (f) a CDR3 comprising the amino acid sequence GGNIYDGYPYYFDY (SEQ ID NO: 6).

2. The antibody or fragment thereof of claim 1, wherein the HC variable region comprises:
EVKLVESGGGLVKPGGSLKLSCAASGFTFSSYAMSWVRQTPEKRLEWVASISGGGSTYYPDSVKGRFTISRDNARNILYLQMSYLRSEDTAVYYCARGGNIYDGYPYYFDYWGQGTTLTVSS (SEQ ID NO: 38) or an equivalent polypeptide having at least 90% identity to the polypeptide comprising SEQ ID NO: 38 or a polypeptide that is encoded by a polynucleotide that hybridizes under conditions of high stringency to the complement of a polynucleotide encoding the polypeptide comprising SEQ ID NO: 38;
and
wherein the LC variable region comprises:
DIVMTQSPSSLAMSVGQKVTMSCKSSQNLLNSSNQKNYLAWYQQKPGQSPKLLVYFASTRESGVPDRFTGSGSGTDFTLTISSVQAEDLAVYYCQQHYSTPLTF GAGTKLELK (SEQ ID NO: 40) or an equivalent polypeptide having at least 90% identity to SEQ ID NO: 40 or a polypeptide that is encoded by a polynucleotide that hybridizes under conditions of high stringency to the complement of a polynucleotide encoding the polypeptide comprising SEQ ID NO: 40.

3. The antibody or fragment thereof of claim 2, wherein an equivalent comprises an polypeptide having at least 90% amino acid identity to the polypeptide comprising SEQ ID NO: 38 or 40.

4. The antibody or fragment thereof of claim 1, wherein the HC comprises:
EVKLVESGGGLVKPGGSLKLSCAASGFTFSSYAM-SWVRQTPEKRLEWVASISGG GSTYYPDSVKGRFTISRDNARNILYLQM-SYLRSEDTAVYYCARGGNIYDG YPYYFDYWGQGTTLTVSS (SEQ ID NO: 38) and wherein the LC variable region comprises:

```
                                    (SEQ ID NO: 40)
DIVMTQSPSSLAMSVGQKVTMSCKSSQNLLNSSNQKNYLAWYQQKPGQS

PKLLVYFASTRESGVPDRFTGSGSGTDFTLTISSVQAEDLAVYYCQQHY

STPLTFGAGTKLELK.
```

5. The antibody or fragment thereof of any one of claims 1, 2, 3, or 4, wherein the antibody or fragment thereof is selected from the group consisting of a monoclonal antibody, a bispecific antibody, chimeric or humanized antibody and/or is comprised in an immunoconjugate or an antibody drug conjugate (ADC) which comprises the antibody or fragment thereof and an additional agent.

6. The antibody or fragment thereof of claim 5, wherein the bispecific antibody has a binding specific to a second target protein selected from the group of IL-1, CD3, CD16, CD19, CD20, CD28, CD64, PD-1, PD-L1, CTLA-4, LAG-3, CD28, CD122, 4-1BB, TIM3, OX-40, OX40L, CD40, CD40L, LIGHT, ICOS, ICOSL, GITR, GITRL, TIGIT, CD27, VISTA, B7H3, B7H4, HEVM, BTLA and KIR, or wherein the additional agent is selected from the group of a toxin, a drug, a therapeutic agent, a prodrug, a peptide, a protein, an enzyme, a virus, a lipid, a biological response modifier, a pharmaceutical agent, or polyethylene glycol (PEG).

7. A chimeric antigen receptor (CAR) comprising: (a) an antigen binding domain of an CLDN 18.2 antibody or fragment thereof of claim 1, 2, 3, or 4, (b) a CD8α hinge domain; (c) a CD8α transmembrane domain; (d) a 4-1BB costimulatory signaling region; and
(e) a CD3 zeta signaling domain.

8. The CAR of claim 7, further comprising a linker polypeptide located between the anti-CLDN 18.2 HC variable region and the anti-CLDN 18.2 LC variable region.

9. An isolated nucleic acid sequence encoding the antibody or fragment thereof of any one of claims 1, 2, 3, or 4, or a CAR comprising an antigen binding domain of the antibody.

10. The isolated nucleic acid of claim 9, further comprising one or more of the following: a Kozak consensus sequence located upstream of the antigen binding domain of the anti-CLDN 18.2 antibody, an enhancer, or an antibiotic resistance polynucleotide.

11. A method of inhibiting the growth of a tumor that expresses or overexpresses CLDN 18.2 in a subject in need thereof, comprising administering to the subject an effective amount of the antibody or fragment thereof of any one of claims 1, 2, 3, or 4.

12. A method of treating a cancer that expresses or overexpresses CLDN 18.2 in a patient in need thereof, comprising administering to the subject an effective amount of the antibody or fragment thereof of any one of claims 1, 2, 3, or 4.

13. A method for determining if a patient is likely to respond or is not likely to respond to an anti-CLDN 18.2 therapy, comprising contacting a cancer cell sample isolated from the patient with an effective amount of the antibody or fragment thereof of any one of claims 1, 2, 3, or 4, and detecting the presence of any antibody or fragment thereof bound to the sample, wherein the presence of antibody or fragment thereof bound to the sample indicates that the patient is likely to respond to the anti-CLDN 18.2 therapy and the absence of antibody or fragment thereof bound to the sample indicates that the patient is not likely to respond to the anti-CLDN 18.2 therapy.

14. A method of detecting a pathological cell in a sample isolated from a subject, comprising
 (a) detecting the level of CLDN 18.2 in a biological sample from the subject by detecting a complex formed by the antibody or fragment thereof of any one of claims 1, 2, 3, or 4; and
 (b) comparing the level of CLDN 18.2 observed in step (a) with the levels of CLDN 18.2 observed in a control biological sample;
 wherein the pathological cell is detected when the level of CLDN 18.2 is elevated compared to that observed in the control biological sample, optionally wherein the detection comprises one or more of immunohistochemistry (IHC), Western Blotting, Flow cytometry or ELISA.

* * * * *